(12) United States Patent
Briska et al.

(10) Patent No.: US 9,328,388 B2
(45) Date of Patent: May 3, 2016

(54) METHODS OF IDENTIFYING AN ORGANISM

(75) Inventors: Adam Michael Briska, Madison, WI (US); Emily B. Zentz, Germantown, MD (US)

(73) Assignee: OpGen, Inc., Gaithersburg, MD (US)

( * ) Notice: Subject to any disclaimer, the term of this patent is extended or adjusted under 35 U.S.C. 154(b) by 821 days.

(21) Appl. No.: 13/159,232

(22) Filed: Jun. 13, 2011

(65) Prior Publication Data
US 2015/0284777 A1  Oct. 8, 2015

Related U.S. Application Data

(63) Continuation-in-part of application No. 12/120,586, filed on May 14, 2008.

(60) Provisional application No. 61/029,816, filed on Feb. 19, 2008.

(51) Int. Cl.
*C07H 21/02* (2006.01)
*C12Q 1/00* (2006.01)
*C12Q 1/68* (2006.01)
*C12Q 1/04* (2006.01)
*C12Q 1/10* (2006.01)

(52) U.S. Cl.
CPC *C12Q 1/689* (2013.01); *C12Q 1/04* (2013.01); *C12Q 1/10* (2013.01)

(58) Field of Classification Search
CPC ............. C07H 21/00; C12Q 1/00; C12Q 1/68
USPC ................ 435/4, 6, 6.1, 6.11, 6.15; 536/23.1, 536/23.7, 24.32
See application file for complete search history.

(56) References Cited

U.S. PATENT DOCUMENTS 5,708,160 A    1/1998  Goh et al.
2003/0087280 A1  5/2003  Schwartz et al.

OTHER PUBLICATIONS

Kotewicz, M.L., et al. Optical Maps distinguish individual *Eschericahia coli* O157:H7 isolates. Abstracts of the General Meeting of the American Society for Microbiology, vol. 106, p. 288, Presentation No. H-136, May 2006.*
Kotewicz et al. Optical mapping and 454 sequencing of *Escherichia coli* 0157 : H7 isolates linked to the US 2006 spinach-associated outbreak, Microbiology Nov. 2008 vol. 154 p. 11 pp. 3518-3528. Especially abstract, p. 3519 col. 2, p. 3522 fig 1 and fig 2, p. 3523 col. 2 para 2 to p. 3524 col. 1 para 1, p. 3524 fig 4.
Perna et al Genome sequence of enterohaemorrhagic *Escherichia coli* 0157:H7. Nature Jun. 25, 2001 vol. 409 No. 6819 pp. 529-533. Especially p. 532 col. 2 para 3.
ISR and Written opinion mailed Nov. 30, 2012 for International Application No. PCT/US12/41336 10 pages.

* cited by examiner

*Primary Examiner* — Rodney P Swartz
(74) *Attorney, Agent, or Firm* — Thomas C. Meyers; Brown Rudnick LLP

(57) ABSTRACT

This disclosure features methods of identifying an organism. In certain embodiments, the invention provides methods of distinguishing virulent and non-virulent strains of organisms, such as *E. coli*.

9 Claims, 10 Drawing Sheets

SEQUENCE LISTING

```
<160> NUMBER OF SEQ ID NOS: 3

<210> SEQ ID NO 1
<211> LENGTH: 37782
<212> TYPE: DNA
<213> ORGANISM: Escherichia coli

<400> SEQUENCE: 1
catggccgtg gccgggtcgt tgcgcttctt cggtttcct gaagatgccg tgacgtttat      60
cggcgcatca atcggtttta tgggcgcaga gaaagcacgc gacaaggtta ttgcggcctt     120
taatcgcagg gtgaaggaga aggacgaatg agcaacacat ttaaattcag cagccggagc     180
gaaaagaatt tgcagggcgt aaatcctgat ctggtgaaag tgacccgacg ggcgctggaa     240
atctcggaag tggattttgg tatcaccgaa ggattgcgcg gtcgttatcg tcagaagcag     300
ctcgtgacca caggcaagag ccagaccatg aacagtcgcc atctcacagg gcatgccgtg     360
```

```
gatgttgtgg cttatgttgg cagccaggtg tcatgggaat ggccgctgta cgaaaaaatc      420
gcagcagcat tcagacaggc cagccgggaa ctgaatattc cggtggaatg gggcggcgac      480
tggaagaccc tgaaagacgg accacatttt cagttaccac acggagccta tccggcatga      540
agctctggcc cacgctgggt gtcgcttttc ttctgattgc cgcatgggga acatccatgc      600
gtctgtcatg gtcgcttggc cgggagaacg ccagaaacga agcacaggcc agcaccctga      660
aaagtaccgt cgacacactg aatatcatca gtgccgggt acaggatatg cagcaggtgc       720
tggcgcaact ccgcgtggaa atcaacagc gaaatcagga cggagaggcc agacgtgaac       780
agctacgcaa cgatattgca aaagatgaat gcgcccacgc tttgcctgac gctcgtttta     840
ctgacaggtt gcgcaggcac gcagaacgcg ccagggccag cgccgtcagt ccggcttata     900
ccgcagacgc tgaccatgcc ggtaacgcct cccccttcc ctgacccacc cacatgggga      960
aacctcggaa tatgggcga ccgccttctg gatgcactgg aaacctgtaa cgcggataaa      1020
cgggccattg ctgaactgga taagagaata gccgaactga cacaccagac gggagtaaca    1080
caatgaccag taagaacttt gcactgatta cagccatgac acaggctgaa ctgactcaaa    1140
aggtgaatga acatcttgcg aaagggtggc atcttcaggg ggagacgcgg gttgcctacg    1200
aacccggcac cccgtggtat ctaatgcagg caatggtggc cgatgcact acagacatct     1260 cacctgattc cccccagcac ggcagcgtgc cggagtggta ttacgtggtg gtacttgctg    1320
gtcaatccaa tgccatgtca tatggtgatg gaatgccgct gccggattct tacgatgcgc    1380
cccacccacg cattaagcaa ctggcccgtc gcaacacagt gactcccggt ggtaaagcat    1440
gcgcatttaa cgacatcatt ccggcagacc actgcctgca tgatgttcag gatatgagcg    1500
cactgaatca tccgaaggca gacctgagca aggcagta cggctgtgtc ggccagggct      1560
tacatattgc caaaaaactg cttccgtata tcccgaataa cgcggggatc ctgctggtac   1620
catgctgtcg tggtggttcg gcattcaccc agggcgcgga ggggacattc agtgcggaca    1680
cgggggccag ccaggattcg gcacgctggg gtgtgggtaa accgttatat caggacctga    1740
tcgcacgcac caaagcggca ttacagaaga acccgaaaaa tgtgttgctg gcggtgtgct    1800
ggatgcaggg cgaatttgac atgagcgctg ccacctacgc acagcaaccg gacctgttca    1860
cggccatgct gaagcagttc cgtactgacc tttccggatt taacgcgcag tgccatggcg    1920
gcagtgctgc agttgtaccg tggatttgtg gcgacacgac atattactgg aaaaacacat    1980
acggcacaca gtatgactcc gtctacggcg cgtacaaaaa cagggagagc gacaacgttt    2040
tctttgtgcc gttcatgacc gacggtaacg gcaacaacac gcccaccaac ttaccggcag    2100
aagacccgga tattgctgat gcaggttatt acggcgcgca atcccgtagt aatggtaatt    2160
gggtatcgtc aaatcgtccg acacatttca gttcatgggc gcgcagggc attatttcgg     2220 atcgcctggc aaccgctatt ctgaacgcag ttggtcgaac cagcgccttc atcagcggta    2280
ccgcaccgga gattaaaccc tcgcccggcg gcgacactcc atcggggccg tctgatggtg    2340
acacatccgt tcgtacagtc tccctgctgc cgacagccgg agaggctgct gcgcagggct    2400
ggaccatcac cggcggcagt gttgcgctgg aagatggtgt gtttaaggtt accaagcaga    2460
gcaataaaac ctggtccctg atgcatccgg tggatgacgc agtctccctg ctgacacggg    2520
gtggcagact gagctgtaag tttcgactgt caggcgcact gaccaacaac cagttcggtc    2580
tgggaattta tctgtatacc gatgtagcgt tacctgacgt cgtggcgatg accgggactg    2640
gtaacccgtt cctgatgtcg ttcttcaccc agaccacaga cggcaaactg aatctgatgc    2700
atcacaagaa agccggaaac acaaagttgg gcgagttcgg gaattacagt aacgactggc    2760
```

```
agacgctgga gctggtgttc accgccggca gtgccacggt tactccgaaa ctgaatggag    2820
tggctggccc ggcattccag gtcataaaag acagtctgac actggggctg aatgcgctga    2880
cgttaactga tatcactaaa aatgccgcgt acggcgtcga tatcggcagc ctggtgctgg    2940
aaatcaataa tcccgcagca taaggaagag caggagagca aaacagatgc ttaagacaaa    3000
cagtctgcga gagtccatgc ttcatggggtg tcggtggtgc caggctaatc ccgagaaatt    3060
caccattttc gtggagagcg gcaacattga aacgaccgga gaagcgccct cgtttgttta    3120
ccgctatcag atggtgatgt ttgtcatgga ttacgccgga gagctggacg acctcacgct    3180
gccgctgctg gcgtggttat ccgaaaatca gccacagttg ttgctcaatc cggagcgtaa    3240
tcaggacatc aaattttctg ccgttatcaa tgacgatgac agcgccgatc tcctgtttac    3300 gctcccctg cgggaacgcg ttcgcatcac gcgcagcagt cagggcacac cgcaggcaga    3360
acacctgccg gagccaaaac cccgcctgcc atcttccgaa ggcgactggt cgcatgtatt    3420
ccaggatgtg acgtggggtg aaagcgatgg ataaggcatt cacccgcgtg gatgaaacct    3480
ttgaggacat ccgcgacagc ctgaatcagc aggccatcaa taacatcgcc agaaagctgg    3540
cacaggattt acgccgcgcc cagcaggcgc gtatccggtc acagaaagcg ccggacggga    3600
ccgcgtggac accacgcaga cgccgcgtaa cccggataca ggagcgcatt cgctttatct    3660
ggaataacga agcacgcacg ctgaaaaact ggcatcacga cacggggaaa tacgggcgaa    3720
ccattaccgg gtgggatgag gataaaaaca atatccgcac gttttaccgg gatgacatcg    3780
accgctttct ggaaatacgc acccggcgca tcaaccagga cagcacaaag cgcgtcccca    3840
tgttcgtaaa actgcgcacc gcccgctacc tgaaagcccg tgcagatgct tccggtgtga    3900
cggtgggtta cagcgcgtg gccgcacgta ttgcccgcgt tcatcagttc ggtgagcgcg    3960
atcaggttgc gccgggcatt ttcaccgatt acccggtacg tgagctgttg ggcatcagtc    4020
aggcagatga acgcctgatt tataacacgg tgctgggccg gattgcggag gctgtacggt    4080
gagcgcagaa ctcatgcgac tgctgagcaa catcatccgc actgggatca tctctgaagt    4140
tgatgagaag tcctggtgcg tgcgcgttcg cagcggcgaa ctggaaacag gctggttgcg    4200
ctggaacacc acgcgcgcgg gagccttcaa tgtgtggctg ccgccatcac ccggcgaaca    4260
ggtggtaatt gcctgcattg gcggcaaccc ggaaaccgcc atgataattg gcagcctgtg    4320
gagtgatgcc aatccggccc ccggcaaaag cctgaaagaa atcgtggtca gcgcgccgga    4380
tggcgcggtg ttccgctacg acgcggacgc aggcgcactg agcgccagcg gcatgaaaac    4440
ggccaccctg caggcatccg tcagtgtgac actggacacg cccgtcgtgg aatgcacaga    4500
ccttctgaga acggcgacgc ttgacgtcac aaaaggggga agatgagcg gcaatatcac    4560 gcacagcggc ggcaatttca cctcaaacgg catcacagtg catacgcata acacggtgg    4620 cgttaaaggt ggcagcgatt cgacaggagg cccgcagtga caacccgcta cacaggaatg    4680
aacccggacg gaacgggaaa cctgaacgat atggagcatc tgaaacagtc agtcagggac    4740
atcctgacca ccccgctggc aagccgggtt atgcgacggg aatatggcag ccttgtgccc    4800
gatttaattg acgaacccat gaataacacc actcgtctgc aatgcatgag tgctgccgtg    4860
attgcgctga cacgatggga accccgcatt gccctgacg ccatcgacgt tgtctggaag    4920
gcaggaggcc gcgccggggt gacgctgtcg ggcactgtca tgcagaccat gcagaatgtt    4980
gaattaacca tcacgctgag ggagtaaatc atgcctgccg ttgacctttc ccagttaccg    5040
gaacccgcca tcatcgcgga gcctgacttt gaggcaattc tggctgacac aaaggccatg    5100
```

```
atgattgcgt cctatcctgc cgaacagcgt gaagccgtct ccgccgcgct ggagctggaa    5160 tcggaaccec tgaacgttat cgcccagaca cagcgtttc gtgaaatgct gttacgccag     5220
cgggtcaatg agggggcacg cgcctgcatg ttaagccaca gcgccgggac agacctggac    5280
aacctcgcgg gcaatatgaa cacaaagcgc ctgaccatca ctccggcaac ggataccgcc    5340
gacgcagtga tggaaagtga cacctcgctg agactgcggg cgcagcgggc gtacgatggc    5400
ctgagtgttg ctggcccgtc aggtgcatac gagtattttg cccgcagcgc cagcggtctg    5460
gtgcgtgatg cgcgggctat cagtccgtct ccggcaaatg tgacggtttc catcctgtcc    5520
actgaaggcg acggcacagc aacgaggcg ttgcttaata ccgttcgcgc cgttctgaat     5580
gcagaggata cccgcccggt ggccgaccgc cttactgtac agagcgccag aatcgtgaca    5640
tggcggctga atgcaaaact gtacttttac cccggcccgg aatccgaacc tattctggcg    5700
gcggctgaat cgtcgttcag gaagtggctg gctgagcagg gcttatcgg tcaggacgtg     5760 gcgttgtccg ccattgctgc cgcactgcat gtgcacggtg tgcaacgcgt ggagataatc    5820
gaacccacac agaatatggc catcagcgac atacaggcgg cgcgctgtga gtcgttcacc    5880
atcagcgaag gtgggcgcaa tgagtaattc actgttacca ccatcagcca gcagtttcat    5940
gcgttgtgcc gaagctgtcg gaacgcgcat tacagacatc ccggtagacc tcaacacgct    6000
gtggtcgccg acacctgccc ggtgcacct gctgccttat ctcgcctggg catttccgt      6060 tgaccgctgg gatcgcaact ggccggaaga gacaaaacga caggtgattc gtgatgcatg    6120
gctgatacac cgacacaaag ggaccatcag cgcactgcgc agggccattg agccgctggg    6180
atacctcatt cgcgtgtctg agtggtggga gttcggcgga gaaccgggaa catttaccgt    6240
tgaagtcggc acactggaca gtggcgtgac ggaggaaatg tatctggaaa tggagcggtt    6300
gattgctgat gccegtccgg tcagccgcca catgacaggg ctgaatatca ttcaggaaat    6360
tccgggggat atttttgcag cggcggcaac ttatgacggt gaagttatta ccatttatcc    6420
ggacgattaa gcatgagtac cacaaacacga aaatttaaaa ccgttatcac cgatacaggt    6480
gcccaaaaat tagctcaggc agccgcgcca gatggtaagc ctgtccgcct gactcatatg    6540
gccgtgggcg acggtggcgg cgcgttgccc acaccagaca gtaagcagac ccgtctggtg    6600
catgaggtgt ggcgacacac tgttaatcgc gtcatcctgg acgcaacaca tcagaaccgc    6660
attattgcgg agctggttat tcctccagaa acgggcggat tctggatccg ggaaattggt    6720
gtgtttgatg agcacggcga tttaatcgcg gtgggcaata ctgccgaaag ttacaagcca    6780
gccgttgccg aagggtccgg acgtgcacaa acatttcgca ccattctgac cgtatccagc    6840
actgccactg tggcgcttac cgtggataac accatggtta tggccacagt ggattacgtg    6900
aatgacaaac tgaaagaaca tgaacagtca cgacatcacc cggacgcctc gctgaccgca    6960
aaaggctttg ttcaactcag tagcgccact aacagcgatt ctgaaacgct ggctgcaacg    7020
ccgaaagcgg ttaaggcagc gtatgacatg gctaacggaa aatataccgc tcaggacgcc    7080
actacggcac aaaaagggat agtccagctc agcagtgcaa ccaacagtac atctgaaacg    7140
ctggcggcaa catcaaatgc agtaaaagct gcctatgaca atgctgaaaa acgtctgcag    7200
aaagctaaga atggtgagga tatctctgat aaagacacct ttacgaaaaa tatcggtgcc    7260
tgccgtgcat atagtgcaga gctgaatatt ggtggagata gtgaagcatg gacaactgcg    7320
cagttgattt tttggctaga gagtcagggg gcatttaacc atccttactg gatgtgcaaa    7380
ggctcatggg cttatgcaaa taataaggtc attacagata caggttgcgg aagtatttgt    7440
cttgcaggtg ctgttgtgga agttattggc acccgcggcg caatgaccat acgcattacc    7500
```

```
acaccgagta catccagcgg tgaaggcatc cctaatgctc aatttactta tattaatcat    7560
ggtgatgctt atgctcctgg ctggcgaagg gactataact ccaggaataa gccaacagca    7620
tcagagatcg gggcgttacc gtcagatggg acagcagtat cgtcagttaa tctggcttca    7680
aaaggtcggc tgaccgccct gacagataat atgcaggggg ccacaggtct ggagttatac    7740
gaggcgtata caacggata tccaacaacg tatggaaata tcattcacct gaaagggatg     7800
acagccgttg gcgaaggcga attactcatc ggctggagtg gtataagcgg tgctcatgct    7860
ccggcattta ttcgttcacg acgggatacg accgacgcaa actggtcgcc gtgggcgcag    7920
ctttacacct cggctcatcc tcctgaagag ttttatccag tcggtgcacc gattccgtgg    7980
ccatcagata ccgttccgtc tggttatgcc ctgatgcagg ggcagacttt tgacaaatct    8040
gcatacccga aacttgcagt cgcttatccg tcaggcgtga tccctgatat gcgtggctgg    8100
actatcaagg gcaaacctgc cagtggtcgt gccgtattgt ctcaggaaca ggacggcatt    8160
aaatcgcaca cccacagcgc cagcgcatcc agtactgatt tggggacgaa aaccacatcg    8220
tcgtttgatt acggtactaa aacgaccagt tcatttgatt acggcacaaa aactacgaat    8280
agcgctggaa atcattcaca caatataccc gttggtcaca ctggcgcggg gaatggtgta    8340
tcagccggtt ttaacgctgc gttaggtact ggtaccacgt cgagcgcagg cgggcatgct    8400
cacaatgtat atatcggtgc ccataaccac actatcggca ttggtgctca tgcccattct    8460
gtcattattg gtccccacgg acacaccatc accgttaacg ctacgggtaa cgaagaaaac    8520
accgtaaaaa acatcgcatt taactatatt gtgaggcttg cataatgaca ttcagaatga    8580
gtgaacaatc acggaccata aaaatttata atctactggc tggaaccaat gagtttattg    8640
gtgaaggtga tgcatacatt ccacctcata caggtctgcc tgcaaacagt accgatattg    8700
ccccgccaga tattccggct ggcttcgtgg ccgttttcaa cagtgatgag gcatcgtgga    8760
atctcgttga agaccatcgg ggaaaaaccg tctatgacgt ggcttccggc gacgcgttat    8820
ttatttctga acttggccca ttaccggaaa atgtcacctg gttatccccg gaaggggagt    8880
ttcagaagtg gaacggcaca gcctgggtga agatgcaga agcagaaaaa ctgttccgga    8940
tccggaaggc ggaagaaaca aaaaacagcc tgatgcagat ggccagtgag catattgcgc    9000
cacttcagga tgccgtagat ttggatattg cgacggagga agaggcatcg ttactgactg    9060
catgaaagac atatcgggta ttgttgaatc gtgttgatac aacagtagca tcggatgttg    9120
agtggccagt cgccccgcaa taaaaggata aagccatcga tagaaatatt gatggcttca    9180
tgtactctat ttatacaata caacaccgct cttttttgtt atatatgtgc agttcgatgg    9240
tatatcttta tttataaaag acattgcacc tattttttaca ttatccccaa ttttacgtga    9300
taatccaatg atgcaacaat tggctccgat atcaacgtta ttaccaattt ttactcttga    9360
accaggcatg tcaccatcta tctgtccaat ggtagtattc tgtcgtaaca ccagatttc     9420 accagcatca acagcaaaat gaacaacaat tccagcatga tggggaattg ttaacccttt    9480
tccaatattt gcgcccaatc caatttcaca accaaatttg ttaattattt taccgtttaa    9540 cttttttggct gctttcttat gtaatttatt accattaata tacatttcgt tagccaaccg    9600
ccaccagaaa aggaaattcc ggttacgctg ttttttctct cttaaaagcc tccagatatc    9660
catacgtttc cgccgaatta cttcatattt ccagaagttt tttaaattag tagagtcccc    9720
aaataaaaca aagtgaattg ccattaagta agacagcacg ataatctcct taattattat    9780
ttcagaccac acatattata aggttaagag attataaaat cctgttgttt attattcaaa    9840
```

```
aacaattttc tgagaaggac atacaacagc aagtcgccag tcaccttcat caggaaattg    9900
gcgacatacg ttaaatcaga gcagcccctt aactgagctg gccgcgctat aagggatga    9960
tgtcacctta tctttgaagc cggacaacat atcgctgaac gatgaggatt gcaggcgctc   10020
ccgcaaatcc tcatcacagc gttcaagagt cagtgaaaat tctatctttt tcgccttacc   10080
gtagcgatca aactcggaac gggtcgtatt cgtttcagtc agtacataca tgccgtaaat   10140
ctgcccgaca ccatcaatca gaggccaggg ccgtcctgta tatgcctgcg tggtcagcaa   10200
tgaaagcgac acttcgccac ctgtaatttc aggataaagc acgccggaaa gcacaatgcg   10260
atcatcacct gcaccgatat actgccagct tgctgaacgg ttaacgcgtt cattttcac    10320
atgccgccag cttttgtttt gctgtaactg ctgatgcggc aatgtgcgca gctcaaaaac   10380
aaacatgccg tagatcatca tcatgaccat gactcctcaa tctttatcgt aaaaactgcc   10440
acgtccggca cgggcgcgcc gttccatctc tgccctgacc atttcaccga ccagtttcgc   10500
cagttcgcgg ggattctgcg taacaacgtt atgcagatga acatgaattt caccgcaaaa   10560
tccggagaca gcaggctccc ggttacggga agttgcagga actgatgcca ctggcgatcg   10620
tatggcctcc gccaccgggc gggagctggc cgcaacaaca gggaccagcg ccggaggcag   10680
cggagccgag accacgggtg tgatattaat tgcggggca ggcttactga cctgcgcaat    10740
cttccgctcc tgccactccc cacgaacagc aagtgcgcgg ggcaggttct taaagacaat   10800
atcgccgggg ccaatgcgtt ttttcgtctc atcaaccagc ttacctgtgt tatcagcaat   10860
tttgctgagt ctgcgtagcg tcccggtatt gctgtctgtg agcggtttgt tgtctttggg   10920
tttatcacct ccggtgccat tgccattttc cacaggcttc ggcggattga ttttcgccag   10980
gtcccctga agcaaggcaa ccttgtcctg aagaatggcc gcacgctgtg cgtcttcgat     11040
tttcttgcgc gccttttccg cttcatccgg aaggacacca agtttttcaa gtatccacgc   11100
cagcgtatcc agtagcattt ttgcaggtgt cagaacaagt tgtaacgcac cgccaagaac   11160
gttaccgaat acctcgccag cactggtgca tttatccagc gtttccttgc tggactccat   11220
cggtgacaac agcgatttaa accagttaaa caccaggctg atcccgcttc cgattgcgtc   11280
aaaaacaggg ccaaaccgtt caaggtttc acgcaacggg gtcagccttt ccataatccc    11340
gctgaacacc ccggcaaaaa atgccctgat gggatcccag tatttccaga taagaacggc   11400
agctccggca agcgcagcca cgataagacc aaccggactg aacagcgccc cgatagcgcc   11460
acccagcaaa gaaacagaac ccgtcaccat tccccacagc gcaggcaaca ccctgatgac   11520
attcattgac cgggtaagaa tgtcgaaacc aagacgcaag gtggccagct tcccgtaaag   11580
cacccccaata accagcgaca acgagccaat cgttgcagtc attgccagca acgcaccgcc   11640
tgctatcagt agctggcgcg tcagtaccgg atgggcctgc gccagcgagg tgatttttc     11700
aagcacccgc gtgagccact gcgtgacaga acgcagcgga ccgtcaacca gatcactgat   11760
gcgaatacga agaccttccc atgcgctgtc gagatttttc aggtctccat caaggttatc   11820
ggccattact tttgcaacgc gatcggcctc tcccccttgcc cctgcaatt ctctggtcag    11880
tttttgcagt tctcctgaac cagccgccgc aacaagcgtc tgcaaaccaa cgaacgcctc   11940
ttctccggcg atgtccttga agaaggagac ctggtccacc tgcccgtatt tttgtgtcgc   12000
cttatagaga tcaagcagca catcctccat cgggcgcatt ttgcctctgg cgtcagcaac   12060
tgacaccccc agctcttttca gtgcatcagc cgcagctttt ggcggtgatg caaggcggga   12120
cagacttgcg cgcatggccg taccagcatc gcttccgcga agaccattat tggcaagcat   12180
cccggccatg gccgccgctt cttcaagact gataccaagt tttgcggcaa ccggaccggt   12240
```

```
atacttcatg gtttcgccca gcgcgcgtaa atcagtattg gtccgggtga atgctgctgt   12300
cagcgtatcg ccaacccggt ccatttgatc ggctgtcagg ttgaactgtg tgaggatatt   12360
ggagcctata tcagccgtct cgccgagttc gacgccacct gccagcgcca tattaagaac   12420
accgggcaat gcggcctgaa tggcctgcgg agtaaaacca gccattgcca gaaagctctg   12480
cccactggcg gcatcactcg cagtaaactg tgtttcagaa ccaagtttta acgcctgctc   12540
acgcagcgcc ttaaactgcg ggctgttttt gtcgattcgc gtcagtgcct gaacgcggga   12600
catctctttg ccgaacccga tcgcaggctg caaaaaacgc ccggcagcat agccgccagc   12660
cgctgcagca ccaattgcca gcgcaccacc tgttttcagt tttcccgcgg tttcctgcgc   12720
gcgcgaatac cgctcacgcg cccgcgttac acgcgcaagc gcctgccgtt cgcgttcaag   12780
ctggttgttg tactgttcgg tgcgtctgat ggcctgctgg atggtgttat cgctgcctgt   12840
cagggaaatg ccgtggcgtt tcagctctcc gccaagttcc gcatttttct gaatttcccg   12900
tgtgcgcgat tcattcaggc gttcaagccg ggtgcttaac tgctgcatca gcttttgttg   12960
tttttcgctg agcactgtac ccgtgcgttg taactgatta agggcgttaa gctggcgtcg   13020
tgctttcacg ataccgcat ccgctttcct gacagcgtcg cgggcgcgct caaatgaacg   13080
cgcctgacgc tcgagatttt tgatcgcccc ctgcgttcgc tggatggagt caccaaactg   13140
ccccatcagg cggcgggcgt tttcggcagg ccgggtcagc ctgtcaacgg cgctgaaagc   13200
gacccggata tcaagagtct tcattgtctg cactcccgct gcgaagtgcc gcccgctcac   13260
gccagctaac cacttcgccg ggcgtcatca tgaagatttc ggcgggcgac cagttaaaaa   13320
taacggcaat atctgccaca aagtcttcta tgtgctcaaa gcacacaacc gtgatcaggc   13380
ttccgtcgcc tgttcgttct tcccgccaga gtccgcaccg ctcaaaaaat ttacggcaac   13440
cgcacataac tgaataaagt cacgggatgc catttttttg atcgtcactt catccagtcg   13500
cggtgatgtc acgcgtgaca gcagcgtaaa catggattcc gctttcagat tcagcacatc   13560
agacagcgac aaatctcgca gagatccagc ctgctcaata gctccggtga tctccacata   13620
cgtgattttt tcgccgcctc gctcaattgg ttgggtaagt tttacgccac gctcactggt   13680
ttctttcaca gtgtcagcaa cgaccgtgtt ttcggtatcg atgttttcg tctctttcat   13740 caggaaactc ctttcagtca gaggcgacgc actgcgccgc ctgcatatta cttatcagcc   13800
aagcccaagc gcggaacgga tgcgatcggg cacaatgtcc ttgccgtcct tccggtaaat   13860
gaagttcagc aggtcaatct cccacaacgg gcgatcgtta acactcagct tgtagtaggt   13920 gttttttaatg gcgtaagtgt gtgatgtggc ttcgccctgt ttggcttccc ccatatcaat   13980
ttccgtcaca cgtccgcgca tctcgatttc atacagatcg cttctgcat cggtgtagta   14040 ttcacccgca aaacgcagca gcgtgccgtc aatcgtgccg ccatatttaa ggaacagcgc   14100
acgaacagct cccccccataa caaaactcgc atcaagcgcg gagtcgtcca gaccgagatc   14160
aatacttacc gccccccatca tgccaccacc acgatagctg tcggttttgc gcgtcagttt   14220
aggcagggta acggacgtca ccttacccac ttcgttttca ccatccacaa acagcgtaaa   14280
aaagcgaaga tgttttggta cagccatcag acacctccca gcaccgcaaa tgcgggacca   14340
aagaattcat cagtaaacga ctggtaaagc tccatgtctt ccagcggggg aacaggcgta   14400
tatttgtagc gaatacgcac gcgcccctga cgtaaattcg tggtgccgtt atccaccacg   14460
tcataccagc acgacgcccc aatcagtttc ccggcagtaa ccagtgaatc cagttttgcc   14520
ctgatggcac tgataacatc tttcacgttc gcaggcgtca gtggactgtc gatggtttca   14580
```

```
aactgcgctt ccgcaattga atcagccagc acctgtgcgg ttcgggtata cacctcaaag    14640
atgtaggcgt tcgtttccgg tgtgcggttg ccccagaagc ggaacccgtt gcgacgaata    14700
atggtcgtga tttctttgtt gttgaggcta ttggcatcgc tgtcttcggc ctgcaacgac    14760
cagaacacat gcctggacat ccccagcaca tttttaaccg gaacgttgga cagtgatttg    14820
tgccatccct gctcatggtc aatgtacgca cgaaggccgc acgcataggc aggcgcgggg    14880
aacgtttcgt ttttgccact tttcgggttg taggcgatga agtccggcca taagagcatc    14940
acctcacgtt cgttgaattt ctggcggtag gtaatcgcct cagccatcgt gttacagccg    15000
tgacatgagg catacacaaa cgcgcgcagt ttacccgcaa tcacgcacag ggattttgtc    15060
accgcctccg tgtccagctc cggcgcggcc agaatacgcg gacggtatcc gatgctttca    15120
tcctgctctg caacaagcag cgcatacatc cccgtatagc tgccgtcaga ttcagaacca    15180
ccgataacca gttgatcctg cgtctttccg tcttcttctt tgtgttcagc cacgcgaacg    15240
acgatcacct ttgtgctcac ctggtctgcg atggccttaa gcgcacgata aagcgtcccc    15300
gttgttccgc atttcccag cacgtcatta acgcgggtca gcagtgtggg cttgttcagc    15360
gggaacagct tcgcgtccgc atcatccgcc gttgccacga taccgataac gctggaatca    15420
acatcgttaa tcgctgttac caggtcggta ttttccgtaa cacgggcacc atgaaaacga    15480
gtttcactca tagcttcagc cccttgtatc cgttaaatga ttcggcaaca atcatcaccc    15540
accacgcgcg taatctcacc cctgcgccgt tctcccacca cggcgacaac aaaaagcagt    15600
aaccccctcc gcacgcacat gcgaccatgc cgcacaggga gggaacagat gaccgacacc    15660
accatgcaat tgctcagtca gggcacagac cccgtgaaaa tgccggattt tgatattctc    15720
gcggagggta aaacgctgtc aggcgtggca gagcgcctga tgagcctgtc actgaccgac    15780
aaccggggat ttgaggcgga ccagctcacc atcacgctgg atgatgctga tggtcagttg    15840
cagctaccgc cacggggcgc gcgcctgacg gttctcattg gctggaaagg agaaccgctg    15900
acagaaaaag gcacttacat tgttgatgaa atcgctcacg aaggaccgcc ggacaggctg    15960
actgtttcag ccagaagcgc agattttcgg gatgaattta acgttaaacg tgaggtgtcc    16020
tggcatgatg tgaccgttga gcgcgtggta tccgccatcg ctcatcggta tggtctgaaa    16080
ccgcaaatca gcgaaatgct gatggatatc gaaatcgacc acgccgacca gaccgaagaa    16140
agcgatatgt ccttccttac gcgcatggcg gaaatgctgg gcgcaatcac cacggtaaaa    16200
agcggcaatc tgttattcat catgccaggt ggtggcgtga acgcacaggg ccagccgttg    16260
ccatcgttcg ccatcacacg cagcagcggc gatcgccatc agttccgcat tgctgaccgc    16320
gaggcgtata cgggggtacg cgcttactgg cttgatctta attacgggaa aaagaaaaaa    16380
gtcagcgtga aacgccgcaa accgccaaaa cccaaaaagg agaaaagcag cagccgtgaa    16440
ggtgattata tggaaggcgc ggaaggcaat gtgtttgtgt tacgcaagac ttatcagaac    16500
gagcaggcag caagacgcgc agcggcggca aagtggcagc agctacaacg cggagccgca    16560
tcattttcca tcacgctggc gcgtggacgt gcagaactct accccgaaat gcatggcacg    16620
gtaacaggat ttaaaagcga gattgataat caggactgga ttattgcaaa agccgagcac    16680
accattgata cacgcggctt taccacgcag cttgagcttg aggcaaaaat cccggaatgg    16740
atagcagaaa cagcgtgaat gtcttaaatg tattagttca gatatgtact agcaataaac    16800
atagttagaa aggccgctaa cgcggccata ttaattaaaa ctccagttac taatattgag    16860
aaagataatc agcgactcca tctgcagggt ttcgcccacc agtataaatt gtgcctaatt    16920
cttgaggtgt aacatatgtt gtaggccaaa tggccatatt tttaaaatag ttatctattt    16980
```

```
ttattctttg aagttcttta aagagataat cttctaagtc atttcttttt agacagttaa    17040
cataataagc agccgcactt gctactatat ctacaatttg taattgagga tactcttgtg    17100
atgaatggaa tgtcaaagaa cgagctttaa ttggcaattc aaattttctt cgatcataac    17160
catatgcctc cgtaatttttt gatatatcca taaatttatc aaaaatatct ttcttctctg   17220
taatagcttt ggaatcgtca tgcttaatat aaaaaccatt agggtataat ttaccccatt    17280
ctacacagtg tctaaagagg cttggtatag atggatctaa tgtgcttttc tcaacacctt    17340
ccaatatatc atcaatatcg cttctggtaa tactaattct gtttattata tctgtgaata    17400
tcttatcact tgagcatatc tttaactcat caattaccct gtaaaattca tcaattgact    17460
cagtcgattg gcttctgatc atattcataa acactgata cattacctct gttttttcct     17520
ccccacagaa agcagggaaa cagaaatagt aaacattaga cagagctaga ttctgtccat    17580
ttatataaag atctattcct ctattagagc accacgtctc gatcaaaata tcaacaatct    17640
ttgctgttag catgtatttt ttatcgacca agtatatttt aacattctct tcattgacat    17700
atttgctttc aagaagccta atgatgccat cctgaccaga ttttctacgt ctaagagttt    17760
taaagtgggc ttctgttgga gacttgcttc cggttagttc taatgcctta agcgcatcct    17820
gtttactaat actacttgaa cttaaggtaa aaacaggttg caatggatcg agtaaatttc    17880
cgccagtatt acctgattca tcaaaaaata tatcaggctt tatatacaac attttattta    17940
tctttgccgc taagtttctt tttttctcat tttctcgctt aattttatta tctcgcctac    18000
gttgactatt ctttcccata aatacctcac aatctgaatt agatatccca atttaacgca    18060
ttaataacat aatgttatga tatcacacaa tcaaaataac gtgctgattt taatgtatca    18120
ggtttgacta gctattcttt gataagcgaa taataagaat gtcagcccct caactcaaag    18180
cggtttagtc agttggaatc ggagctaagg aaggtgcgaa caagttcctg atatgagatc    18240
atcatattca tccggagcgc atcccagagg gacatcatga gccatcaact caccttcgcc    18300
gatagtgaat tcagcactaa gcgccgtcag acccgaaaag agattttcct ctcccgcatg    18360
gagcagattc tgccatggca gaatatgacc gctgtcatcg agccgtttta tcccaaggcg    18420
ggcaatggcc gacggcccta tccgctggag accatgctgc gtattcactg catgcagcat    18480
tggtacaacc tgagcgacgg tgccatggaa gatgccctgt acgaaatcgc ctccatgcgc    18540
ctgtttgccc gattatccct ggatagcgcc ctgccggatc gcaccaccat catgaatttc    18600
cgccacctgc tcgagcagca tcaactggcc cgtcaattgt tcaagaccat caatcgctgg    18660
ctggccgaag caggcgtcat gatgacccaa ggcactttgg tggatgccac catcattgag    18720
gcacccagct ctaccaagaa caaagagcag caacgcgatc cggagatgca tcagaccaag    18780
aaaggcaatc agtggcactt tggcatgaag gccacattg tgtcgatgc caagagtggc     18840
ctgacccaca gcctagtcac caccgcggcc aacgagcatg acctcaatca gttgggtaat    18900
ctgcttcatg gagaggagca atttgtctca gccgatgccg gctaccaagg agcgccacag    18960
cgcgaggagc tggccgaggt ggatgtggac tggctgatcg ccgagcgtcc cggcaaggta    19020
aaaaccttga agcagcatcc gcgcaagaac aaaaacggcc atcaacatcg aatacatgaa    19080
agccagcatc cgtgccaagg tagagcctcc cgtttcgcat catcaagcgg cagttcggct    19140
tcgtgaaagc cagatacaag gggctgctga aaaacgataa ccaactggcg atgttattca    19200
ccctggccaa cctgtttcgg gtggaccaaa tgatacgtct gtgggagaga tctcactaaa    19260
aactggggat aacgccttaa atggcgaaga aacggtctaa ataggctgat tcaaggcatt    19320
```

```
tacgggagaa aaaatcggct caaacatgaa gaaatgaaat gactgagtca gccgagaaga   19380
atttccccgc ttattcgcac cttccctagt agaacttaaa ataacagaag caccacgtta   19440
agggaggtct ctatgttccg ttgtccgctt tgtggcgcat ctgcccgtat ccgcacaagt   19500
cgtccggaaa atgattcaaa caccgtgcgg caaaagtatt accagtgtaa caacctggaa   19560
tgcggcgtat gcttctcaac actggaagcc ttccataaat tcacatcaaa acacgcctcc   19620
gccgttcact cttcagaagg tatcccgtgg catgagctgc cagcttcaca caggggaaac   19680
aatcagatga gtttgccttt acctcagaac taacaggcag aattgccgga ttaacaaaaa   19740
agcgatagat tacgcgcggg tgcctttcgg ctgatggtcg gagggaatac ccgaaggcca   19800
gatgtggaaa ggccccggaa aacatctctg tttaaccgag gccctaaccg cattaccttg   19860
acaagtgaaa ggttagcgcc tctccggaaa aggagcaagt gctatgtcgc aaaaatcgct   19920
tacggccatc acgttctgcg tgacggcaat cctcatcatc tggatgctgc acggttcact   19980
gtgcgaaata cggatgagct tctggggagc ggagtttgcg gcgttcttac agtgtaagca   20040
gtaaggaaac cgcgacgggg gagcaatccc ccgtcaatcg gttgccaggg taaggtcgat   20100
aaggcactct atctcacaga catgaaacaa acccgcagca taaaaactgc gggttttctt   20160
tttggtgtcc tcaccgactt gaaacagtga tcagactata agacaaagcc cacaatgtag   20220
cgggcttact cccctccccc cactaaatgt ggacacatcg tggaacgaag agatataaaa   20280
cattataaat caattggtta ttgaaagaaa aaaggccgct aagcggcctt tttagttaga   20340
tcagattact cgtctttggg cgaagcgttt tcgacccggc ttttaactt ctgcccgggt   20400
ctgaaggtca ccacgcgccg tgctgtaatg ggaatatcct cgcccgtttt cgggttacgt   20460
cccgggcgtt gattcttatc acgcagatcg aagttaccaa aaccagagag tttcacctgt   20520
tcgccgtttt ccagagcgcg acggatctct tcgaaaaaca gttcaaccag ttctttggca   20580
tcccgcttgc taagcccaag cttatcaaac agatattctg acatttcagc ttttgtaagc   20640
gccataggtt caatccctca atgatgcctg gaatcgctct tttaatgcct ctacacattt   20700
ggcgacggta gcggcaatct cctcttcttc gagtgtacgg ctggtatctt gcaggatcag   20760
gcttatggcg aggctcttat accctccgc aacacccta ccgcggtaca cgtcaaataa   20820
gtttacgcca actacctgat ttacgccaac tttcttacat tcggataaaa tatccgctgc   20880
gggaacgttt tctgcgacca ccaccgcgat gtcacgacgg ttcgccggga agcgagaaat   20940
ctcgcgcgcc tgaggcacca cgcggtctgc gagcttgttc cactccagtt cgaacaccag   21000
agtgcgaccg ttaagatcca gtttacgttc cagttcagga tgaacaaccc caacaaaacc   21060
aatacgttca cctttcagat aaatcgctgc ggattgcccc ggatgcagtg ccggattcgc   21120
ttctgcacgg aactcaacct cattcagttt accggtcagg tcgagaacgg attcaagatc   21180
gcctttcaaa tcatagaaat caacggtctc ttttgccagg ttccagtgct cttcgtaacg   21240
gttaccgcaa atcacaccgg ctaacatcag atcctgacga atgcccaacg gtgcctgagt   21300
atctggtacg aaacgcagac cgctttcgaa aatgcgcaca cggttctgct gacgttctg   21360
gttgtacacc acggttgcca gcaggccggt ccacagagaa agacgcattg ctgacatttc   21420
aacagagatc gggcttggca gcagtaaggc ttcaacgcct ggatggatca tctgctgcac   21480
tttcggatca acgaagctgt aggtgatcac ttcctgatag cctttgtcgt tgagcagcgt   21540
tttcacgcgc ttgagcgaca ggtcagcttc acggtgagta cccataatca ggcttgcctg   21600
taccggctca tccgggatgt tgttgtagcc gtaaacacgc gcgacttctt cgaccagatc   21660
ttcttcaatc tccatatcga aacgccagct cggcgcaact gcctgccact cgtctttgcc   21720
```

```
ttcggtcact tcgcagccga gacgacgcag aatgtcagtt acctgctcat ccgcaatatg   21780
atggccgatc aggcgatcca gtttgctacg acgtaaagtg atggttgcac gcttcggcag   21840
cgttgcttcg ttggtgatat caattaccgg accagcctca ccaccgcaga tgtcgatcag   21900
cagacgggtc gcacgttcca tcgctttgtg ctgcagtgcc ggatcaacgc cacgctcata   21960
acggtgagac gcatcagtat gcaggccatg acgacgagca cgaccggtga tagacagcgg   22020
gctgaagaaa gcgcattcca gcaagacgtt ttgcgtttcg tcattcacgc cagagtgttc   22080
gccaccaaag atgccgccca tcgccagcgc cttgttgtgg tcggcgatga ccagagtgtc   22140
agcattcagc ttcgcttcag tgccatcaag cagtaccaac gtttcgccct ctttcgccat   22200
ccgcaccaca atgccgcctt caatgcgatc tttatcgaaa gcgtgcatcg gctggcccag   22260
ttcgagcagt acatagttgg tgacgtcaac aactgcatcg atagaacgga tcccgcaacg   22320
acgcagtttt tctttcatcc acagcggagt tggcgcttta acgttaatgc cttttaccac   22380
acggccaaga taacgcgggc aggcttccgg cgcttcgact gtaatcggca gcgtgtcgtc   22440
gatggtcgca ccaaccggaa cgatttccgg ttcaaccagc ggcagctgat tcagcacggc   22500
aacgtcacgc gcaacaccaa tgatacctaa acagtcggca cggtttggcg tcacgctgat   22560
ttcgatggtg ttgtcatcaa gtttcaggta ttcacggatg tcggtgccaa tcggcgcatc   22620
cgcaggcagc tcgataatgc cgctatgatc gtcagaaatt cccagctcag aaaaggagca   22680
cagcatccct tctgacggtt caccacgcag tttcgccgct ttaattttga aatcacccgg   22740
cagaacagca ccaatggtag ctaccgccac acgcaggccc tgacggcagt ttggcgcacc   22800
gcagacgatg tccagcaggc gatcgccgcc aacattcact tttgtcacac gcagtttgtc   22860
agcgttcgga tgctgcgcac actcaaccac ttcaccaacg accacgccgt ggaagctacc   22920
ggcaaccggt tctacaccgt caacttccag gcccgccata gtgatttgat tcgccagcgc   22980
atcgctatca atcgccgggt tcacccattc gcgtaaccac agttcactga atttcataat   23040
ctattcctgc cttatttaaa ctgtttgagg aaacgcagat cgttttcgaa gaatgaacgc   23100
aggtcggtga cgccgtaacg caacatagtc agacgctcca tccccatccc gaaggcgaaa   23160
ccagagtaaa cttccgggtc gatgccaacg ttacgcagca cgttcggatg caccatcccg   23220
cagcccagca cttccagcca tttaccgttt ttacccatga catccacttc tgcagaaggt   23280
tcggtaaacg ggaagtagga aggacggaag cgaatctgca aatcttcctc aaagaagtta   23340
cgcaggaagt cgtgcagcgt gcctttcagg ttggtaaagc tgatgttggt atcaacaatc   23400
agaccttcca tctgatggaa catcggcgtg tgagtctggt cgtagtcgtt acgataaaca   23460
cggccaggcg cgatgatacg aatcggtggc tgctgggctt tcatggtgcg gatctgtacg   23520
ccagaggtct gggtacgcag caggcgggta gcgtcaaacc agaaagtgtc gtggtcagcg   23580
cgcgccgggt ggtgaccagg aatgttcaga gcatcgaagt tatgataatc gtcttcgatt   23640
tccgccccgg ttgccacggt aaagccaagc tcaccgaaga aactttcgat acggtcgatg   23700
gtacgggtaa ccggatgcag accgccgttt tcaatgcgac gacctggcag agagacatca   23760
atcgtttccg ccgccagacg cgcattcagt gcagcgcttt ccagttccgc tttacgcgca   23820
ttcagcgcct gctgaacctg ctctttcgct tcgttgataa ccgcaccagc tgccggacgc   23880
tcttctggcg gcagctcacg cagggtcgtc atctgaaggg ttaagtgccc ttttttaccc   23940
aaatattcga cgcgcacatt atctaacgcg gcaacatctg acgcctggct aatgccgcc   24000 ttcgcactgg caaccagttc tgcgagatgt gacatggttt tcctcattgt gtcagtggtg   24060
```

```
acactggttc gttggactta gagcctatcc catcaggcta ttttacttgc cattttggtc    24120
ccgggcagtg ctcgaaatcc tcacgtactt aattacgctc cggtttctcc gcgctggccg    24180
tgtccagact ggctgcgaca attacgcctg atagactggc ttttattttt tcaaaacgcg    24240
catacaaaaa aagcctccac tgggaggctt caggcgctg ttttccgttt ctcttctcac     24300
gcgctagcct cctggattca ggtgctaaag taaaaaagaa gcggaaaata gcagcattca    24360
ttgcttgcgt tacctttggg tactcttcaa aagacctta ttgaaaaggc tacgcgata     24420
aaagtcaatg ttttgatggc gttgaaacga aagagggag actagctccc tctttcaact    24480
ggcttatgcc agagctgctt tcgcttttc aaccagagcg gtgaacgcta ctttgtcgaa    24540
tactgcgata tcagccagga tcttacggtc gatttcaaca gaggcttttt tcaggccatt    24600
gatgaatttg ctgtaagaaa taccgttctg acgtgctgct gcgttgatac gcgcaatcca    24660
cagttgacgg aactgacgct tacgttgacg acggtcacgg taagcatact gaccagcttt    24720
gataacagcc tggaaggcaa cgcggtatac gcgagaacgc gcaccgtagt agcctttagc    24780
ttgtttcaaa attttcttgt gacgtgcgcg tgcaataaca ccacgttta cgcgagccat     24840
atgtgctctc ctgtatctat attctaatta aaaagttaaa aacgttaacg cttatgcgt    24900
acggcaggca cgcgattacc aggcccagat cgccttgga aaccatggct ttcggacgca    24960
ggtgacgttt acgtttggtc gcttttttgg tcagaatgtg acgcaggtta gcgtgcttgt    25020
gcttaaaacc cctttaccg gttttttga gcgcttagc agcaccgcgt acggtcttaa      25080
tttttggcat tttaataact tccacttcgc attgttaata aacgaaacaa aggcgaacaa    25140
tgcctgtgaa gcccgaaggc tccacagaca gtgctacttg aaggccttac tgtttcttct    25200
taggagcgag caccatgatc atctggcggc cttcgatctt cgttgggaag gattcgacca    25260
ccgccagttc ttgcaaatcg tctttcacgc gattaagcac ttccataccg atttgctggt    25320
gcgccatctc acgaccgcgg aaacgcagcg tgattttggc tttatcaccc tcttcgagaa    25380
agcgaatcag gctgcggagt tttacctgat agtcgcctc atctgtacca ggacggaatt     25440
taatttcctt aacctggata acttttgct ttttcttctg ttccttagaa gacttgctct     25500
tttcatagag gaatttgccg taatccatta tacgacaaac cggcggctcg gcgttagggc    25560
tgatctcgac taagtctact ccggcttctt ctgctttctc cagagcttct ctcagactca    25620
caataccaag ctgctcgcct tccagacctg ttaagcgaac ttcctgggcg cgaatttcgc    25680
cattgatacg gttagggcgc gccgtttgaa ctcgttttcc gcctttaata ccttattcct    25740
ccaattgttt aagactgcgg ctgcgaatct cttgttgcaa cttctcgatc acttcattta    25800
cgtccatgct tcccaggtct ttaccacggc gggtgcgaac ggcaactttg cctgattcca    25860
cctctttatc accacagacc agcatatatg ggacgcgacg caaagtgtgc tcgcggattt    25920
taaagccaat cttctcattt ctcaagtctg ctttaacacg aatgcccgca tttgatagtt    25980
tttgcgtcaa ttcgttaacg taatcagact gtgaatcggt aatattcatg ataacaacct    26040
gaaccggcgc aagccaggtc gggaagaaac cagcgaattc ttcggtcagg ataccgatga    26100
aacgttccat cgacccaaga attgcgcggt gaatcattac cggtacctta cgctcgttgt    26160
cttcgcctac ataagaagcg ctcagacgag aaggcaaaga gaagtccagc tgtactgtac    26220
cgcactgcca tgcacgatcg aggcagtcat acagggtaaa ttcaattttc ggaccgtaga    26280
aagcgccttc acccagttga tattcaaacg ggatgttgtt ttcttccagc gcaaccgcca    26340
ggtccgcctc agcacgatcc cacatttcgt cgctgccaat acgttttca ggacgagtgg     26400
agagtttgac gacgatcttc tcgaagccaa aagtgctgta catatcatag actaaacgga    26460
```

```
tacatccgtt aacttcatcg cgaatttgtt cttcagtaca gaagatatgc gcgtcatcct   26520
gggtaaatcc acgcacgcgc atcaggccat gcagcgaacc tgacggctca ttacggtggc   26580
agctaccaaa ctcggccata cgcagcggca gatcgcgata agacttcagc ccctggttga   26640
aaatttgtac gtgacccggg cagttcatcg gcttaatgca gtattcacgg ttctcagaag   26700
acgtggtgaa cattgcatct ttgtagttgt cccagtgacc ggttttttcc cacaggacac   26760
ggtccatcat gaacggacct ttaacttcct gatactggta ctctttcagt ttagaacgaa   26820
caaacacttc tagttcacgg aagatggtcc agccgtcgtt gtgccagaat accatacccg   26880
gcgcttcttc ctgcatatgg tacaggtcga gctgtttacc gatttacgg tggtcgcgtt   26940 tcgcggcttc ttccaggcgc tgcaggtaag cgttaagcgc ttttttgtct gcccacgccg   27000
taccgtaaat acgttgcaac attttgttgt tgctgtcgcc acgccagtaa gcccctgccg   27060
ttttcattag tttgaaatga tggcagaaac gcatgttcgg tacgtgcgga ccgcggcaca   27120
tatcgacata ttcttcatgg aagtacagac ctggcttgtc atcatgggcg atgttttcgt   27180
caagaatgga gactttgtag ctctccccac ggttggcgaa agtttcacgc gcttcgtgcc   27240
agctgacttt cttcttaatg acgtcgtagt ttttctcagc aagctcatgc atccgcttct   27300
cgagtgcttc gacatcttcc tgggttaacg tgcggtcaag atcaacgtcg taataaaaac   27360
cgttgtcaat aaccgggccg attgccattt tggtatgcgg ccaaagttgt ttaatcgcgt   27420
gccctaacag gtgcgcacag gagtgacgaa tgatctccag accgtcttcg tctttggcgg   27480
taatgatgga cagttgtgcg tcgttttcaa tcagatcgca agcatcaacc agttcgccat   27540
taacgcgccc tgcgatacag gctttcgcca gacctggacc aatgtccagc gcaacatcca   27600
tggggcttac agcgtggtcg taatggcgtt ggctgccatc aggaagagtt ataacaggca   27660
ttttatatcc ttatttgcag tggtgaccca cacgaaagat cacatacaaa gaaaaatttg   27720
tttattaaca gttcattgcg aaaccatcta gccaacaaat gctaaattgg ttcgcaatca   27780
ggtacacaaa tgaaagacat taacctctca ccttccaccc ggttgagcga tgttaacact   27840
aaaaaaaggg agattgtacc tttccgtttc acattgattc gattcgcaat tcgtttgtag   27900
tgagtacacc agcaaaacgc ttaaagaacc actgataaca tcacggtgcg tctgaaaggt   27960
ttactgcgag cggatttaca gcagcataaa ctgaatccag caaagttcgt tgcgtgattt   28020
ggcggtagta ttttaaacgc tcatgagatt aatgacaaag tggtcatatc acaatgataa   28080
aagtgacaca attcttataa caattttcg tgcacatttc gttctggcga taataattaa   28140
tcatcatcct caaaacctcc agatatatat aaggcgaata gattatgagt caaaacgata   28200
tcattatcag aactcattat aagtctcctc atagattgca catcgatagc gacataccaa   28260
caccttcatc agaacctatt aataaatttg cgcgccagct catcacccta cttgatacct   28320
ctgacttaag ttcgatgctg tcatactgtg ttattcagga atttaccgca aactgtcgaa   28380
aaatatcaca aaattgttat tccactgccc tttttaccat taactttgcc acttcaccca   28440
tccatgcaga aaatatactc attacattac actataaaaa agatttcatt tccttattac   28500
tggaaaccac gcctattaaa gctaaccatt tgcgaagcat actggattat attgaacagg   28560
aacagttaac tgctgaagat cgtaaccatt gtatgaaact gtctaaaaaa atccatagag   28620
aaaaaactat acacccaaca gtaaatctca atggtagtgc atgttttttg caatctcctt   28680
ctgacgctat ttttgtcgc catctgtcat tgcaatacgc ccttgattca ttgagaaatg   28740
gaaaaggcaa agtcaacctg attaaacatt actcctccgt tgaatccata cagcagcata   28800
```

```
tcccCttagt ccgggatgcg gagttcagag cattacttcg ccatcctcct gcagggagtc    28860
gcgttatcgc gagtaaggat tttggcttcg ctttagatat tttcttttgt cgaatgatgg    28920
caaacaatgt cagtcatatg tccgcgattt tatatataga caatcatact ttgtcagtaa    28980
ggctacgaat aaagcagtca gtgtatggac aattaaatta tgttgtgtct gtttacgacc    29040
cgaacgatac caacgttgcc gtcagaggca cccacaggac agcacggcgc tttctctcgc    29100
ttgataagtt catcagttca gctcccgatg ctcagacctg ggctgatagg tatgttcgca    29160
actgtgcaat tgctattctt cctctattac ctgagggagt tccagttgct attttagcgg    29220
gtatcacgac acgaatgcca tttgcccta tacatccatc ggcaatgttg ttaataatgg    29280
ccacaggcca gactcaatag cttattacac tattcaaaca gttgcccata ctccctgaaa    29340
aagaaatcat tgaaataata actgcgcaga atagcgttgg tacacctgct ttatttctgg    29400
ctatgatgaa cggacaaact gacaacgtaa aaatatttat gcaagaaatc cagtcactgg    29460
tatacaatca tatcattcat gaagataatc tggttaaatt actgcaaact aaaagtgcta    29520
acgaaacacc tggactctat atctccatgt tgtatggatt cgatgaaata atcgatatct    29580
ttctgaatgc attaaccact ccaatagcac aagaactttt aaacaaaaaa atggtgatgg    29640
atattttagc catgaaaaca cgtgatgtg aaccaggggtt atttgctgca atggaaaata    29700
atcacccttt gtgtgtcaca cggttcctct ctaaagttta tgggatcgcc gttaaatata    29760
aactcagcaa aatcaacatc atggacttat taaaggcgc gacagcacat ggaacccctg    29820
ctttatacat cgccatgagc aagggtaata agacgtcgt gttatcttat atatcaacac    29880
tgagtacttt tgcaaaaaaa tattcttttta gtcaacgtca attattcaca ctgttggccg    29940
ctaaaaatca tgaaaacatg tcagctgttc atatagccat tcatcataat cattataaaa    30000
ctgtagaaac atattatgct gctattaatg caatcagcca aagcctgagt tttagtgctg    30060
atgaactaaa aacgtatta taaccagcta tttatgatat ttgtatatcg atacataatt    30120 ttatttttt cataaaacgc agaaacagtg atcaggtgta caacgccacc cgacggctgt    30180
aataacaaaa aatcccttga tgcctgtccc ttttgttaca ctccgttatc acgcacaaga    30240
gatatgcagg acactggtat gccgactaaa cgctttgata aaaaacactg gaagatggtg    30300
gtggtgctac tggcaatctg tggcgctatg ttgttgctac gttgggcagc aatgatttgg    30360
ggctgagcag tgacaaacga agacagccag accgcataac acggtccggc agataattt    30420 acatgctgta gcccagcgat aaggttgtcc gacgatcggt atgttccggt gcagactctg    30480
gaggttcaga gttccatgtg acgttgtaag ccactttcag tccaaaatgt tcattaatag    30540
caacatttaa tgcgctttcg gagttcagcg ttgtgtcttc cgcgccaaag acggaaacac    30600
cctgcgtaaa tttagcgttg tcagtcaact gccatgcata agcaccggag gcatagccca    30660
gcggctgagt ttcactggca ttgtcggtat atttgtcgta acgcacacct ggaccgaatt    30720
caaagcggaa actgtgtacc gggccattca aaaactgacg accataaccc gcggtcaaca    30780
catcgcgctc tcgatagccg ttataacggt ctgtcagcca gcttgcctga ccaaataaat    30840
agtcataatc agttaaatta aaacggctac gcccgcccgc cgcatatttt tctgaagaac    30900
gctcatcatt agaagaagta ttactggcgt tcccccacag cgaccaggca gtggtttgtc    30960
cataccaggt catggtggtg tcagccgtaa gtgaggagct tttcgtattg cctgattgtg    31020
caagatatcc tgcgttcaga ttaccttcga aaggttttt agcgctggca ggatcgtcca    31080
tgacagtaaa aacggaatca tcggcagctg cattcagtga cgcaaacatg ccccccgcca    31140
acataacgat ggcaggaact gtcttcaaaa gcttcatta tcaagagtcc gtacaacaaa    31200
```

```
aaaagagacc atcgcggtcc cggaaacttt cttaaggatc aaagattagc gtccctggaa   31260
aggtaacgaa ttataaaaag gcgcgaataa cttagcaatg tattcttatt tcatttttg    31320 aataagcatg tggcgaaaac agatttttat ttatatatat ttatctgcaa aattttaaat   31380
aaagctctaa taaatcatat tgttaatttc ttcactttcg gctgattcgg tgccagactg   31440
aaatcagcct ataggaggaa atgatggtac gtatctatac gttgacactt gcgccctctc   31500
tcgatagcgc aacaattacc ccgcaaattt atcccgaagg aaaactgcgc tgtaccgcac   31560
cggtgttcga acccgggggc ggcggcatca acgtcgcccg cgccattgcc catcttggag   31620
gcagtgccac agcgatcttc ccggcgggtg gcgcgaccgg cgaacacctg gtttctctgt   31680
tggcggatga aaatgtcccc gtcgctactg tagaagccaa agactggacc cggcagaatt   31740
tacacgtaca tgtggaagca agcggtgagc agtatcgttt tgttatgcca ggcgcggcat   31800
taaatgaaga tgagtttcgc cagcttgaag agcaagttct ggaaattgaa tccggggcca   31860
tcctggtcat aagcggaagc ctgccgccag gtgtgaagct ggaaaaatta acccaactga   31920
tttccgctgc gcaaaaccaa gggatccgct gcatcatcga cagttctggc gaagcgttaa   31980
gtgcagcact ggcgattggt aacatcgagt tggttaagcc taaccaaaaa gaactcagtg   32040
cgctggtgaa tcgcgaactc acccagccag acgatgtccg caaagccgcg caggaaatcg   32100
ttaatagcgg caaggccaaa cggggttgtcg tttcccttgg tccacaagga gcgctgggtg   32160
ttgatagtga aaactgcatt caggtggtgc caccaccggt gaaaagccag agtaccgttg   32220
gcgctggtga cagcatggtc ggcgcgatga cactgaaact ggcagaaaat gcctctcttg   32280
aagagatggt ccgttttggc gtagctgcgg ggagtgcagc cacactcaat cagggaacac   32340
gtctgtgctc ccatgacgat acgcaaaaaa tttacgctta cctttcccgc taacaaaaac   32400
attcccccag cattggggga atcaccacca acctgtcggc aacgcgtttc tccgactatg   32460
ctcaaaagtc atgtgataac aaaggggtga actatggcca gtggcgatct tgtccgttat   32520
gtcataaccg tcatgttgca tgaggataca ttgactgaaa ttaacgagtt gaataattac   32580
ctgactcgcg acggtttttt tgctcaccat gacggatgat gagggaaata tccatgagct   32640
ggggactaac acttttggac ttatcagtac ccaaagtgaa gaagaaatta gagaactggt   32700
ttcggggctt acccaaagtg caaccggcaa agatcctgaa atcaccatca cgacctggga   32760
ggaatggaat agcaacagaa aataaatggt ttttgggcaa taatcagtct gtggtgtgcg   32820
ttagctcgtg tttttacacc gcattcttgc gctaacctta tgatctggca gacaacatgg   32880
gagagacatc atgtggcagg caatccgtcg tcttttgagc gagcagttag gtgaaggcga   32940
aatcgaactg cgtaatgaac tgcctggcgg agaagtccat gccgcatggc atttgcgcta   33000
tgcaggacat gactttttcg tcaaatgtga tgaaagggaa ctgcttcccg gttttaccgc   33060
cgaagccgac caactggagt tactgtcgcg tagtaaaacc gtcaccgtgc ctaaggtttg   33120
ggcagtaggc gctgaccgtg actacagttt tctggtgatg gattatctcc cacctcgtcc   33180
gctggatgcg catagcgcat ttattcttgg tcagcaaatt gcgcgtttac atcaatggag   33240
tgaccaacca caatttggcc tcgattttga taactcgctc tccacaactc cacagcccaa   33300
cacctggcaa cgtcgctggt caacgttttt tgctgaacaa cggattggct ggcagttgga   33360
actggcagca gagaaaggga tcgctttcgg caatatcgac gccatcgtcg agcatattca   33420
gcagcgtctg gcctcgcatc aaccgcagcc ttctctgttg cacggcgatt tatggtccgg   33480
caactgtgcg ctgggtccgg atggcccgta cattttcgac cctgcctgct actggggtga   33540
```

```
ccgagagtgc gacctggcga tgttaccgct gcatactgaa cagccgccac aaatctatga   33600
cggctatcag tcagtatccc cgctacctgc cgatttcctt gaacgtcaac cggtttacca   33660
actctacacg ctgttaaatc gtgcaagatt atttggcggt cagcatttgg ttattgctca   33720
gcagtcattg gatagattat tagcagcatg atatgggttg aggataatgg ccgctccgtg   33780
cggccttttg attaaataaa cccaagcaga gaaaagaaca cataacctgc agcaatacaa   33840
ataaccggca ggatatatag tgagaaaaac tgcaggaaaa tagtatggtg cggaacaaca   33900
atacgggact caatttgttc acgcgttagc ccctcttccc ctttggcttt ttccagaatg   33960
agttgatctt caacaccttc ccgcaagaag cgcgcctggc gactcatccg ggcaccggaa   34020
tcctgcaacg ccagtccgac aaaaatcagg atgaaaatca cccagaacat aacgttcacg   34080
ccaccattaa aattaggggt cggggagtta taccagaaca gattcaaaaa aggcgtattc   34140
gcctgcatca tatcgatcat gacatgagta aagtcgagca tgaccgcatt aatgccttcc   34200
tggttttcct gccgggtatt cataaatttc agcaaagaaa tcaatgtaga gatcaatgca   34260
ggtataaaaa tcacccaacc caaaatcctt ttcaaaacag caatgcgtcc agcttgttga   34320
tacgtcatga gttctccttg attaagacgc gtcgtttcac ttagtttacc tgtagatatc   34380
tgttttcgcc cattctttaa aggcgatatg ataggcgctt aatcataagc acggcttaat   34440
accttacaca taatgctcta aaggagaggt tgtaatgtca accccgcgtc agattcttgc   34500
tgcaattttt gatatggatg gattacttat cgactcagaa cctttatggg atcgagccga   34560
actggatgtg atggcaagcc tgggggtgga tatctcccgt cgtaacgagc tgccggacac   34620
cttaggttta cgcatcgata tggtggtcga tctttggtac gcccggcaac cgtggaatgg   34680
gccaagccgt caggaagtag tagaacgggt tattgcccgt gccatttcac tggttgaaga   34740
gacacgtcca ttattaccag gcgtgcgcga agccgttgcg ttatgcaaag aacaaggttt   34800
attggtggga ctggcctccg cgtcaccact acatatgctg gaaaaagtgt tgaccatgtt   34860
tgacttacgc gacagtttcg atgccctcgc ctcggctgaa aaactgcctt acagcaagcc   34920
gcatccgcaa gtatatctcg actgcgcagc aaaactgggc gttgacccac tgacctgcgt   34980
agcactggaa gattcagtaa atggcatgat cgcctctaaa gcagcccgca tgcgttccat   35040
cgtcgttcct gcgccagaag cgcaaaatga tccacgtttt gtattagcaa acgtcaaact   35100
ctcatcgctg acagaactca ccgcaaaaga ccttctcggt taatggccag gggcagtgat   35160
ctcgctgccc ctggttcttt atctgaattt gcattcaact gacggattaa tcgtcaattt   35220
aagagaaaga gttacaccgt caccacttcc gtgcactgta taaaaatcct atactgtacg   35280
tatcgacagt ttagtgagtt ttatcatgac ggcggaaggt caccttctct tttctattgc   35340
ttgtgcggta tttgccaaaa atgccgagct gacgccgtg ctggcacagg gtgactggtg   35400
gcatattgtc ccttccgcaa tcctgacgtg tttgttaccg gacatcgatc acccaaagtc   35460
gtttcttggg cagcgattaa agtggatatc aaaaccgatc gcccgcgctt ttgggcatcg   35520
tggttttacc cacagtctgc tggcggtatt tgcgctgctg gcaacctttt accttaaggt   35580
tcctgaaagc tggttcattc cggctgatgc gctacaagga atggtgctgg gttatttaag   35640
ccacatactt gccgatatgc tgacacccgc cggtgttccc ctgctctggc catgtcgctg   35700
gcgtttccgc ttgcctatcc tggttcccca aaagggcaac caactggaac gttttatctg   35760
catggcatta tttgtctggt cggtatggat gccccattca ttacccgaaa acagcgcggt   35820
tcgttggtca tcgcaaatga tcaataccct tgcagatccag tttcatcggc ttattaagca   35880
tcaggttgaa tactaaaaag gcaaaaatca ccttttctgga ataagcaatt ccatttgaat   35940
```

```
ataagagcca gctcacagtt ctgttaatct tgcgccaaca ctatgactgc tacgcagtga    36000
tagaaataat aagatcagga gaacggggat gaactttcca ttaattgcga acatcgtggt    36060
gttcgttgta ctgctgtttg cgctggctca gacccgccac aaacagtgga gtctggcgaa    36120
aaaagtgctg gtgggtctgg tgatgggtgt ggttttttgc cttgccctgc ataccattta    36180
tggttctgac agccaggtac ttaaagattc tgtacagtgg tttaacatcg ttggtaacgg    36240
ctatgttcaa ctgctgcaaa tgatcgttat gccgttagtc ttcgcctcta ttctgagcgc    36300
ggttgcccgt ctgcataacg catctcagtt aggcaaaatc agttttctga ccatcggtac    36360
gcttttgttt accacactga ttgcggcgct ggtcggtgtg ctggtcacca acctgtttgg    36420
tttgacggct gaaggtctgg ttcagggtgg tgcagaaact gcacgtctga acgccatcga    36480
aagtaactat gttggtaaag tctctgacct gagcgttccg cagctggtct tgtcctttat    36540
cccgaaaaac ccgtttgccg atcttaccgg agccaatccg acgtcaatta tcagcgtggt    36600 aattttttgcc acattcctcg gcgtagctgc attgaaactg ctgaaggatg atgcgccgaa    36660
aggtgaacgc gtcttagccg ctatcgatac cctacaaagc tgggtgatga aactggttcg    36720
ccttgtcatg cagttgaccc cttacggcgt tctggctcta atgaccaaag tggttgcagg    36780
ttctaacttg caagacatca tcaaactggg aagtttcgtt gtcgcgtcct acctcggtct    36840
gctgattatg tttgcagtgc atggcattct gctgggcatt aatggcgtga gtccgctgaa    36900
gtacttccgt aaggtatggc ctgtgctgac gtttgccttt accagccgtt ccagtgctgc    36960
gtctatccca ctgaatgtgg aagcacaaac gcgtcgtctg ggcgttcctg aatccatcgc    37020
cagtttcgcc gcctctttcg gtgcaaccat tggtcagaac ggctgcgccg gtttgtatcc    37080
ggcaatgctg gcggtgatgg ttgcgcctac ggttggcatt aacccgctgg acccgatgtg    37140
gattgcgacg ctggtcggta ttgttaccgt tagttccgca ggcgttgccg gtgtcggtgg    37200
tggtgcaact ttcgccgcac tgattgtgct gcctgcgatg ggcctgccag taaccctggt    37260
ggcgctgtta atctccgttg aaccgcttat cgacatgggc cgtacggcgc taaacgttag    37320
tggctcgatg acagctggca cgctgaccag ccagtggctg aagcaaaccg ataaagccat    37380
tctggatagc gaagacgacg ccgaactggc acaccgttaa ttcttatgct ggcaacggtc    37440
cgttttgtat aggggccgtt gctttacttt ttaaatgttc catcgcggcg atgcatactg    37500
actcatattt aaacagatcg tcagcgaaaa aaatgtccaa cttatcaata cattcctggc    37560
tcaatgaatg tgcctgtagt gagaagctta aaacctcata cccgagacgt tttctaagga    37620
aggtgcgaac aagttcctga tatgagatca tcatattcat ccggagcgca tcccagaggg    37680
acatcatgag ccatcaactc accttcgccg atagtgaatt cagcactaag cgccgtcaga    37740
cccgaaaaga gattttcctc tcccgcatgg agcagattct gc                        37782
```

<210> SEQ ID NO 2
<211> LENGTH: 31258
<212> TYPE: DNA
<213> ORGANISM: Escherichia coli
<220> FEATURE:
<221> NAME/KEY: misc_feature
<223> OTHER INFORMATION: n is a, t, g, or c
<220> FEATURE:
<221> NAME/KEY: misc_feature
<222> LOCATION: (5930)..(8928)
<223> OTHER INFORMATION: n is a, c, g, or t
<220> FEATURE:
<221> NAME/KEY: misc_feature
<222> LOCATION: (13314)..(16140)
<223> OTHER INFORMATION: n is a, c, g, or t
<220> FEATURE:
<221> NAME/KEY: misc_feature
<222> LOCATION: (20898)..(22025)
<223> OTHER INFORMATION: n is a, c, g, or t

<400> SEQUENCE: 2

| | | | | | |
|---|---|---|---|---|---|
| catggctgtc | tggtctatca | gcgcctgcgc | ggtgtcgggc | accgccgcat | ccagcggcgt | 60 |
| gatcttcaag | cccgactcgg | tgatgatggc | atccggcagg | tcgttggctg | ccgccatgcg | 120 |
| gttgacggtg | gcaagttgtg | cttccagcag | cgtcagccgc | tcatgcagat | attgttcgca | 180 |
| gtcggtggcc | acggccagcg | gcaattcgct | ggactgcttg | aggctggtga | acttctcggg | 240 |
| cggtaccagg | tagtcctcga | agtccttgaa | ctggcgtgaa | ccctgcaccc | agatgtcgcc | 300 |
| cgagcgcagg | gagttcttca | actcggacag | cgcgcacagt | tcgtagtagc | gccggtcgat | 360 |
| gccggcgtcg | gtcatcacca | gtttctgcca | gcgcggcttg | atgaagccgg | tcggtgcatc | 420 |
| ggctggcagc | ttgcgggcgt | tgtcggtgtt | catgccgcgc | agcacctcaa | tggcatcaag | 480 |
| cacgttttg | gcggcgggcg | cggcccgcag | cttgagcacg | gcaaggaatt | ccggtgcata | 540 |
| gcggcgcagg | gtggcgtagc | tctcgccgat | gcgatgcagg | aaatcgaagt | catcgggttg | 600 |
| cgcgagcttc | tgcgcctcgg | tgacgctctc | ggcaaaggaa | tcccaggaca | tgacggcctc | 660 |
| gatggcggca | aacgcatcgc | ggcctgattg | cttggcgtcg | atcagcgcct | gaccgatgcg | 720 |
| cccgtacaga | cgtaccttgg | cgttgatggc | cttgcctgac | gctgaaact | gctgctgatg | 780 |
| cttattcttg | gcagcgttaa | acagcttacc | caggatgcgg | tcgtgcaggt | cgatgatttc | 840 |
| gtcggtgacg | gtgccatgc | cctcggtggc | cagcgccacg | agagtggcgt | agcgccgttg | 900 |
| cggctcgaat | ttggccaggt | cggcgggtgt | catctggccg | ccctcgcggg | caatcttgag | 960 |
| caggcggttc | tggtgaacca | gccgctcgat | gccggtaggc | agatcgagtg | cctgccatgc | 1020 |
| cttgaggcgt | tcgatgtgtt | ccagcatatg | ccgcgaattt | ggcttggccg | gagactggcg | 1080 |
| caaccaagcc | aaccaggtcg | tcttgccgtt | gtcccggcgc | ttgagcagat | cgtcgaggcg | 1140 |
| gcggcgatgc | gcgtccgcca | gtggttcggc | caaggcgtcg | tagatgcgcc | ggttagcacg | 1200 |
| ggtgatcgcc | tcggcactcg | cccgctcgac | ggcgttgagg | gcgggcagaa | tgaccgactg | 1260 |
| ccgccgcagg | tgcccgatca | aggcgctggc | cagcacgatg | cctttgtcgg | tttgcatcgc | 1320 |
| cagctcggtc | agcatctgga | cggcctgccg | gtaatggctc | atggtgaagg | gccggaaacc | 1380 |
| gaacacggtt | tgcagctcgc | tcaggtgctc | gcgccggtc | tgctcccgct | ggccgtactc | 1440 |
| gttccagctt | tcgacgccga | ccttgagctg | gtcggcgacc | agcttcaaca | agggcgggaa | 1500 |
| cggtagttca | tcgacgccca | ggatgacgcc | gggaaagcgc | aggtaacaga | gctgcaccgc | 1560 |
| gaagcccagc | cgattggctg | gcccgcgccg | ctgtcggatg | atcgagaggt | cggtatcgtt | 1620 |
| gaatgtgtaa | tgtcggatca | ggtcgtcctt | ggagtccggc | aacgccagca | ggcttttccccg | 1680 |
| ctcggcggcg | gacaggatgg | aacgacgtgg | catatttact | gatccgttct | caagtattga | 1740 |
| tacagggttt | cgcgactgat | tccgaattca | cgagcaagct | tggtcttttg | ctcgccagcc | 1800 |
| tcgacacgtt | ggcgcagttc | ggcaatacgc | tcagacgaca | gggatttctt | cctgccacgg | 1860 |
| taagccccgc | gttgcttggc | gagcgcaata | ccctcgcgct | gacgctcgcg | gatcagggcg | 1920 |
| cgctcgaact | cggcgaacgc | gcccatcacc | gagagcatca | ggttcgccat | cggagagtct | 1980 |
| tcgccagtaa | aactgaggtg | ttccttgacg | aattcgatat | gcacgccgcg | ttgtgtcagc | 2040 |
| gtttgcacga | tccggcgcaa | atcatcgaga | ttgcgcgcca | ggcgatccat | gctatgcacc | 2100 |
| accacggtgt | cgccggtgcg | ggcgaagctt | atcagcgctt | ccagttgcgg | acgcttgaca | 2160 |

```
tccttgccgg atgccttgtc gctaaaagcg cgatcaacct tgacgccttc cagttgccgt    2220
tccgggttct ggtcgaaggt gctgaccctg atatacccaa tgcgctgtcc agtcatggaa    2280
ttccctgcaa aatgtcaggg aagactctat gaccttcaac gagatatgtc aataaattca    2340
aaattcaatc ctatcctgac gcaatttaca catggcatct gacatcaggt tagggtatgc    2400
ctcaacctga cggcggcgaa tcacaagcgt ccggtttgac gctggtttcg gtcgcagtgc    2460
tggcccgcgc ctggaagcgc tgatagcact ccagcccgca gaaatgctcc acgtactcgg    2520 cccccttccgg cgtgaaggcg gcatcgagcg ggatttcctt gcagcacacg cagcaactgg    2580
tgctcggttc attggcgttc atggtggtgt tcctccattg gttgacgaag ccgacgaagg    2640
ccgccgccgg catcggcctg gcgaacagga aaccctgcac cgtgtcgcaa cccgcctgcc    2700
gcaaccacgc aaggcagtcg ggtgtttcca caccctcggc taccacctcc attgtcgttt    2760
tcagaagacg gctgcactga acgtcagaag ccgactgcac tatagcagcg gaggggttgg    2820
atccatcagg caacgacggg ctgctgccgg ccatcagcgg acgcagggag gactttccgc    2880
aaccggccgt tcgatgcggc accgatggcc ttcgcgcagg ggtagtgaat ccgccaggat    2940
tgacttgcgc tgccctacct ctcactagtg aggggcggca gcgcatcaag cggtgagcgc    3000
actccggcac cgccaacttt cagcacatgc gtgtaaatca tcgtcgtaga gacgtcggaa    3060
tggccgagca gatcctgcac ggttcgaatg tcgtaaccgc tgcggagcaa ggccgtcgcg    3120
aacgagtggc ggagggtgtg cggtgtggcg ggcttcgtga tgcctgcttg ttctacggca    3180
cgtttgaagg cgcgctgaaa ggtctggtca tacatgtgat ggcgacgcac gacaccgctc    3240
cgtggatcgg tcgaatgcgt gtgctgcgca aaaacccaga accacggcca ggaatgcccg    3300
gcgcgcggat acttccgctc aagggcgtcg ggaagcgcaa cgccgctgcg gccctcggcc    3360
tggtccttca gccaccatgc ccgtgcacgc gacagctgct cgcgcaggct gggtgccaag    3420
ctctcgggta acatcaaggc ccgatccttg gagcccttgc cctcccgcac gatgatcgtg    3480
ccgtgatcga aatccagatc cttgacccgc agttgcaaac cctcactgat ccgcatgccc    3540
gttccataca gaagctgggc gaacaaacga tgctcgcctt ccagaaaacc gaggatgcga    3600
accacttcat ccggggtcag caccaccggc aagcgccgcg acggccgagg tcttccgatc    3660
tcctgaagcc agggcagatc cgtgcacagc accttgccgt agaagaacag caaggccgcc    3720
aatgcctgac gatgcgtgga gaccgaaacc ttgcgctcgt tcgccagcca ggacagaaat    3780
gcctcgactt cgctgctgcc caaggttgcc gggtgacgca caccgtggaa acggatgaag    3840
gcacgaaccc agtggacata agcctgttcg gttcgtaagc tgtaatgcaa gtagcgtatg    3900
cgctcacgca actggtccag aaccttgacc gaacgcagcg gtggtaacgg cgcagtggcg    3960
gttttcatgg cttgttatga ctgttttttt gtacagtcta tgcctcgggc atccaagcag    4020
caagcgcgtt acgccgtggg tcgatgtttg atgttatgga gcagcaacga tgttacgcag    4080
cagggcagtc gccctaaaac aaagttagcc attacggggg ttgaattgaa aatttcattg    4140
atttctgcaa cgtcagaaaa tggcgtaatc ggtaatggcc ctgatatccc atggtcagca    4200
aaaggtgagc agttactctt taaagcgctc acatataatc agtggctcct tgttggaagg    4260
aaaacatttg actctatggg tgttcttcca aatcgaaaat atgcagtagt gtcgaggaaa    4320
ggaatttcaa gctcaaatga aaatgtatta gtctttcctt caatagaaat cgctttgcaa    4380
gaactatcga aaattacaga tcatttatat gtctctggtg gcggtcaaat ctacaatagt    4440
cttattgaaa aagcagatat aattcatttg tctactgttc acgttgaggt tgaaggtgat    4500
atcaattttc ctaaaattcc agagaatttc aatttggttt ttgagcagtt ttttttgtct    4560
```

```
aatataaatt acacatatca gatttggaaa aaaggctaac aagtcgttcc agcaccagtc   4620
gctgcgctcc ttggacagtt tttaagtcgc ggttttatgg ttttgctgcg caaaagtatt   4680
ccataaaacc acaacttaaa aactgccgct gaactcggcg ttagatgcac taagcacata   4740
attgctcaca gccaaactat caggtcaagt ctgcttttat tattttttaag cgtgcataat   4800 aagccctaca caaattggga gatatatcat gaaaggctgg cttttcttg ttatcgcaat   4860 agttggcgaa gtaatcgcaa catccgcatt aaaatctagc gagggcttta ctaagcttgc   4920
cccttccgcc gttgtcataa tcggttatgg catcgcattt tattttcttt ctctggttct   4980
gaaatccatc cctgtcggtg ttgcttatgc agtctggtcg ggactcggcg tcgtcataat   5040
tacagccatt gcctggttgc ttcatgggca aaagcttgat gcgtggggct ttgtaggtat   5100
ggggctcata attgctgcct ttttgctcgc ccgatcccca tcgtggaagt cgctgcggag   5160
gccgacgcca tggtgacggt gttcggcatt ctgaatctca ccgaggactc cttcttcgat   5220
gagagccggc ggctagaccc cgccggcgct gtcaccgcgg cgatcgaaat gctgcgagtc   5280
ggatcagacg tcgtggatgt cggaccggcc gccagccatc cggacgcgag gcctgtatcg   5340
ccggccgatg agatcagacg tattgcgccg ctcttagacg ccctgtccga tcagatgcac   5400
cgtgtttcaa tcgacagctt ccaaccggaa acccagcgct atgcgctcaa gcgcggcgtg   5460
ggctacctga acgatatcca aggatttcct gaccctgcgc tctatcccga tattgctgag   5520
gcggactgca ggctggtggt tatgcactca gcgcagcggg atggcatcgc cacccgcacc   5580
ggtcaccttc gacccgaaga cgcgctcgac gagattgtgc ggttcttcga ggcgcgggtt   5640
tccgccttgc gacggagcgg ggtcgctgcc gaccggctca tcctcgatcc ggggatggga   5700 ttttcttga gccccgcacc ggaaacatcg ctgcacgtgc tgtcgaacct tcaaaagctg   5760
aagtcggcgt tggggcttcc gctattggtc tcggtgtcgc ggaaatcctt cttgggcgcc   5820
accgttggcc ttcctgtaaa ggatctgggt ccagcgagcc ttgcggcgga acttcacgcg   5880
atcggcaatg cgctgactca cgtccgcacc cacgcgcctg gagatctgcn nnnnnnnnn   5940 nnnnnnnnnn nnnnnnnnnn nnnnnnnnnn nnnnnnnnnn nnnnnnnnnn nnnnnnnnnn   6000
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnnnnnnnnn   6660
nnnnnnnnnn nnnnnnnnnn nnnnnnnnnn nnnnnnnnnn nnnnnnnnnn nnnnnnnnnn   6720
nnnnnnnnnn nnnnnnnnnn nnnnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnnnnnnnnn nnnnnnnnnn nnnnnnnnnn nnnnnnnnnn nnnnnnnnnn nnnnnnnnnn   6900
```

```
nnnnnnnnnn nnnnnnnnnn nnnnnnnnnn nnnnnnnnnn nnnnnnnnnn nnnnnnnnnn   6960
nnnnnnnnnn nnnnnnnnnn nnnnnnnnnn nnnnnnnnnn nnnnnnnnnn nnnnnnnnnn   7020
nnnnnnnnnn nnnnnnnnnn nnnnnnnnnn nnnnnnnnnn nnnnnnnnnn nnnnnnnnnn   7080
nnnnnnnnnn nnnnnnnnnn nnnnnnnnnn nnnnnnnnnn nnnnnnnnnn nnnnnnnnnn   7140
nnnnnnnnnn nnnnnnnnnn nnnnnnnnnn nnnnnnnnnn nnnnnnnnnn nnnnnnnnnn   7200
nnnnnnnnnn nnnnnnnnnn nnnnnnnnnn nnnnnnnnnn nnnnnnnnnn nnnnnnnnnn   7260
nnnnnnnnnn nnnnnnnnnn nnnnnnnnnn nnnnnnnnnn nnnnnnnnnn nnnnnnnnnn   7320
nnnnnnnnnn nnnnnnnnnn nnnnnnnnnn nnnnnnnnnn nnnnnnnnnn nnnnnnnnnn   7380
nnnnnnnnnn nnnnnnnnnn nnnnnnnnnn nnnnnnnnnn nnnnnnnnnn nnnnnnnnnn   7440
nnnnnnnnnn nnnnnnnnnn nnnnnnnnnn nnnnnnnnnn nnnnnnnnnn nnnnnnnnnn   7500
nnnnnnnnnn nnnnnnnnnn nnnnnnnnnn nnnnnnnnnn nnnnnnnnnn nnnnnnnnnn   7560
nnnnnnnnnn nnnnnnnnnn nnnnnnnnnn nnnnnnnnnn nnnnnnnnnn nnnnnnnnnn   7620
nnnnnnnnnn nnnnnnnnnn nnnnnnnnnn nnnnnnnnnn nnnnnnnnnn nnnnnnnnnn   7680
nnnnnnnnnn nnnnnnnnnn nnnnnnnnnn nnnnnnnnnn nnnnnnnnnn nnnnnnnnnn   7740
nnnnnnnnnn nnnnnnnnnn nnnnnnnnnn nnnnnnnnnn nnnnnnnnnn nnnnnnnnnn   7800
nnnnnnnnnn nnnnnnnnnn nnnnnnnnnn nnnnnnnnnn nnnnnnnnnn nnnnnnnnnn   7860
nnnnnnnnnn nnnnnnnnnn nnnnnnnnnn nnnnnnnnnn nnnnnnnnnn nnnnnnnnnn   7920
nnnnnnnnnn nnnnnnnnnn nnnnnnnnnn nnnnnnnnnn nnnnnnnnnn nnnnnnnnnn   7980
nnnnnnnnnn nnnnnnnnnn nnnnnnnnnn nnnnnnnnnn nnnnnnnnnn nnnnnnnnnn   8040
nnnnnnnnnn nnnnnnnnnn nnnnnnnnnn nnnnnnnnnn nnnnnnnnnn nnnnnnnnnn   8100
nnnnnnnnnn nnnnnnnnnn nnnnnnnnnn nnnnnnnnnn nnnnnnnnnn nnnnnnnnnn   8160
nnnnnnnnnn nnnnnnnnnn nnnnnnnnnn nnnnnnnnnn nnnnnnnnnn nnnnnnnnnn   8220
nnnnnnnnnn nnnnnnnnnn nnnnnnnnnn nnnnnnnnnn nnnnnnnnnn nnnnnnnnnn   8280
nnnnnnnnnn nnnnnnnnnn nnnnnnnnnn nnnnnnnnnn nnnnnnnnnn nnnnnnnnnn   8340
nnnnnnnnnn nnnnnnnnnn nnnnnnnnnn nnnnnnnnnn nnnnnnnnnn nnnnnnnnnn   8400
nnnnnnnnnn nnnnnnnnnn nnnnnnnnnn nnnnnnnnnn nnnnnnnnnn nnnnnnnnnn   8460
nnnnnnnnnn nnnnnnnnnn nnnnnnnnnn nnnnnnnnnn nnnnnnnnnn nnnnnnnnnn   8520
nnnnnnnnnn nnnnnnnnnn nnnnnnnnnn nnnnnnnnnn nnnnnnnnnn nnnnnnnnnn   8580
nnnnnnnnnn nnnnnnnnnn nnnnnnnnnn nnnnnnnnnn nnnnnnnnnn nnnnnnnnnn   8640
nnnnnnnnnn nnnnnnnnnn nnnnnnnnnn nnnnnnnnnn nnnnnnnnnn nnnnnnnnnn   8700
nnnnnnnnnn nnnnnnnnnn nnnnnnnnnn nnnnnnnnnn nnnnnnnnnn nnnnnnnnnn   8760
nnnnnnnnnn nnnnnnnnnn nnnnnnnnnn nnnnnnnnnn nnnnnnnnnn nnnnnnnnnn   8820
nnnnnnnnnn nnnnnnnnnn nnnnnnnnnn nnnnnnnnnn nnnnnnnnnn nnnnnnnnnn   8880
nnnnnnnnnn nnnnnnnnnn nnnnnnnnnn nnnnnnnnnn nnnnnnnngg taaatccatg   8940
ctggccctgc aactggccgc acagattgca ggcgggccgg atctgctgga ggtgggcgaa   9000
ctgcccaccg gcccggtgat ctacctgccc gccgaagacc cgcccaccgc cattcatcac   9060
cgcctgcacg cccttggggc gcacctcagc gccgaggaac ggcaagccgt ggctgacggc   9120
ctgctgatcc agccgctgat cggcagcctg cccaacatca tggccccgga gtggttcgac   9180
ggcctcaagc gcgccgccga gggccgccgc ctgatggtgc tggacacgct gcgccggttc   9240
cacatcgagg aagaaaacgc cagcggcccc atggcccagg tcatcggtcg catggaggcc   9300
```

```
atcgccgccg ataccgggtg ctctatcgtg ttcctgcacc atgccagcaa gggcgcggcc    9360
atgatgggcg caggcgacca gcagcaggcc agccggggca gctcggtact ggtcgataac    9420
atccgctggc agtcctacct gtcgagcatg accagcgccg aggccgagga atggggtgtg    9480
gacgacgacc agcgccggtt cttcgtccgc ttcggtgtga gcaaggccaa ctatggcgca    9540
ccgttcgctg atcggtggtt caggcggcat gacggcgggg tgctcaagcc cgccgtgctg    9600
gagaggcagc gcaagagcaa gggggtgccc cgtggtgaag cctaagaaca agcacagcct    9660
cagccacgtc cggcacgacc cggcgcactg tctggccccc ggcctgttcc gtgccctcaa    9720
gcggggcgag cgcaagcgca gcaagctgga cgtgacgtat gactacggcg acggcaagcg    9780
gatcgagttc agcggcccgg agccgctggg cgctgatgat ctgcgcatcc tgcaagggct    9840
ggtggccatg gctgggccta atggcctagt gcttggcccg gaacccaaga ccgaaggcg    9900 acggcagctc cggctgttcc tggaacccaa gtgggaggcc gtcaccgctg atgccatggt    9960
ggtcaaaggt agctatcggg cgctggcaaa ggaaatcggg gcagaggtcg atagtggtgg   10020
ggcgctcaag cacatacagg actgcatcga gcgccttttgg aaggtatcca tcatcgccca   10080
gaatggccgc aagcggcagg ggtttcggct gctgtcggag tacgccagcg acgaggcgga   10140
cgggcgcctg tacgtggccc tgaaccccctt gatcgcgcag gccgtcatgg gtggcggcca   10200
gcatgtgcgc atcagcatgg acgaggtgcg ggcgctggac agcgaaaccg cccgcctgct   10260
gcaccagcgg ctgtgtggct ggatcgaccc cggcaaaacc ggcaaggctt ccatagatac   10320
cttgtgcggc tatgtctggc cgtcagaggc cagtggttcg accatgcgca agcgccgcca   10380
gcgggtgcgc gaggcgttgc cggagctggt cgcgctgggc tggacggtaa ccgagttcgc   10440
ggcgggcaag tacgcatca cccggcccaa ggcggcaggc tgacccccccc cactctattg   10500 taaacaagac atttttatct tttatattca atggcttatt ttcctgctaa ttggtaatac   10560
catgaaaaat accatgctca gaaaaggctt aacaatattt tgaaaaattg cctactgagc   10620
gctgccgcac agctccatag gccgctttcc tggctttgct tccagatgta tgctattctg   10680
ctcctgcagc taatgatca ccgcaaacag gttactcgcc tggggattcc ctttcgaccc   10740
gagcatccgt atgagactca tgctcgatta ttattattat agaagccccc atgaataaat   10800
cgctcatcat tttcggcatc gtcaacataa cctcggacag tttctccgat ggaggccggt   10860
atctggcgcc agacgcagcc attgcgcagg gcgtaagct gatggccgag ggggcagatg   10920
tgatcgacct cggtccggca tccagcaacc ccgacgccgc gcctgtttcg tccgacacag   10980
aaatcgagcg tatcgcgccg gtgctggacg cgctcaaggc agatggcatt cccgtctcgc   11040
tcgacagtta tcaacccgcg acgcaagcct atgccttgtc gcgtggtgtg gcctatctca   11100
atgatattcg cggtttttcca gacgctgcgt tctatccgca attggcgaaa tcatctgcca   11160
aactcgtcgt tatgcattcg gtgcaagacg ggcaggcaga tcggcgcgag gcacccgctg   11220
gcgacatcat ggatcacatt gcggcgttct ttgacgcgcg catcgcggcg ctgacgggtc   11280
ccggtatcaa acgcaaccgc cttgtccttg atcccggcat ggggttttttt ctgggggctg   11340 ctcccgaaac ctcgctctcg gtgctggcgc ggttcgatga attgcggctg cgcttcgatt   11400
tgccggtgct tctgtctgtt tcgcgcaaat cctttctgcg cgcgctcaca ggccgtggtc   11460
cgggggatgt cggggccgcg acactcgctg cagagcttgc cgccgccgca ggtggagctg   11520
acttcatccg cacacacgag ccgcgcccct tgcgcgacgg gctggcggta ttggcggcgc   11580
taaaagaaac cgcaagaatt cgttaactgc acattcggga tatttctcta tattcgcgct   11640
```

```
tcatcagaaa actgaaggaa cctccattga atcgaactaa tattttttt ggtgaatcgc    11700
attctgactg gttgcctgtc agaggcggag aatctggtga ttttgttttt cgacgtggtg    11760
acgggcatgc cttcgcgaaa atcgcacctg cttcccgccg cggtgagctc gctggagagc    11820
gtgaccgcct catttggctc aaaggtcgag gtgtggcttg ccccgaggtc atcaactggc    11880
aggaggaaca ggagggtgca tgcttggtga taacggcaat tccgggagta ccggcggctg    11940
atctgtctgg agcggatttg ctcaaagcgt ggccgtcaat ggggcagcaa cttggcgctg    12000
ttcacagcct atcggttgat caatgtccgt ttgagcgcag gctgtcgcga atgttcggac    12060
gcgccgttga tgtggtgtcc cgcaatgccg tcaatcccga cttcttaccg gacgaggaca    12120
agagtacgcc gcagctcgat cttttggctc gtgtcgaacg agagctaccg gtgcggctcg    12180
accaagagcg caccgatatg gttgtttgcc atggtgatcc ctgcatgccg aacttcatgg    12240
tggaccctaa aactcttcaa tgcacgggtc tgatcgacct tgggcggctc ggaacagcag    12300
atcgctatgc cgatttggca ctcatgatta ctaacgccga agagaactgg gcagcgccag    12360
atgaagcaga gcgcgccttc gctgtcctat tcaatgtatt ggggatcgaa gcccccgacc    12420
gcgaacgcct tgccttctat ctgcgattgg accctctgac ttggggttga tgttcatgcc    12480
gcctgttttt cctgctcatt ggcacgtttc gcaacctgtt ctcattgcgg acaccttttc    12540
cagcctcgtt tggaaagttt cattgccaga cgggactcct gcaatcgtca agggattgaa    12600
acctatagaa gacattgctg atgaactgcg cggggccgac tatctggtat ggcgcaatgg    12660
gagggagca gtccggttgc tcggtcgtga aacaatctg atgttgctcg aatatgccgg    12720
ggagcgaatg ctctctcaca tcgttgccga gcacggcgac taccaggcga ccgaaattgc    12780
agcggaacta atggcgaagc tgtatgccgc atctgaggaa cccctgcctt ctgcccttct    12840
cccgatccgg gatcgctttg cagctttgtt tcagcgggcg cgcgatgatc aaaacgcagg    12900
ttgtcaaact gactacgtcc acgcggcgat tatagccgat caaatgatga gcaatgcctc    12960
ggaactgcgt gggctacatg gcgatctgca tcatgaaaac atcatgttct ccagtcgcgg    13020
ctggctggtg atagatcccg tcggtctggt cggtgaagtg ggctttggcg ccgccaatat    13080
gttctacgat ccggctgaca gagacgacct ttgtctcgat cctagacgca ttgcacagat    13140
ggcggacgca ttctctcgtg cgctggacgt cgatccgcgt cgcctgctcg accaggcgta    13200
cgcttatggg tgccttttccg cagcttggaa cgcggatgga gaagaggagc aacgcgatct    13260
agctatcgcg gccgcgatca agcaggtgcg acagacgtca tactagatat caannnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
```

```
nnnnnnnnnn nnnnnnnnnn nnnnnnnnnn nnnnnnnnnn nnnnnnnnnn nnnnnnnnnn   14100
nnnnnnnnnn nnnnnnnnnn nnnnnnnnnn nnnnnnnnnn nnnnnnnnnn nnnnnnnnnn   14160
nnnnnnnnnn nnnnnnnnnn nnnnnnnnnn nnnnnnnnnn nnnnnnnnnn nnnnnnnnnn   14220
nnnnnnnnnn nnnnnnnnnn nnnnnnnnnn nnnnnnnnnn nnnnnnnnnn nnnnnnnnnn   14280
nnnnnnnnnn nnnnnnnnnn nnnnnnnnnn nnnnnnnnnn nnnnnnnnnn nnnnnnnnnn   14340
nnnnnnnnnn nnnnnnnnnn nnnnnnnnnn nnnnnnnnnn nnnnnnnnnn nnnnnnnnnn   14400
nnnnnnnnnn nnnnnnnnnn nnnnnnnnnn nnnnnnnnnn nnnnnnnnnn nnnnnnnnnn   14460
nnnnnnnnnn nnnnnnnnnn nnnnnnnnnn nnnnnnnnnn nnnnnnnnnn nnnnnnnnnn   14520
nnnnnnnnnn nnnnnnnnnn nnnnnnnnnn nnnnnnnnnn nnnnnnnnnn nnnnnnnnnn   14580
nnnnnnnnnn nnnnnnnnnn nnnnnnnnnn nnnnnnnnnn nnnnnnnnnn nnnnnnnnnn   14640
nnnnnnnnnn nnnnnnnnnn nnnnnnnnnn nnnnnnnnnn nnnnnnnnnn nnnnnnnnnn   14700
nnnnnnnnnn nnnnnnnnnn nnnnnnnnnn nnnnnnnnnn nnnnnnnnnn nnnnnnnnnn   14760
nnnnnnnnnn nnnnnnnnnn nnnnnnnnnn nnnnnnnnnn nnnnnnnnnn nnnnnnnnnn   14820
nnnnnnnnnn nnnnnnnnnn nnnnnnnnnn nnnnnnnnnn nnnnnnnnnn nnnnnnnnnn   14880
nnnnnnnnnn nnnnnnnnnn nnnnnnnnnn nnnnnnnnnn nnnnnnnnnn nnnnnnnnnn   14940
nnnnnnnnnn nnnnnnnnnn nnnnnnnnnn nnnnnnnnnn nnnnnnnnnn nnnnnnnnnn   15000
nnnnnnnnnn nnnnnnnnnn nnnnnnnnnn nnnnnnnnnn nnnnnnnnnn nnnnnnnnnn   15060
nnnnnnnnnn nnnnnnnnnn nnnnnnnnnn nnnnnnnnnn nnnnnnnnnn nnnnnnnnnn   15120
nnnnnnnnnn nnnnnnnnnn nnnnnnnnnn nnnnnnnnnn nnnnnnnnnn nnnnnnnnnn   15180
nnnnnnnnnn nnnnnnnnnn nnnnnnnnnn nnnnnnnnnn nnnnnnnnnn nnnnnnnnnn   15240
nnnnnnnnnn nnnnnnnnnn nnnnnnnnnn nnnnnnnnnn nnnnnnnnnn nnnnnnnnnn   15300
nnnnnnnnnn nnnnnnnnnn nnnnnnnnnn nnnnnnnnnn nnnnnnnnnn nnnnnnnnnn   15360
nnnnnnnnnn nnnnnnnnnn nnnnnnnnnn nnnnnnnnnn nnnnnnnnnn nnnnnnnnnn   15420
nnnnnnnnnn nnnnnnnnnn nnnnnnnnnn nnnnnnnnnn nnnnnnnnnn nnnnnnnnnn   15480
nnnnnnnnnn nnnnnnnnnn nnnnnnnnnn nnnnnnnnnn nnnnnnnnnn nnnnnnnnnn   15540
nnnnnnnnnn nnnnnnnnnn nnnnnnnnnn nnnnnnnnnn nnnnnnnnnn nnnnnnnnnn   15600
nnnnnnnnnn nnnnnnnnnn nnnnnnnnnn nnnnnnnnnn nnnnnnnnnn nnnnnnnnnn   15660
nnnnnnnnnn nnnnnnnnnn nnnnnnnnnn nnnnnnnnnn nnnnnnnnnn nnnnnnnnnn   15720
nnnnnnnnnn nnnnnnnnnn nnnnnnnnnn nnnnnnnnnn nnnnnnnnnn nnnnnnnnnn   15780
nnnnnnnnnn nnnnnnnnnn nnnnnnnnnn nnnnnnnnnn nnnnnnnnnn nnnnnnnnnn   15840
nnnnnnnnnn nnnnnnnnnn nnnnnnnnnn nnnnnnnnnn nnnnnnnnnn nnnnnnnnnn   15900
nnnnnnnnnn nnnnnnnnnn nnnnnnnnnn nnnnnnnnnn nnnnnnnnnn nnnnnnnnnn   15960
nnnnnnnnnn nnnnnnnnnn nnnnnnnnnn nnnnnnnnnn nnnnnnnnnn nnnnnnnnnn   16020
nnnnnnnnnn nnnnnnnnnn nnnnnnnnnn nnnnnnnnnn nnnnnnnnnn nnnnnnnnnn   16080
nnnnnnnnnn nnnnnnnnnn nnnnnnnnnn nnnnnnnnnn nnnnnnnnnn nnnnnnnnnn   16140
cgatagtttg tcacgggca tcatccggga gcctggcgac aaaggattgg tcgattttca   16200
atgtggtgat ggggcagcat ttcagatgtt gcaggcagga atagccggtg ccgaagtcgt   16260
cggcggcgaa gcgcacgccg atggcgcgca aggcgtcgaa actggcgaac agggctggat   16320
tgccgaatgc gaccgattcg gtcagttcga tctccagaag ctcggcgggc agggccatat   16380
```

```
cggccagcac ccgctttacc tcgtcgtcga acgttggccc aacctggctg gcggacacat   16440
tgatggcaag acggaacggt tgccatgccg gtccttgcca cttgtgcatc tggcgacagg   16500
cctcgcccag cacccacgcg cctatttccg gcatcaggcc gaacgactcg ccagcggca    16560 ggaactggcc gggcggcaac aggccaagcc tcggatgccg ccagcgcatc aacgcttccg   16620
cgccagcgat ccggtgatcg cgcagatcga ccagcggctg gtaatgcagg tcaagctgtc   16680
cgcgcgccgc cgcctgcgcc aactcggccg ccgtccatcc ggcgggctgc gaactcgtca   16740
tgatccgccc cggaaggcgc gcagcagccg cgttacggcc agaacgaaca agccggtcag   16800
cgcgagcgcg gcaacacccc aatgctcgcc aaggaaggca ccggcggtcg tcccggccag   16860
cacggcggcg agaatcggca gatggcaggg gcaggtcaac acggcagcg caccccacag    16920 gtagccggaa acgggttggc gcgtctcggg cggcagtttg tcaggggcgt tcacggcaat   16980
gcctcctcgt gcgcccgctc ggctggcatg gaggccagtt gcgcgtccag atgggccaac   17040
gccgcgcgcc gccgctcgac caactggcgc agcacggcaa gctgcgctgc ggcttgtgcg   17100
ccgtccgctg cgtcgagcgc acggcacagc cgcgccaggg catccaggcc gatacccgcc   17160
tcgaaggccg cgcgcacgaa gcacagccgt gcaaggccg catcgtcgaa cacgccgtag    17220
ccgcccgtgg tgcaggccac cggccgtaac aagccgcgca ccaggtagtc gcgcacgata   17280
tgtacgctca ccccagcgtt atgggccagt tgcgataccg tgtaggcgct catcgcacac   17340
ctccttgtcc tcacccggcg cagcaggaaa gctgcttcac atccttgttg aaggtctgcg   17400
ccgcgagctt caacccttcg accatcgtca ggtaggggaa caactggtcg gccagttcct   17460
gcaccgtcat ccggttgcga atcgccagtg cggccgtctg gatcagttcg cccgcttccg   17520
gggccactgc ctgcacgccg atcagtcgtc cgctgccttc ttcaaccacc agtttgatga   17580
agccgcgcgt gtcgaagttg gcgagcgcgc gcggcacgtt gtccagcgtt agcgtgcgac   17640
tatcagtttt gatgccgtca tggtgcgctt ccgcctcgct gtagcctacg gtcgccactt   17700
gcgggtcggt gaacaccacg gccggcatcg cggtcaggtt cagggccgcg tcaccgccgg   17760
tcatgttgat cgcggcgcga gtgccggccg ctgccgccac atagacgaac tgcggctggt   17820
cggtgcagtc gcctgcggcg tagatgtgtt ccacgcttgt acgcatgccg gggtcgatga   17880
cgatagcgcc ttgcggggtg agcgtgacgc ccgtcgcatc cagtgccagc ttgcgtgtgt   17940
tgggcgcgcg gccggtggcg accagcagct tgtcggcgcg cagttcgccg tgcgccgtgg   18000
tgagcacgaa ttcgccgtcc ccttcaccat tgatatacgc gacctggctg gcctgggtgt   18060
gttccctcac ctcgatgccc tccatgcgga atgcggccgt gacggcttcg cctatagctg   18120
ggtcttcgcg gaagaacagc gtgctgcgag ccaggatcgt caccttcgct ccgagtcggg   18180
cgaacgcctg cgccagctcc agcgccacca ctgatgagcc aatcacggcc aggcgcttag   18240
gaatcgtctc gctgaccagc gcttcagtgg aagtccagta cggagtgtct ttcaggccgg   18300
gaatcggcgg cacggccggg ctcgcgccgg tggcgatcag gcagcggtcg aatgccacca   18360
cgcgctcgcc gccgtcgttg agttcacga tcaggttgcg attgtcctta aagcgggcgg     18420
agccgtgcag cacagtgatc gccggattgc cctccaagat gccttcgtac ttggcgtggc   18480
gcagttcatc gacgcgggcc tgctgctggg ccagcagcgc cgtgcgctgg atggtcggcg   18540
tggtagcggc gatgccgcca tcgaacgggc tttcccggcg cagatgggcg atatgggcgg   18600
cgcggatcat gatcttggac ggcacacaac cgacattgac gcaggtgccg ccgatggtgc   18660
cgcgctcgat cagcgtgaca cgtgcgcctt gctcgacgcc cttcagcgcc gctgccatcg   18720
cggccccgcc gctgccgatg acggcgatat gcaatgcgcc gctgctaccc gtcttgtcgt   18780
```

```
ttctgcccag cagatcgcgc atcttgtcga gcaatccgcc cggcgtcgaa actgagggggg   18840
catcggccag cgtggcccga taaccgagtc cagctacagc ggccgtcagc cgtcgggtg    18900
acgtgccgac ctcaatggcg agcttggcgc tgcccttggc gtaggagaca tccgctgatt   18960
gcacgccggg cactttctcc agggcgtcct tgacatgcac tgcgcacgag tcgcaagtca   19020
tgccggtgat tttgagagtg ctcataccat cgttccttat tcgtgtgggc cgccgtgtcg   19080
cacggtcagc cgtctttcac aagcgcttgg cggggagttc gcagccgtcc ggtccgcaac   19140
ggcgatgcgc cggcgacacg aagtcccaga tcgacacccc aatcatcaag gccaggccga   19200
cgtacatcag gttcgccgtc caccagttgc cgagcagcca gaccgtggcc gcaaacacga   19260
tggccgggcc gatcatgccg agcagactgc gcagccattg ccgatgactg aaccaaccca   19320
gcgcgttcgc caggaaggcc agcgcggcaa acagcggcag caggcggctg atgaacagtc   19380
cctcgtactg gctcaagaag cccagcccga tggccgcgcc gaagctggcg agggctggaa   19440
agcaggcggc gcagcccatc gcggaaacga cgctgccgag cgcgccggtt ttatcggcaa   19500
tgcgtgtcat cagtcccatg aagcggctct cgctgttgtc gttggcttgc tggctcactg   19560
cttgacgctg gacggatagc cggcgtctgc ggtggccttg gtcagcttct gtacgctggc   19620
cttggtgtcg tcaaaagtga cgacggcctc gcgcttctcg aagcccacat cgaccttgct   19680
cacgccttcg accttggaga gcgctttctt gactgtgatc gggcaggcgg cgcaagtcat   19740
gccgggaacc gctagcgtga cggtctgggt agcggcccac accggggcaa cagcggcggc   19800
gagggcaagg gaggcaaaca gtttcttcat gatgaactcc tggttaatag aaaaatggaa   19860
cgacatagggg aaatccaagc gcgaccagga ccagcacggc cacgatccag aaaatcagct   19920
tgtaggtggc gcgcacctgc ggaatcgcgc agacctcacc tggcttgcat gcctgcacgg   19980
gccggtaaat ccgcttccag gcgaagaaca gcgccactag cgccgcgccg atgaacaacg   20040
gtcgataggg ttccagcacc gtcaggttgc cgatccaagc accggagaag cccagggcga   20100
ccagtactag cggccccagg cagcaggtcg atgcaagaat ggcggccagc ccgccggcga   20160
agagcgcacc gcgcccgttt tgtggttcag acatacgttg gccctttttga atttggattg   20220
gatagcgtaa ccttacttcc gtactcatgt acggagtcaa gcgatatgga aaataatttg   20280
gaaaacctga ccattggcgt ttttgccaag gcggccgggg tcaacgtgga dacaatccgc   20340
ttctatcagc gcaagggcct gttgcgggaa ccggacaagc cttacggcag catccgccgc   20400
tatgggggagg cggacgtggt tcgggtgaaa ttcgtgaaat cggcacagcg gctggggttc   20460
agtctggacg agattgccga gctgttgcgg ctcgacgatg gcacccactg cgaggaggcc   20520
agcagcctgg ccgaacacaa gctcaaggac gtgcgcgaga agatggccga cttggcgcgc   20580
atggaaaccg tgctgtctga actcgtgtgc gcctgccatg cacgaaaggg gaatgtttcc   20640
tgcccgttga tcgcgtcact acagggcgaa gcaggcctgg caaggtcagc tatgccttag   20700
cgtgctttat tttccgtttt ctgaggtgcc ccctaattga gcatttccag gcgcttgcgc   20760
ctggtcaacg aaagagtcag cgccgtaggc gctgccattt ttgggggtgag gccgttcgcg   20820
gccgaggggc gcagcccctg gggggatggg aggcccgcgt tagcgggccg ggagggttcg   20880
agaaggggggg gcaccccnnn nnnnnnnnnn nnnnnnnnnn nnnnnnnnnn nnnnnnnnnn   20940
nnnnnnnnnn nnnnnnnnnn nnnnnnnnnn nnnnnnnnnn nnnnnnnnnn nnnnnnnnnn   21000
nnnnnnnnnn nnnnnnnnnn nnnnnnnnnn nnnnnnnnnn nnnnnnnnnn nnnnnnnnnn   21060
nnnnnnnnnn nnnnnnnnnn nnnnnnnnnn nnnnnnnnnn nnnnnnnnnn nnnnnnnnnn   21120
```

```
nnnnnnnnnn nnnnnnnnnn nnnnnnnnnn nnnnnnnnnn nnnnnnnnnn nnnnnnnnnn   21180
nnnnnnnnnn nnnnnnnnnn nnnnnnnnnn nnnnnnnnnn nnnnnnnnnn nnnnnnnnnn   21240
nnnnnnnnnn nnnnnnnnnn nnnnnnnnnn nnnnnnnnnn nnnnnnnnnn nnnnnnnnnn   21300
nnnnnnnnnn nnnnnnnnnn nnnnnnnnnn nnnnnnnnnn nnnnnnnnnn nnnnnnnnnn   21360
nnnnnnnnnn nnnnnnnnnn nnnnnnnnnn nnnnnnnnnn nnnnnnnnnn nnnnnnnnnn   21420
nnnnnnnnnn nnnnnnnnnn nnnnnnnnnn nnnnnnnnnn nnnnnnnnnn nnnnnnnnnn   21480
nnnnnnnnnn nnnnnnnnnn nnnnnnnnnn nnnnnnnnnn nnnnnnnnnn nnnnnnnnnn   21540
nnnnnnnnnn nnnnnnnnnn nnnnnnnnnn nnnnnnnnnn nnnnnnnnnn nnnnnnnnnn   21600
nnnnnnnnnn nnnnnnnnnn nnnnnnnnnn nnnnnnnnnn nnnnnnnnnn nnnnnnnnnn   21660
nnnnnnnnnn nnnnnnnnnn nnnnnnnnnn nnnnnnnnnn nnnnnnnnnn nnnnnnnnnn   21720
nnnnnnnnnn nnnnnnnnnn nnnnnnnnnn nnnnnnnnnn nnnnnnnnnn nnnnnnnnnn   21780
nnnnnnnnnn nnnnnnnnnn nnnnnnnnnn nnnnnnnnnn nnnnnnnnnn nnnnnnnnnn   21840
nnnnnnnnnn nnnnnnnnnn nnnnnnnnnn nnnnnnnnnn nnnnnnnnnn nnnnnnnnnn   21900
nnnnnnnnnn nnnnnnnnnn nnnnnnnnnn nnnnnnnnnn nnnnnnnnnn nnnnnnnnnn   21960
nnnnnnnnnn nnnnnnnnnn nnnnnnnnnn nnnnnnnnnn nnnnnnnnnn nnnnnnnnnn   22020
nnnnnggggg gcaccccct tcggcgtgcg cggtcacgcg cacagggcgc agccctggtt   22080
aaaaacaagg tttataaata ttggtttaaa agcaggttaa aagacaggtt agcggtggcc   22140
gaaaaacggg cggaaaccct tgcaaatgct ggattttctg cctgtggaca gcccctcaaa   22200
tgtcaatagg tgcgccctc atctgtcagc actctgcccc tcaagtgtca aggatcgcgc   22260
ccctcatctg tcagtagtcg cgcccctcaa gtgtcaatac cgcagggcac ttatccccag   22320
gcttgtccac atcatctgtg ggaaactcgc gtaaaatcag gcgttttcgc cgatttgcga   22380
ggctggccag ctccacgtcg ccggccgaaa tcgagcctgc ccctcatctg tcaacgccgc   22440
gccgggtgag tcgccccctc aagtgtcaac gtccgcccct catctgtcag tgagggccaa   22500
gttttccgcg aggtatccac aacgccggcg gccgcggtgt ctcgcacacg gcttcgacgg   22560
cgtttctggc gcgtttgcag ggccatagac ggccgccagc ccagcggcga gggcaaccag   22620
cccggtgagc gtcggaaagg cgctggaagc cccgtagcga cgcggagagg ggcgagacaa   22680
gccaagggcg caggctcgat gcgcagcacg acatagccgg ttctcgcaag gacgagaatt   22740
tccctgcggt gcccctcaag tgtcaatgaa agtttccaac gcgagccatt cgcgagagcc   22800
ttgagtccac gctagatcta tctcatctgc gcaaggcaga acgtgaagac ggccgccctg   22860
gacctcgccc gcgagcgcca ggcgcacgag gccggcgcgc ggacccgcgc cacggcccac   22920
gagcggacgc cgcagcagga gcgccagaag gccgccagag aggccgagcg cggccgtgag   22980
gcttggacgc tagggcaggg catgaaaaag cccgtagcgg gctgctacgg gcgtctgacg   23040
cggtggaaag ggggagggga tgttgtctac atggctctgc tgtagtgagt gggttgcgct   23100
ccggcagcgg tcctgatcaa tcgtcaccct ttctcggtcc ttcaacgttc ctgacaacga   23160
gcctcctttt cgccaatcca tcgacaatca ccgcgagtcc ctgctcgaac gctgcgtccg   23220
gaccggcttc gtcgaaggcg tctatcgcgg cccgcaacag cggcgagagc ggagcctgtt   23280
caacggtgcc gccgcgctcg ccggcatcgc tgtcgccggc ctgctcctca agcacggccc   23340
caacagtgaa gtagctgatt gtcatcagcg cattgacggc gtccccggcc gaaaaacccg   23400
cctcgcagag gaagcgaagc tgcgcgtcgg ccgtttccat ctgcggtgcg cccggtcgcg   23460
tgccggcatg gatgcgcgcg ccatcgcggt aggcgagcag cgcctgcctg aagctgcggg   23520
```

```
cattcccgat cagaaatgag cgccagtcgt cgtcggctct cggcaccgaa tgcgtatgat    23580
tctccgccag catggcttcg gccagtgcgt cgagcagcgc ccgcttgttc ctgaagtgcc    23640
agtaaagcgc cggctgctga acccccaacc gttccgccag tttgcgtgtc gtcagaccgt    23700
ctacgccgac ctcgttcaac aggtccaggg cggcacggat cactgtattc ggctgcaact    23760
ttgtcatgct tgacacttta tcactgataa acataatatg tccaccaact tatcagtgat    23820
aaagaatccg cgcgttcaat cggaccagcg gaggctggtc cggaggccag acgtgaaacc    23880
caacagaccc ctgatcgtaa ttctgagcac tgtcgcgctc gacgctgtcg gcatcggcct    23940
gattatgccg gtgctgccgg gcctcctgcg cgatctggtt cactcgaacg acgtcaccgc    24000
ccactatggc attctgctgg cgctgtatgc gttgatgcaa tttgcctgcg cacctgtgct    24060
gggcgcgctg tcggatcgtt tcgggcggcg gccggtcttg ctcgtctcgc tggccggcgc    24120
tgctgtcgac tacgccatca tggcgacggc gcctttcctt tgggttctct atatcgggcg    24180
gatcgtggcc ggcatcaccg gggcgactgg ggcggtagcc ggcgcttata ttgccgatat    24240
cactgatggc gatgagcgcg cgcggcactt cggcttcatg agcgcctgtt tcgggttcgg    24300
gatggtcgcg ggacctgtgc tcggtgggct gatgggcggt ttctcccccc acgctccgtt    24360
cttcgccgcg gcagccttga acggcctcaa tttcctgacg ggctgtttcc ttttgccgga    24420
gtcgcacaaa ggcgaacgcc ggccgttacg ccgggaggct ctcaacccgc tgcttcgtt    24480 ccggtgggcc cggggcatga ccgtcgtcgc cgccctgatg gcggtcttct tcatcatgca    24540
acttgtcgga caggtgccgg ccgcgctttg ggtcattttc ggcgaggatc gctttcactg    24600
ggacgcgacc acgatcggca tttcgcttgc cgcatttggc attctgcatt cactcgccca    24660
ggcaatgatc accggccctg tagccgcccg gctcggcgaa aggcgggcac tcatgctcgg    24720
aatgattgcc gacggcacag gctacatcct gcttgccttc gcgacacggg gatggatggc    24780
gttcccgatc atggtcctgc ttgcttcggg tggcatcgga atgccggcgc tgcaagcaat    24840
gttgtccagg caggtggatg aggaacgtca ggggcagctg caaggctcac tggcggcgct    24900
caccagcctg acctcgatcg tcggacccct cctcttcacg gcgatctatg cggcttctat    24960
aacaacgtgg aacgggtggg catggattgc aggcgctgcc ctctacttgc tctgcctgcc    25020
ggcgctgcgt cgcgggcttt ggagcggcgc agggcaacga gccgatcgct gatcgtggaa    25080
acgataggcc tatgccatgc gggtcaaggc gacttccggc aagctatacg cgccctagga    25140
gtgcggttgg aacgttggcc cagccagata ctcccgatca cgagcaggac gccgatgatt    25200
tgaagcgcac tcagcgtctg atccaagaac aaccatccta gcaacacggc ggtccccggg    25260
ctgagaaagc ccagtaagga aacaactgta ggttcgagtc gcgagatccc ccggaaccaa    25320
aggaagtagg ttaaacccgc tccgatcagg ccgagccacg ccaggccgag aacattggtt    25380
cctgtaggca tcgggattgg cggatcaaac actaaagcta ctggaacgag cagaagtcct    25440
ccggccgcca gttgccaggc ggtaaaggtg agcagaggca cggagggttg ccacttgcgg    25500
gtcagcacgg ttccgaacgc catggaaacc gcccccgcca ggcccgctgc gacgccgaca    25560
ggatctagcg ctgcgtttgg tgtcaacacc aacagcgcca cgcccgcagt tccgcaaata    25620
gcccccagga ccgccatcaa tcgtatcggg ctacctagca gagcggcaga gatgaacacg    25680
accatcagcg gctgcacagc gcctaccgtc gccgcgaccc cgcccggcag gcggtagacc    25740
gaaataaaca acaagctcca gaatagcgaa atattaagtg cgccgaggat gaagatgcgc    25800
atccaccaga ttcccgttgg aatctgtcgg acgatcatca cgagcaataa acccgccggc    25860
```

```
aacgcccgca gcatcgcgac cgtcatcggt gagaagttcg gcaggtattg ggtggtgaca   25920
atgtaggtgc tgccccaaat ggcaggtgct atcgctgtga acaataaatc ggggcagacg   25980
gcgcttccag cgtgacgacc atgccgagca cgcagcgggt gaacacgtcg atggcgaggg   26040
tcaggtacgg gcggccaata ggttgccggt cgcggtcatc gaccacgatc aggtcgatga   26100
ccgtatggtc tatctgcacc tgctccagcg gcgcggtcac ggcaggaggc tcgccgccca   26160
caccttgtag gtcacgagcg gcatcctggc cttcccgccg gcggatgacc ttgcgcgggt   26220
caaggctagc gatccgtaag gccacggtat tgcgcgccgg cactcgcagt ttttgagcct   26280
tgcacacctg agtgacttcg cggtgaaagg ccgctaggct gcgcttctgc ttggtcagga   26340
accgcttttg cagtagctcg tggatgacgc gctcgaccgg ttccggcaag cgccccttac   26400
ctttacctcc accggactgg ccgggcacca gatccgtcac gaggccgctg ccttgccggg   26460
cacgccggat cagaacgtat acctggcgcc gagacaagcc cagcgcctga gccgccatat   26520
cggccgcttc gtgcccgacc gtctccgact gcgccaacgg actgatgatc tccgcacgac   26580
ggcgcgcacg ctcccaagcc tcatcaggca gagtggccac gccttgttct ggaatccgtg   26640
gggtgtccgt cgccatgctc acctcgcttt ggtgcacacg agtattgagc atagtcgaga   26700
ttggtgcaga tcacttctga tattgaactg tcaggagctg gctgcacaac agccattacg   26760
cccaatcaac tggtgcagtc gtcttctgaa aatgacatcc atgcccagcc cgtgcgcgag   26820
ctggatcacc gcccgcagtg ctacggggat ttattgcaga gcggtatgta cgaggtctgt   26880
ttacagctac cagccagact tgtttgagga ctgcggaggc gcgagtactt aatccaaaat   26940
cgccgctctg cgcagggcgt tcagaggtat cgcaacctgc attttatccg gtgtttcgca   27000
cctgccccgt tcgtgacaca acggcgcgac accggatatc cgcagtcctg cttacctgaa   27060
taaaacccgg ggtattgatt ggtagtgtgg tgcggaatcg tactgtgatc tcgcattcgc   27120
cgaattcgca ctgtggtgtc aatcaaccat acgtgagagt cctctccgta tttatcagtg   27180
cctcaggacg atttctgcat agttaatcca ggggctgcaa ggccgccttc tgttgcgcac   27240
tcagggcatg taaatcatgc tcaaaccacg ccccttgagc atctgtctgc aaaatcaacc   27300
ggccacgaca ggaaaggcag aaacaatgcc ggatatttct gctgagcgca gagttggcac   27360
tgataatgtg ctcacccggc gtgatcccca gccccatttt tatgccgttc atcctgctac   27420
cacctcctca ctgaagcgcc cggtctggca gtgtgtgcag taccgctccc cataataatc   27480
gtggtgacat tgtctgcagt gccagctggc tttacgcacc acgggtaagg catccggtac   27540
gaattgctgc agacgctgaa tcaagcgtac ctccctgcgt tccggtctga cataaggaca   27600
ctgctgaccg tgcgctgtca gcccgtcgtc agtgtgttca aaccagggac gttcagtgtc   27660
gtattgcggg tggtatctga gtgcactgcc gcaaaggtgg caggtgtagc gatcataagg   27720
tgcagtctgt gcggtacggg caccggtcag acgtccgttg ccatcaagtg cgagaaaaga   27780
ttttgcgtac atagtatatg ttccttagcg ccagacgaca cgcaggcaac agccgtcccg   27840
gtacgggcag cctggtctgg tgtgaatggc ggtttcagtc cggtctcaga agggaaaatc   27900
agtgtggtgg ccgtgagcgc gtcatcacac tgaggtcaga taactcgtct gtcgggctca   27960
gctacgactg cagccaaagt tgcgctcacc agtggcgtga gctttggtat gttccttcgc   28020
cagatagtca gcacgttcca gcacctgctg aaagccagtg tcatcatcgc gttccagcca   28080
caccgccgac gtgtcaggaa aatgcgccaa cgtggcataa gcccggcat ccaccccag    28140 ggcactgcac caggcctgtt taatcatccc ggccagtgat ctcggagcgc ggtaatcgcc   28200
ggcacgacac caggtatccc ggttgaccag cagcaggagg tgatagtgtt ttttgccttt   28260
```

```
aagctccccg aattcccggg cccaggcgta atgcagggtc gtgggatgta cgcgtttacc   28320
ttcacggcgc ttacgcttct ggtaagcgtt gattcgggct ttcagggcat tgatgaagcg   28380
ggatatcaca gctgcgtccg ttgctgccgg tacatccggg agacgcaggt caacccgcaa   28440
tgccgtcagg cggggatgaa catccagtgc gcgcagcacc gtctcaccga tacgttgttg   28500
ccagaagggg ttgtactcgt gtgtcatggt taaatctccg tatggtttcg ttcatacgga   28560
ataaccacgc tgtaaaaaat gtgcagagtc cctgaagtga tctccaaccg ggcaatgtct   28620
caggcactca gtgataccccc gactgtcgtc tccggactga cggttgaatt ttcagcgttg   28680 ttttttttaat gcaaaaaacc ggttacggat aaaactgtga ggagggcgtt atggtgatac   28740
gcaaaacggt gtgcagggat tgtagtaacg caattactca taatacggaa tgctgcccga   28800
gctgcgcgtc aacagcttcc tcaggctatt accgaaatac cgatcgtctg ctctttctac   28860
tgacgttact gcctgtgctg attctggctg tcgtttcaga cgtcagtgta tttgtactgt   28920
tgcagtaggt tacaggggag ggattatccg gaatcaacgg ggcagaacgc cccgccgcct   28980
ctgcgtttgc tgtgccagac agtaacgcac cggatccccg gtaaatacga gaaaacctca   29040
gcagatacag gccgttaata cccgaaaatc agcccatgat cacccacacc tccgacacc    29100 attccctttt gatttcgaat tctttgttgt cgttatacag cttaacgttc ccgacattat   29160
cctggttccc gacaacagga acatattcag cttttaataa cctgagaaga gccaataaga   29220
atcacaaagc ggataacacc tggcgcgatg ccgttgtgat taccgaacgc tcagatgaca   29280
tatttccaga ctgaagcggg aacacgatcg taaagcttgt tcattgtcag ttctgccagt   29340
cggtgatcga ccgcagagtt gaaggtttcc agctccgcag gggtaagttt ataacgcgtg   29400
tgggaaatca cttttccagt gtctcccggg atgaacaacg acggaactga tacagccagt   29460
cctctttggt tttaacttcc attagcctct catcacttta tgctacaatt aacgtgatac   29520
tgtcagcata ccgcaccaga ctggcattct ggtaccctcc ccaaactcat tactcccggg   29580
ccaccactta accggtctct cagactgtca ctcaccaggt cggatacgct taccgctcag   29640
acggatgctt aatgcactct gttcacgtgg gttgcaggta cgttttatat acgcaggtta   29700
tacgccagct atcagagata gccctgtggg tacaacgcaa tctgctgcta ctgcgttctc   29760
atgcccactg atcgcactca cagtgtttat ttcacatata tgaactcatg tgtttgatct   29820
ctcttatata tttataatac caatcagaca gtcttatccc aacagtgata cctgtccctg   29880
cccacaaggc acgggctgcc ccaccgtaac cgccccgtaa ataactctgc aattatcaga   29940
acgccagttt tcccctcttc ctcacgaaaa tcatcccttc tttatcgcgc gcgcgtgcgg   30000
aagcatcgtt tcgtaacaac cacccggcat accggtacgg ctcagccacc gcaacctccc   30060
cgtttatctc ctggcggtca cattcccgat tattttttac gtttctcccc ggttgttatg   30120
ccggtgaagg tggtgcgttg ttttcatgac cacaccggct ggtttaacaa catccggagg   30180
aacattctca tgaccacccc agtttcgctg atggatgacc agatggtcga tatggcgttt   30240
atcactcagc tgaccggcct gaccgataag tggttttaca agctcatcaa ggatgggggcc   30300 tttccggctc ccatcaaact cggccgcagc tcccgctggc tgaaaagtga agtggaagcc   30360
tggctacagg cgcgtattgc acagtcccgt ccgtaatttc tgccccttat ccgttcaccc   30420
gcagcagacg taatcccccgg cctgccgacg gcattctgct gcctgttata tccccgtgag   30480
gaatatgaaa atgaaacaac agtatcagac ccgctacgaa tggctccacg aaagctacca   30540
gaaatggctg accggcttca cccggcacgc cgtatcctgg ggcgtgtgtc atccgaatat   30600
```

```
ctactacttc cataatctga cgcccggttg ggtgtcattc aatggtgaaa aaccggagat    30660
tgccatcgtc ccccagagcc tgcaccggct gatttatggc cctgacaaac gggccacgcc    30720
gcccctggat gatgatctga tagtgaattt atgcaccagt gaacatctgc tggttcatca    30780
tccgatgctg gaaggcattc tgctgtctga atgtgaacgt ctgaaacacc attctctggc    30840
aaataaactg atcagtctct tccgtcagtt tggtggcacg gagttacgcc ttaaactggt    30900
ctggctttgc tggcttgatt taatgaccgg aaacagcctt gaagactgga cagagaacct    30960
gaaacggaaa tcagaaaaag agctggagga atggatcatc gaccgtcaga agcagagcgc    31020
agcactgacg gatctgatgg atcagtacgt gctcctggca taccgcacaa cggttgacga    31080
taaccgtaac tgatgccggt tgcttccgga aggtgcggca aaatacggga atgatgcttc    31140
cggccccaca tactcacctg cagagcgtgt tcgtcgtcat catactgagc catgacggat    31200
ggcttaaggg catcctgtca ttgctgaact ggcatgaaca ccaccagtga atgaaagc     31258
```

<210> SEQ ID NO 3
<211> LENGTH: 13399
<212> TYPE: DNA
<213> ORGANISM: Escherichia coli
<220> FEATURE:
<221> NAME/KEY: misc_feature
<222> LOCATION: (5292)..(5292)
<223> OTHER INFORMATION: n is a, c, g, or t
<220> FEATURE:
<221> NAME/KEY: misc_feature
<222> LOCATION: (5296)..(5297)
<223> OTHER INFORMATION: n is a, c, g, or t
<220> FEATURE:
<221> NAME/KEY: misc_feature
<222> LOCATION: (9219)..(9220)
<223> OTHER INFORMATION: n is a, c, g, or t
<220> FEATURE:
<221> NAME/KEY: misc_feature
<222> LOCATION: (9236)..(9236)
<223> OTHER INFORMATION: n is a, c, g, or t

<400> SEQUENCE: 3

```
catggtggca gccggttaac tttcctgcgc caccagtgga aaaaggccat aagcagtccg      60
aacaaaagta agcgtacagc gagggccgta ttgacgggga tgtgttattc agctggcagt     120
gctatgcgcc acggaagcag ttcgctgacc cggttgaccg gccagtctgc tatgacgcca     180
gacacatggc gaaggtagct ttctggatcc acgtcattca gtttgcacgt cccgatcagg     240
ctgtacagta gcgctccccg ctcaccacca tggccagagc cgaagaacag ggtcttcatc     300
ttttcacgca accagctttc cagggatttc aacagcggtt tcgttttttcg ctgacgttca     360 gcaagccgct gctctgccgg cattcccctt atatccgcct ctatggcgta caactgaccg     420
atctgctcca gggcttcttc cgtcagtgct gacgggatgc ggacgtgcac atcgtggatc     480
tttcggcggg catgagccca gcaggcagct tccgttatcc saccattgcg atacagctcg     540
ttgaacccgg cgtatgcatc cgcctgcagt acaccactga accccgcaag atgggtctgc     600
ggatggatgc cttttctgtc cgggctgtaa gcgaaccaca ccgcmggygc carcgctgac     660
ccggcattgc ggtcatcacg aacatacgcc cacaaccgcc cggtcttcgt cttcttatta     720
cccggcagca gtacctggac cggggtatca tcggcatgga gtttgccgtc agtcatgaca     780
tagccatgaa gcgcctcttc cagcggagac agcagccggc agcatgcatc cacccagccc     840
gacagcagtg aacggctcag ctccacacct tgccggccgt atatttctga ctggcaatac     900 agcgggggtgt gctctgcata cttcgaggtc agcacgcggg ccagcagccc cggtccggcg     960
ataccccgct cgatgggccg cgaaggtgca ggtgcctgca cgatggcatc gcactgagta    1020
```

```
caggcatgtt tttcccgtac cgtccggata acccggaagg cgctacgcat caactccagc    1080
tgttcggcgg tatcctcgcc cagatagctc agtgaaccgc cgcagttcgg gcagcacggc    1140
gccgcaggca acagtcgctt ttcgtcacgg ggtagtgatt cagggaacgg cttacgggtg    1200
cgggtctgac gcaacggacg ctgtactgcc gggtcataca ccctaccagt cagcgtatcg    1260
ctctctttct gaagccggtt cagatcggct tccatttgtg cgatacggcg ggagactttt    1320
tcggaacgac tgccgaagtt catccggcgg agtttatcca gctgcgcctg cagatggtct    1380
atttcgcgct cccggttgct cagcttttcc tgcagggcgt ggatcagcgc ttcctgttcg    1440
gccaggcgct gtttcagcag gaagatgtcg tcagaagaga tgtcgttcat aagcccgtat    1500
tttaccgggc ttattctgtg acaaccagga taaagagatt tacagcatgg tcaggaggt    1560 cagcagccgc ttgggctgtc gccagtcgat accttccagc agcatcgcca gctgcgcctg    1620
cgtaaggaac actttgccat cacgggctga cggccaggcg aagcgcccac gctccagccg    1680
tttggtcagg aggcacagtc cgtcaccggt ggaccacagc agtttaacct gactgccgct    1740
gcggccccgg aaaatgaaaa catggccgga catgggatcg tctttcagcg ccgtctgtac    1800
tttcgcagcc aggccgttga agccatttct catatcggtg ataccggcaa ccagccaaat    1860
tttggtcccg gaaggtaacg ggatcatcgc ttcagttcct gtatcagcag agtcaggagc    1920
ttttcgctga cattgccatt gaagcggagc gtcccgtgcc ggaacgttac ctcacagctg    1980
atactgaggg tttccgggtc ctctgcgagc gattctggct gttcggcagc tgcatcgaga    2040
gtcacaggaa gtagctgggg gctctctgaa gaaggtaata gcagctttcc ctcacgcaat    2100
tgttgtcgcc atttgaacaa cagattggcg ttaatgccat tttcaagagc aagttttgag    2160
atggatatcc cgggttcaca ggaggcagca acgagctgct gtttaaattc gggaggataa    2220
ttagggcagc cttttcgcct gccgggagtc acattttttct gcatatctga cactttggtt    2280
cccactactt atttggtgga caccactttg tctaattcgt cagattctga ccagacggtt    2340
caggctgtac gcttaccact attttatccc tgttgaattt ggttaagccg gtgcagacga    2400
gccgggaaac gcacatctga accggcacaa taaaatacaa tacaaccccc tgttactgga    2460
gatacgaatg gaatgacgag gcagcctgtc agtcacaggg ggctgttggc ataaaatcaa    2520
cggaaaggcc accaacaccg gaattaagct ccacagtccc cgcactggca atccattccc    2580
gggaaaggca ttaccgcaaa ctgctccgga ggcaaccatt acagcctcag taacggatta    2640
tcagccctgg catcttccga cggcacctcc tgccgccccc acgccctgct gtataccccg    2700
gtaccgcagc gtgggcagca ctttcccccc tcataatctt cgtcacacat cacacaaaac    2760
cactttctca ccttcaccgt ataatccgga accgtcatgc cctgcagatg caaacgacgg    2820
gcctctttct ctgccgggtc aagccaggta catcgcagca ggattttttc agcgacagtc    2880
atctggtcat gttcaaacca cggtggttgt ccgtcattgc cccgctgaag tgttaacggg    2940
catccacagg acacacagca caaaacgtcc tgtcggttgt gcttcgcagc ttctttcgcc    3000
gtaacaaaat ggcctttgct gtcattcgcc atataacagt tcagaattcg catatttcct    3060
cctgagttgt ccggggaata ctgaatcctc cggtctggca gtgtgtgcag tactgctccc    3120
cataataatc gtggtgacat tgtctgcagt gccagctggc tttacgcacc acgggtaagg    3180
catccggtac gaattgctgc agacgtttaa tcaactgtat ttctctgcgc tccggcctga    3240
cataagggca ctgttgaccg tgctctgtca gcctgtcgtc agtgtgttca aaccagggaa    3300
gttcagtgtc gtattgcgga tggtatctga gtgcactgcc acacaagtgg caggtgtagt    3360
```

```
tagcataagg tgcggcctgt gcagtacggg cgcccgtcag acgtccgttg ccatcaagag    3420
cgataaagga ttttgcgtac atagtcatat acctcagccg ccagacgaca cgcaggcaac    3480
agccgtcccg gtacgggcag cgtggtcagg gtgtgaatgg cggttcagtt aaaatctgga    3540
ctggagtttg ggtaaagcag gctggttgct gttacagcac tgtggttgtc acacaatgga    3600
acactgacgt aaaaaacagt cagtgggcga gtggatacat cgttgccgcc agacaacaac    3660
ccatactttt ggtttgccgg atattggcgc gccagtcgtg ctcaactccg gctacagcca    3720
aaattgcgct caccggtgca gtgagctttg gtatgctcct tcgccagata gtcagcacgt    3780
tccagcacct gctgaaagcc ggtgtcatca ttacgcgcca gccacaccgc cggccaggcc    3840
ggaaaatgca ccagcgtggc atggcacccg acatccactc ccagggcact gcaccacgcc    3900
tgtttaatca tcccgccagt agactccgga gcgcggtaat caccggcacg acaccaggta    3960
tcccggttga ccagcagcat caggtgatag tgttttttac ctttgcactc cccaaactcc    4020
cgggcccaga cgtaatgcag ggttgtggga tgcacgcgtt taccttcccg atgcttacgt    4080
ttctggtaag cgtcgattcg ggcttcagg gcattgatga agcgggatat cacagctgcg    4140
tccgttgctg ccggtacatc cgggagacgc aggtcaaccc gcaatgccgt caggcgggga    4200
tgaacattca gtgcgtgccg caccgtctca cgaatacgtt gctgccagaa ggggttgtat    4260
ttgtaggtca tggttaaatc tccgtatggt tcatacggaa tagccacgtc gtaaaaaata    4320
cgcagagtcc ctgaagtgac ctccggcagg acactgtctc aggcactctg tgataacccg    4380
aacggtcgtc tccggactga cgattgaatt cccggcgttg tttttttaa tgtaaaaaac    4440 cggttacgga taaggcgtgg cgaggagct atcgtgatac gcaaaagaa atgcggggat    4500 tgcggtaatt cgattactca taatacagtg tgttgcctgt attgtggcgc tgtcgttcct    4560 tccgttatt accggaagac cgatcgtctg ctctgtttac tgagttactg ctggtgctga    4620
ttctggttac cgtttcaggc gtcagtgtat ttgtactgtt gcagtaggtt actggggagg    4680
gattatcagg aatcggcgga gcagagcgac tcgctgcgtt tgttgtgcca gacagtaacg    4740
caccggatcc ctgcaaaatg gtacctgaat caatcacagt taggtattcc gccaatccgt    4800
gatcgaatcg agcggaatac gcagcccga caaatacgag ccccccttcag cagatacagg    4860 ccggtaatac ctgaaaatca gcctattacc gcccacgcct ccggcaccat tcccttttga    4920
tttcgaattc tttgttgtcg ctataccgct taatgttccc ggcacctccg gtgcagataa    4980
caccggagtc atcgtagcgc tgcttcaata ttcaggtgac atatttccag acggaagccg    5040
gcgcgcgatc gtaaagtttg ttcattgtca gttctgccag ccggttgtca acggcagagt    5100
taaaggcttc cagctccgca agggtaagtt tataacgcgt gtgggaattc acttttcccg    5160
cgtctcctga cgtattacgg gctgccactt accaggtgtc ccgcaataca gccttagtgt    5220
tccgttatcg gggatccgga cgcaccgcaa caaccgggga agtatttctg gtttagagca    5280
gtgtcaagag gnattnntca gccccctcact crcckgckca gtctcaggca ggagcattaa    5340
tacgctcagt tcatgtctta tacaggaatg ggcacagggg gagctggcgt gtcactgctg    5400
attttacgca tcagcgttca tgtatctgca ctctgataca tgaacgattc acagcgctct    5460
gttaccggag agatttactc tcttagctta ctctggcaaa tcctttacgt tactctctga    5520
tgacttctta tatttataat accaatcaga cagccttatc ccatcggtga tatcagtctc    5580
ctcctcgcca ggaacgggct gactcactgt aaccaccacc gaaaacaact ctgcaattat    5640
cagaacgcct gcttctctcc ctgtcctcac gaaaactatc cctctttat cgcgcgtgcg    5700 tgccggaagca tcttttcgca acaaccaccc ggtataccgg tacggctcag ccaccgcaac    5760
```

```
ctccccgttt atctcctggc ggtcacattc ccgattattt tttacgtttc tccccggttg   5820
ttatgccggt gaaggtggcg cgctgttttc atgaccacac cggctggttt aacaacatcc   5880
ggaggaacat tctcatggct accccagttt cactgatgga tgaccagatg gtcgacatgg   5940
catttatcac tcaactgacc ggcctgacag ataagtggtt ttacaggctc atcagggatg   6000 gggccttttcc ggctcccatc aagctgggcc gcagctcccg ctggctgaaa agtgaagtgg   6060
aagcctggct gcaggcgcgt attgcacagc cccgcccgta atttctgacc gttatccgtt   6120
cacccgcagc agacgtaatc cccggcctgc cggcggcatt ctgctgcctg ttatatcccc   6180
gtgaggaata tgaaaatgaa acaacagtat cagacccgct acgaatggct ccacgaaagc   6240
taccagaaat ggctgaccgg cttcacccgg cacgccgtat cctggggcgt gtgtcatccg   6300
aatatctact acttccataa tctgacgccc ggttgggtgt cattcaatgg tgaaaaaccg   6360
gagattgcca tcgtacccca gagcctgcac cggctgattt atggccctga caacgggcc   6420 acgccgcccc tggatgatga tctgattgtg aatttatgca ccagtgaaca tctgctggtt   6480
catcatccga tgctggaagg cattctcctg tctgaatgtg aacgtctgag gcagcgttct   6540
ctggcaaata aactgatcag cctcttccgt cagtttggtg gcacggagtt gcgcctcaaa   6600
ctggtctggc tttgctggct tgatttaatg accggaaaca gccttgaaga ctggacagag   6660
aacctgaaac ggaaatcaga aaaagagctg gaggaatgga tcatcgaccg tcagaagcag   6720
agcgcagcac tgacggatct gatggatcag tacgtgctcc tggcataccg cacaacggtt   6780
gacgatagcc gcaactgatg ccggttgctt ccggaaggtg tgacaaaata cggaaatgat   6840
gatgagctcc cggccccgca tgctcacctg cagagcgtgt tcgtcgtcat catactgagc   6900
catgacgggt gtcttaaggg catcctgtca ttgctgagca ggcaacacca ccagaggagc   6960
cacggacagg gatgttcttt acagccmgat acacgccagg ttctcagcag actgaatgtg   7020
caggtgcggt tattcaccag aaatggcatg ctgcggtaca tacccatcct ggtgacaata   7080
tgtacgtggc gacagcgatc ccggcactgt ggaagagact cactcagcct gcaggatatt   7140
ctttccggca tccgggaatg tccgcctgaa tgcaaacagg atgatatttg aatccgtaat   7200
actgttcttt catcataaat aatttatgca gatacagtta accgttacag tagccggttt   7260
gttttaccgg gaaataatat ccgtcagact gatgccggaa catatctgaa acacgttatg   7320
atgttttgtt atcagaaatg ttgtatattc ttatccgtgg cgacagttta atgccctctg   7380
gtatcacctg ataatgcata tcctgcgatg attcgttata tttacgggac acgcctcttt   7440
tcattgtgct ccttttcaga cttcatttttc cgtaagtgtt ccccggcata aaggaggtac   7500
ctttctggcg tttataactc tctttatcgg tgacgccggt aatacaggga ataccacacc   7560
gacaaacgag gtattaacag acgatatttc agtgtccata atttttctgt ccggttaaat   7620
aacgtcagtc tgctgccctc tgactgtaat catcaaagcc ggaatgcata ccgggttaca   7680
acgtaaaaaa agtgatgctg gccccggtg cagctggcgg gcgaaacatg tttacctttc   7740
aataccccct gtctgcagtc tccactcttc catcctctta agctacgtcg gccacatgag   7800
tgcacttcca tgataacagg tattcctgtc agcataacga agccggttac cttcccttcc   7860
tcctgcattt cctgtcagaa tgactgtaca gcgcgcagat tgccttttta ttgaccacct   7920
taacatacca ttataaactt ctttttatca tgttattatc accttattat gtttaatttt   7980
caagcaaccg gagaaagagg atggttcaga aaatttgtc ggataaggtt atgaatgaaa   8040
gagcaaatgc gtattactct tattatcttg gagagcgtaa tatctccgta ctgccccta   8100
```

```
atgtttatga tcccccggaa cgttttatcg cttacataaa aaaaacagag aaaatctgaa    8160
catcacactt tcagattttg aacttgaaca aatcatttct ggtatgcgtc tgaaggccct    8220
ggccttcctg gtcccctgg aaaaaatatc ctggatcgcg ggcagtgaac gcgcatgctt    8280
attttcctgg tatctgttga tgcagtttat ccagaataac agggcaaaaa taagcgcaga    8340
cttgcttcaa aagaataaac tgtatcttaa agaagagtat ctggaaggga atgccttccc    8400
gtcggactca tcgacacagt tcagacaaat actcagagtt ctcgatattc tttctgataa    8460
gaatttgcgg gatgagtgga taatccagac caaagacaga tggatacggg catttaaatc    8520
aaagagtcct ttcagttacc tcctcccgga gaacgaacat gaatgcatat ggacatggaa    8580
ttatttgaag ggaaaaaata ttgcactgga aaaactggcc agttttcctg gttctgctga    8640
tatttaccac gcaattcacc tttcatttga caggtaatga ctccaactta ttgatagtgt    8700
tttatgttca gataatgccc gatgactttg tcatgcagct ccaccgattt tgagaacgac    8760
agcgacttcc gtcccagccg tgccaggtgc tgcctcagat tcaggttatg ccgctcaatt    8820
cgctgcgtat atcgcttgct gattacgtgc agctttccct tcaggcggga ttcatacagc    8880
ggccagccat ccgtcatcca tatcaccacg tcaaagggtg acagcaggct cataagacgc    8940
cccagcgtcg ccatagtgcg ttcaccgaat acgtgcgcaa caaccgtctt ccgaagcctg    9000
tcatacgcgt aaaacagcca gcgctggcgc gatttagccc cgacatagcc ccactgttcg    9060
tccatttccg cgcagacgat gacgtcactg cccggctgta tgcgcgaggt taccgactgc    9120
ggcctgagtt ttttaagtga cgtaaaatcg tgttgaggcc aacgcccata atgcgggcag    9180
ttgcccggca tccaacgcca ttcatggcca tatcaatgnn tttctggtgc gtaccnggtt    9240
gagaagcggt gtaagtgaac tgcagttgcc atgttttacg gcagtgagag cagagatagc    9300
gctgatgtcc ggcagtgctt tgccgttac gcaccccccc gtcagtagct gaacaggagg     9360
gacagctgat agaaacagaa gccactggag cacctcaaaa caccatcata cactaaatca    9420
gtaagttggc agcatcaccc agttgatgcg caacggtacg attattccag cgaataacac    9480
ggtatcgtta ggagcagtag ggacttcggc ggtaagtctg ggattaacgg caaattacgc    9540
acgtaccgga gggcaggtga ctgcagggaa tgtgcaatcg attattggcg tgacttttgt    9600
ttatcaataa agaaatcaca gggcattgct aatgcaggta cgcaatatta cctgaagcta    9660
aaaacctgca cgttagccct ttgtaggcca gataagacgc gtcagcgtcg catctggcat    9720
aaacaaagcg cactttgccg acaatccgaa cagagctcgc cattggcagg ctctggtgtt    9780
cttttacgct accatgctaa taatcaacac aataatcagc ccaaccacgg agttgaccag    9840
ctccagcagt ccccaggttt tcaacgtgtc ttttaccgac aggtcaaagt aacctttgaa    9900
cagccagaat gaggcatcat taatgtgggt gagggtgttg gaacccgcag ccgtcgccag    9960
caccagcagc gccggattca cgccaaccag ctgaccggtt gctggatcaa ggattgcagc   10020
actgataatc ccggcggcgg tcatcgccga aacgacaccc tgacccgtcg ccagacgaat   10080
tagcacagtg atcagccatg ccataatgta gggcgagata ttgccgtggg acatcaacat   10140
gccgatggtg tcgccaatgc cggtgtcgat gatagtttgc ttcaacacgc cacccgcacc   10200
gatgatcaga atcaccattg caatgctttt caccgcactt tcaaaagcgt tcatcaccca   10260
ctgcatgtca tgaccacgtg cggtgccaaa gagtacgaat gcaaccacca tcgcaataaa   10320
cattgcaatc ggcgaggaac cgataaagtt aaccacttcc caggcagggg tatcttttac   10380
cagccagata ttggcgatgg tggtgggat cataatgatc gccgggatca gcggcaccag    10440
aatcgaaacg ccgaaagagg gcagattgtt catatctacc ggttgatctg ctttcaggaa   10500
```

```
tgatggcgtt gggcgctcaa gattgccgag gaacttcggc aggatcagac ctgcgcagat   10560
tacacttggg atcgtcacca gtacgccata gatataaacc atccccatat ctgcgccata   10620
agcattcacc agcgccacag gacccggctg cggtgggaac agtgaatgtg cggtagtggc   10680
agctgctact gccgggatcg ccagtttcag gaacggaatt ttagcttcgg cggcaatgac   10740
aataaccagc ggcgctaaca tgataaaggc cacttcatag aacatcgcca gaccaaaaat   10800
caggccgatg ataatcaccg acagctgtac atagcgcaga ccgagacgcg ccagcagcgt   10860
atgtgctatc tggtgagccg cgccggagtc gaccatcaat ttaccgatga ccgcaccgaa   10920
caccacgatg atagccagtt cccccagcgt gttgccgaag cccgctttca tggtgtgcag   10980
cagcgacatc aaatccattc ccgccagcat cccgacggac agcgccgcca ccaacaaagc   11040
caccattgaa ttgattttga acttcaaatt cagtaccagc atcagaccaa tgccgaatac   11100
cacccagaga atgttaagca catgcataac gttttacctt acctggttga accgttgtta   11160
ttttgggcga catgttatgt aaattggtca accattgttg cgatgaatgt cacatcctct   11220
gatcaataac catcgattac cctttgctgc aatttgcagc aacaaccagg agagtgaaat   11280
tcttgtgatg tggttaacca attttagaat tcgggttgac atgtattacc aaaaggtaga   11340
acttatacgc catctcatcc gatgcaacgc cacggctgcg gtctggttgt tcatccggat   11400
acctaaacaa ctccagggtt ccgcgtctct ttgctgtgga acccactatg tgaaagagga   11460
aaaatcatgg aacagacctg cgcctggtac ggcccaaacg atccggtttc tttagctgat   11520
gtccgtcagg cgggcgcaac tggcgtggtt accgcgctgc accatatccc gaacggcgaa   11580
gtatggtccg ttgaagagat cctcaaacgc aaggcgatcg ttgaagacgc aggcctggta   11640
tggtctgtcg tagaaagcgt gccaattcac gaagatatca aaacccacac tggcaactat   11700
gagcagtgga tcgctaacta tcagcagact ctgcgcaacc tggcgcagtg cggcattcgc   11760
accgtgtgct acaacttcat gccggtgctc gactggaccc gtactgacct cgaatacgtg   11820
ctgccagacg gctccaaagc tctgcgcttt gaccagatcg aattcgctgc attcgaaatg   11880
catatcctga acgtccagg cgcggaagcg gattacaccg aagaagaaat tgctcaggca   11940
gctgttcgct tcgccactat gagcgacgaa gacaaagcgc gtctgacccg taacatcatt   12000
gctggtcttc cgggcgcgga agaagggtac accctcgacc agttccgtaa gcacctggag   12060
ctatataaag atatcgacaa agccaaactg cgcgaaaact tgccgtcttc ctgaaaagcg   12120
attattccgg ttgccgaaga agttggcgtc cgtatggctg ttcacccgga cgatccgccg   12180
cgcccgatcc tcggcctgcc gcgcattgtt ccaccattg aagatatgca gtggatggtt   12240
gataccgtaa acagcatggc gaacggtttc accatgtgca ccggttccta cggcgtgcgt   12300
gctgacaacg atctggttga tatgatcaag cagttcggtc cgcgtattta cttcacccat   12360
ctgcgctcca ccatgcgtga agataacccg aaaaccttcc acgaagcggc gcacctgaac   12420
ggtgacgttg atatgtacga agtggtgaaa gcgattgttg aagaagaaca ccgtcgtaaa   12480
gcggaaggca agaagacct gatcccgatg cgtccggacc acggtcatca gatgctggac   12540
gacctgaaga gaaaaaccaa cccaggttac tccgcaattg gtcgtctgaa aggcctggcc   12600
gaagttcgcg tgtcgaact ggcgatccag cgcgcttttct ttagccgtta atatccaccg   12660
gcatggctgc gcgccgtgcc ggttccttct tccttgccgt cactctctga agacggattc   12720
tggagtttac gatgactact attgttgaca gcaatctgcc ggttgcccgc ccgtcatggg   12780
agcattctcg tctggaatca cgcattgtgc atctcggttg cggggcgttt caccgcgcgc   12840
```

```
-continued accaggcgct gtatacccat catctgctgg aaagcaccga cagcgactgg ggtatctgcg    12900
aagttaacct gatgccaggt aacgaccgtg tgctgattga aaacctgaaa aaacagcaac    12960
tgctgtacac cgtggcggaa aaaggcgcgg aaagcaccga actgaaaatt atcggttcga    13020
tgaaagaagc gctgcatccg gaaatcgacg gctgcgaagg tattctcaac gcgatgcgc     13080 gtccgcagac ggcgattgtc tctctgacgg tcacggaaaa aggctactgc gctgatgcgg    13140
caagcggtca gttggatctc aataacccgc tgatcaagca cgatctggaa aacccgactg    13200
cgccgaagtc tgcgattggt tacatcgtcg aagccctgcg tctgcgtcgt gaaaaagggc    13260
tgaaagcgtt tacggtgatg tcctgcgata acgtgcgtga aaacggtcat gtggcgaagg    13320
tcgcggtact ggggctggct caggcgcgtg acccgcagct ggcggcatgg attgaagaga    13380
acgtcacctt cccgtgcac                                                 13399
```

METHODS OF IDENTIFYING AN ORGANISM

RELATED APPLICATION

This application is a continuation-in-part of U.S. nonprovisional patent application Ser. No. 12/120,586 filed May 14, 2008, which claims priority to and the benefit of U.S. provisional application Ser. No. 61/029,816 filed Feb. 19, 2008, the content of each of which is incorporated by reference herein in its entirety.

TECHNICAL FIELD

This disclosure relates to methods of identifying an organism, e.g., a microorganism. The methods can include imaging nucleic acid of the organism.

BACKGROUND

Physical mapping of genomes, e.g., using restriction endonucleases to develop restriction maps, can provide accurate information about the nucleic acid sequences of various organisms. Restriction maps of, e.g., deoxyribonucleic acid (DNA), can be generated by optical mapping. Optical mapping can produce ordered restriction maps by using fluorescence microscopy to visualize restriction endonuclease cutting events on individual labeled DNA molecules.

SUMMARY

The present invention provides methods of identifying an organism, e.g., a microorganism. The methods include obtaining a restriction map of a nucleic acid from an organism and correlating the restriction map of the nucleic acid with a restriction map database, thereby identifying the organism. With use of a detailed restriction map database, the organism can be identified and classified not just at a genus and species level, but also at a sub-species (strain), a sub-strain, and/or an isolate level. The featured methods offer fast, accurate, and detailed information for identifying organisms. The methods can be used in a clinical setting, e.g., a human or veterinary setting; or in an environmental or industrial setting (e.g., clinical or industrial microbiology, food safety testing, ground water testing, air testing, contamination testing, and the like). In essence, the invention is useful in any setting in which the detection and/or identification of a microorganism is necessary or desirable.

This invention also features methods of diagnosing a disease or disorder in a subject by, inter alia, identifying an organism by correlating the restriction map of a nucleic acid from the organism with a restriction map database and correlating the identity of the organism with the disease or disorder.

In one aspect, the invention provides a method of identifying an organism. The method includes obtaining a restriction digest of a nucleic acid sample, imaging the restriction fragments, and comparing the imaged data to a database. Restriction maps of the invention can be ordered by, for example, attaching nucleic acids to a surface, elongating them on the surface and exposing to one or more restriction endonucleases. Generally, preferred methods of the invention comprise obtaining a nucleic acid sample from an organism; imaging the nucleic acid; obtaining a restriction map of the nucleic acid; and correlating the restriction map of the nucleic acid with a restriction map database, thereby identifying the organism.

The detected organism can be a microorganism, a bacterium, a protist, a virus, a fungus, or disease-causing organisms including microorganisms such as protozoa and multicellular parasites. The nucleic acid can be deoxyribonucleic acid (DNA), a ribonucleic acid (RNA) or can be a cDNA copy of an RNA obtained from a sample. The nucleic acid sample includes any tissue or body fluid sample, environmental sample (e.g., water, air, dirt, rock, etc.), and all samples prepared therefrom.

Methods of the invention can further include digesting nucleic acid with one or more enzymes, e.g., restriction endonucleases, e.g., BglII, NcoI, XbaI, and BamHI, prior to imaging. Preferred restriction enzymes include, but are not limited to:

| | | |
|---|---|---|
| AflII | ApaLI | BglII |
| AflII | BglII | NcoI |
| ApaLI | BglII | NdeI |
| AflII | BglII | MluI |
| AflII | BglII | PacI |
| AflII | MluI | NdeI |
| BglII | NcoI | NdeI |
| AflII | ApaLI | MluI |
| ApaLI | BglII | NcoI |
| AflII | ApaLI | BamHI |
| BglII | EcoRI | NcoI |
| BglII | NdeI | PacI |
| BglII | Bsu36I | NcoI |
| ApaLI | BglII | XbaI |
| ApaLI | MluI | NdeI |
| ApaLI | BamHI | NdeI |
| BglII | NcoI | XbaI |
| BglII | MluI | NcoI |
| BglII | NcoI | PacI |
| MluI | NcoI | NdeI |
| BamHI | NcoI | NdeI |
| BglII | PacI | XbaI |
| MluI | NdeI | PacI |
| Bsu36I | MluI | NcoI |
| ApaLI | BglII | NheI |
| BamHI | NdeI | PacI |
| BamHI | Bsu36I | NcoI |
| BglII | NcoI | PvuII |
| BglII | NcoI | NheI |
| BglII | NheI | PacI |

Imaging ideally includes labeling the nucleic acid. Labeling methods are known in the art and can include any known label. However, preferred labels are optically-detectable labels, such as 4-acetamido-4'-isothiocyanatostilbene-2, 2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron® Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; naphthalo cyanine, BOBO, POPO, YOYO, TOTO and JOJO.

A database for use in the invention can include a restriction map similarity cluster. The database can include a restriction map from at least one member of the Glade of the organism. The database can include a restriction map from at least one subspecies of the organism. The database can include a restriction map from a genus, a species, a strain, a sub-strain, or an isolate of the organism. The database can include a restriction map with motifs common to a genus, a species, a strain, a sub-strain, or an isolate of the organism.

In another aspect, the invention features a method of diagnosing a disease or disorder in a subject, including obtaining a sample suspected to contain an organism to be detected; (b) imaging a nucleic acid from the organism; (c) obtaining a restriction map of the nucleic acid; (d) identifying the organism by correlating the restriction map of the nucleic acid with a restriction map database; and (e) correlating the identity of the organism with the disease or disorder.

Methods can further include treating a disease or disorder in a subject, including diagnosing a disease or disorder in the subject as described above and providing treatment to the subject to ameliorate the disease or disorder. Treatment can include administering a drug to the subject.

In one embodiment, a restriction map obtained from a single DNA molecule is compared against a database of restriction maps from known organisms in order to identify the closest match to a restriction fragment pattern occurring in the database. This process can be repeated iteratively until sufficient matches are obtained to identify an organism at a predetermined confidence level. According to methods of the invention, nucleic acid from a sample are prepared and imaged as described herein. A restriction map is prepared and the restriction pattern is correlated with a database of restriction patterns for known organisms. In a preferred embodiment, organisms are identified from a sample containing a mixture of organisms. In a highly-preferred embodiment, methods of the invention are used to determine a ratio of various organisms present in a sample suspected to contain more than one organism. Moreover, use of methods of the invention allows the detection of multiple microorganisms from the same sample, either serially or simultaneously.

In use, the invention can be applied to identify a microorganism making up a contaminant in an environmental sample. For example, methods of the invention are useful to identify a potential biological hazard in a sample of air, water, soil, clothing, luggage, saliva, urine, blood, sputum, food, drink, and others. In a preferred embodiment, methods of the invention are used to detect and identify an organism in a sample obtained from an unknown source. In essence, methods of the invention can be used to detect biohazards in any environmental or industrial setting.

The invention is also useful to prepare and use arrays and other nucleic acid platforms using sequences that are specific for a target strain of an infectious agent. For example, sequence ID NOS 1-3 represent unique genomic regions in the E. coli STEC outbreak in Germany. Those sequences are prepared using any number of techniques known to the skilled artisan to form diagnostic arrays capable of distinguishing virulent from non-virulent strains of E. coli. For example, PCR primers, hybridization probes and the like are prepared to test material to determine the presence and identity of virulent strains in a patient sample.

Techniques for identifying and/or confirming the presence of virulent E. coli are independent of any particular platform and may be conducted without preparation of an optical map. For example, SEQ ID NOS 1-3 are useful for preparing sequence-specific primers for amplification of unique regions of the virulent strains for rapid identification. Those sequences are fragmented (e.g., sonically, enzymatically, mechanically) into short fragments useful as primers (e.g., 20-mers to 100-mers). The primers are then applied to a prepared sample in order to amplify the unique region, if present, in the sample. Other techniques, such as sequencing, arrays (e.g., comparative genomic hybridization arrays, ordered arrays, molecular inversion probe arrays, etc), hybrid capture, chromatography and the like are useful with the sequences, or portions of them, disclosed in SEQ ID NOS 1-3. Techniques for isolating and preparing DNA are provided throughout the application and are generally known in the art.

In general, diagnostic information using the sequences disclosed herein is obtained using any suitable modality, including optical mapping, sequencing, hybrid capture and the like.

Further aspects and features of the invention will be apparent upon inspection of the following detailed description thereof.

All patents, patent applications, and references cited herein are incorporated in their entireties by reference.

DETAILED DESCRIPTION

Figure 1:
FIG. 1 is a diagram showing restriction maps of six isolates of E. coli.

The present disclosure features methods of identifying an organism, e.g., a microorganism. The methods include obtaining a restriction map of a nucleic acid, e.g., DNA, from an organism and correlating the restriction map of the nucleic acid with a restriction map database, thereby identifying the organism. With use of a detailed restriction map database that contains motifs common to various groups and sub-groups, the organism can be identified and classified not just at a genus and species level, but also at a sub-species (strain), a sub-strain, and/or an isolate level. For example, bacteria can be identified and classified at a genus level, e.g., *Escherichia* genus, species level, e.g., *E. coli* species, a strain level, e.g., O157, CFT, and K12 strains of *E. coli*, and isolates, e.g., O157:H7 isolate of *E. coli* (as described in Experiment 3B below). The featured methods offer a fast, accurate, and detailed information for identifying organisms. These methods can be used in a variety of clinical settings, e.g., for identification of an organism in a subject, e.g., a human or an animal subject.

This disclosure also features methods of diagnosing a disease or disorder in a subject by, inter alia, identifying an organism via correlating the restriction map of a nucleic acid from the organism with a restriction map database, and correlating the identity of the organism with the disease or disorder. These methods can be used in a clinical setting, e.g., human or veterinary setting.

Methods of the invention are also useful for identifying and/or detecting an organism in food or in an environmental setting. For example, methods of the invention can be used to assess an environmental threat in drinking water, air, soil, and other environmental sources. Methods of the invention are also useful to identify organisms in food and to determine a common source of food poisoning in multiple samples that are separated in time or geographically, as well as samples that are from the same or similar batches.

Restriction Mapping

The methods featured herein utilize restriction mapping during both generation of the database and processing of an organism to be identified. One type of restriction mapping that can be used is optical mapping. Optical mapping is a single-molecule technique for production of ordered restriction maps from a single DNA molecule (Samad et al., Genome Res. 5:1-4, 1995). During this method, individual fluorescently labeled DNA molecules are elongated in a flow of agarose between a coverslip and a microscope slide (in the first-generation method) or fixed onto polylysine-treated glass surfaces (in a second-generation method). Id. The added endonuclease cuts the DNA at specific points, and the fragments are imaged. Id. Restriction maps can be constructed based on the number of fragments resulting from the digest. Id. Generally, the final map is an average of fragment sizes derived from similar molecules. Id. Thus, in one embodiment of the present methods, the restriction map of an organism to be identified is an average of a number of maps generated from the sample containing the organism.

Optical mapping and related methods are described in U.S. Pat. No. 5,405,519, U.S. Pat. No. 5,599,664, U.S. Pat. No. 6,150,089, U.S. Pat. No. 6,147,198, U.S. Pat. No. 5,720,928, U.S. Pat. No. 6,174,671, U.S. Pat. No. 6,294,136, U.S. Pat. No. 6,340,567, U.S. Pat. No. 6,448,012, U.S. Pat. No. 6,509, 158, U.S. Pat. No. 6,610,256, and U.S. Pat. No. 6,713,263, each of which is incorporated by reference herein. Optical Maps are constructed as described in Reslewic et al., Appl Environ Microbiol. 2005 September; 71 (9):5511-22, incorporated by reference herein. Briefly, individual chromosomal fragments from test organisms are immobilized on derivatized glass by virtue of electrostatic interactions between the negatively-charged DNA and the positively-charged surface, digested with one or more restriction endonuclease, stained with an intercalating dye such as YOYO-1 (Invitrogen) and positioned onto an automated fluorescent microscope for image analysis. Since the chromosomal fragments are immobilized, the restriction fragments produced by digestion with the restriction endonuclease remain attached to the glass and can be visualized by fluorescence microscopy, after staining with the intercalating dye. The size of each restriction fragment in a chromosomal DNA molecule is measured using image analysis software and identical restriction fragment patterns in different molecules are used to assemble ordered restriction maps covering the entire chromosome.

Restriction Map Database

The database(s) used with the methods described herein can be generated by optical mapping techniques discussed supra. The database(s) can contain information for a large number of isolates, e.g., about 200, about 300, about 400, about 500, about 600, about 700, about 800, about 900, about 1,000, about 1,500, about 2,000, about 3,000, about 5,000, about 10,000 or more isolates. In addition, the restriction maps of the database contain annotated information (a similarity cluster) regarding motifs common to genus, species, sub-species (strain), sub-strain, and/or isolates for various organisms. The large number of the isolates and the information regarding specific motifs allows for accurate and rapid identification of an organism.

The restriction maps of the database(s) can be generated by digesting (cutting) nucleic acids from various isolates with specific restriction endonuclease enzymes. Some maps can be a result of digestion with one endonuclease. Some maps can be a result of a digest with a combination of endonucleases, e.g., two, three, four, five, six, seven, eight, nine, ten or more endonucleases. The exemplary endonucleases that can be used to generate restriction maps for the database(s) and/or the organism to be identified include: BglII, NcoI, XbaI, and BamHI. Non-exhaustive examples of other endonucleases that can be used include: AluI, ClaI, DpnI, EcoRI, HindIII, KpnI, PstI, SacI, and SmaI. Yet other restriction endonucleases are known in the art.

Map alignments between different strains are generated with a dynamic programming algorithm which finds the optimal alignment of two restriction maps according to a scoring model that incorporates fragment sizing errors, false and missing cuts, and missing small fragments (See Myers et al., Bull Math Biol 54:599-618 (1992); Tang et al., J Appl Probab 38:335-356 (2001); and Waterman et al., Nucleic Acids Res 12:237-242). For a given alignment, the score is proportional to the log of the length of the alignment, penalized by the differences between the two maps, such that longer, better-matching alignments will have higher scores.

To generate similarity clusters, each map is aligned against every other map. From these alignments, a pair-wise alignment analysis is performed to determine "percent dissimilarity" between the members of the pair by taking the total length of the unmatched regions in both genomes divided by the total size of both genomes. These dissimilarity measurements are used as inputs into the agglomerative clustering method "Agnes" as implemented in the statistical package "R". Briefly, this clustering method works by initially placing each entry in its own cluster, then iteratively joining the two nearest clusters, where the distance between two clusters is the smallest dissimilarity between a point in one cluster and a point in the other cluster.

Organisms to be Identified

Various organisms, e.g., viruses, and various microorganisms, e.g., bacteria, protists, and fungi, can be identified with the methods featured herein. In one embodiment, the organism's genetic information is stored in the form of DNA. The genetic information can also be stored as RNA.

The sample containing the organism to be identified can be a human sample, e.g., a tissue sample, e.g., epithelial (e.g., skin), connective (e.g., blood and bone), muscle, and nervous tissue, or a secretion sample, e.g., saliva, urine, tears, and feces sample. The sample can also be a non-human sample, e.g., a horse, camel, llama, cow, sheep, goat, pig, dog, cat, weasel, rodent, bird, reptile, and insect sample. The sample can also be from a plant, water source, food, air, soil, plants, or other environmental or industrial sources.

Identifying an Organism

The methods described herein, i.e., methods of identifying an organism, diagnosing a disease or disorder in a subject, determining antibiotic resistance of an organism, determining an antibiotic resistance profile of a bacterium, and determining a therapeutically effective antibiotic to administer to a subject, and treating a subject, include correlating the restriction map of a nucleic acid of an organism with a restriction map database. The methods involve comparing each of the raw single molecule maps from the unknown sample (or an average restriction map of the sample) against each of the entries in the database, and then combining match probabilities across different molecules to create an overall match probability.

In one embodiment of the methods, entire genome of the organism to be identified can be compared to the database. In another embodiment, several methods of extracting shared elements from the genome can be created to generate a reduced set of regions of the organism's genome that can still serve as a reference point for the matching algorithms.

As discussed above and in the Examples below, the restriction maps of the database can contain annotated information (a similarity cluster) regarding motifs common to genus, species, sub-species (strain), sub-strain, and/or isolates for various organisms. Such detailed information would allow identification of an organism at a sub-species level, which, in turn, would allow for a more accurate diagnosis and/or treatment of a subject carrying the organism.

In another embodiment, methods of the invention are used to identify genetic motifs that are indicative of an organism, strain, or condition. For example, methods of the invention are used to identify in an isolate at least one motif that confers antibiotic resistance. This allows appropriate choice of treatment without further cluster analysis.

Applications

The methods described herein can be used in a variety of settings, e.g., to identify an organism in a human or a non-human subject, in food, in environmental sources (e.g., food, water, air), and in industrial settings. The featured methods also include methods of diagnosing a disease or disorder in a subject, e.g., a human or a non-human subject, and treating the subject based on the diagnosis. The method includes: obtaining a sample comprising an organism from the subject; imaging a nucleic acid from the organism; obtaining a restriction map of said nucleic acid; identifying the organism by correlating the restriction map of said nucleic acid with a restriction map database; and correlating the identity of the organism with the disease or disorder.

As discussed above, various organisms can be identified by the methods discussed herein and therefore various diseases and disorders can be diagnosed by the present methods. The organism can be, e.g., a cause, a contributor, and/or a symptom of the disease or disorder. In one embodiment, more than one organism can be identified by the methods described herein, and a combination of the organisms present can lead to diagnosis. Skilled practitioners would be able to correlate the identity of an organism with a disease or disorder. For example, the following is a non-exhaustive list of some diseases and bacteria known to cause them: tetanus—*Clostridium tetani*; tuberculosis—*Mycobacterium tuberculosis*; meningitis—*Neisseria meningitidis*; botulism—*Clostridium botulinum*; bacterial dysentry—*Shigella dysenteriae*; lyme disease—*Borrelia burgdorferi*; gasteroenteritis—*E. coli* and/or *Campylobacter* spp.; food poisoning—*Clostridium perfringens, Bacillus cereus, Salmonella enteriditis*, and/or *Staphylococcus aureus*. These and other diseases and disorders can be diagnosed by the methods described herein.

Once a disease or disorder is diagnosed, a decision about treating the subject can be made, e.g., by a medical provider or a veterinarian. Treating the subject can involve administering a drug or a combination of drugs to ameliorate the disease or disorder to which the identified organism is contributing or of which the identified organism is a cause. Amelioration of the disease or disorder can include reduction in the symptoms of the disease or disorder. The drug administered to the subject can include any chemical substance that affects the processes of the mind or body, e.g., an antibody and/or a small molecule, The drug can be administered in the form of a composition, e.g., a composition comprising the drug and a pharmaceutically acceptable carrier. The composition can be in a form suitable for, e.g., intravenous, oral, topical, intramuscular, intradermal, subcutaneous, and anal administration. Suitable pharmaceutical carriers include, e.g., sterile saline, physiological buffer solutions and the like. The pharmaceutical compositions may be additionally formulated to control the release of the active ingredients or prolong their presence in the patient's system. Numerous suitable drug delivery systems are known for this purpose and include, e.g., hydrogels, hydroxmethylcellulose, microcapsules, liposomes, microemulsions, microspheres, and the like. Treating the subject can also include chemotherapy and radiation therapy.

The following examples provide illustrative embodiments of the present methods and should not be treated as restrictive.

Optical Mapping Combined with Sequencing

In certain embodiments, optical mapping is combined with sequencing to obtain further information related to the optical mapping data. In particular, when an optical map of an unknown organism is compared to an optical map of a reference organism or to a database of optical maps, the map of the unknown organism will have conserved and non-conserved regions with respect to the organisms with which it is compared. Since the sequence of the conserved regions are known, primers may be designed against conserved regions of the unknown organism that flank the non-conserved regions. Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering.

The primers are hybridized to the conserved regions that flank the non-conserved regions and used as a starting point for a sequencing reaction. In this manner, sequence information is obtained on the non-conserved regions of the unknown organism. Any technique for sequencing nucleic acid known to those skilled in the art can be used in the methods of the provided invention. DNA sequencing techniques include classic dideoxy sequencing reactions (Sanger method as described by Sanger et al., Proc Natl Acad Sci USA, 74(12): 5463 67 (1977)). Another conventional sequencing method involves chemical degradation of nucleic acid fragments. using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Sequences can be read that originate from a single molecule or that originate from amplifications from a single molecule. Millions of independent amplifications of single molecules can be performed in parallel either on a solid surface or in tiny compartments in water/oil emulsion. The DNA sample to be sequenced can be diluted and/or dispersed sufficiently to obtain one molecule in each compartment. This dilution can be followed by DNA amplification to generate copies of the original DNA sequences and creating "clusters" of molecules all having the same sequence. These clusters can then be sequenced. Many millions of reads can be generated in one run. Sequence can be generated starting at the 5' end of a given strand of an amplified sequence and/or sequence can be generated from starting from the 5' end of the complementary sequence. In a preferred embodiment, sequence from strands is generated, i.e. paired end reads.

Algorithms are used to determine which sequences generated by the sequencer originate from the DNA sequence. Individually measured sequences (reads) may be offset relative to each other, contain errors introduced by amplification and/or by sequencing. An algorithm can be used to combine reads together to more accurately determine the frequency of a DNA sequence in the starting material.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Microbial Identification Using Optical Mapping

Microbial identification (ID) generally has two phases. In the first, DNA from a number of organisms are mapped and compared against one another. From these comparisons, important phenotypes and taxonomy are linked with map features. In the second phase, single molecule restriction maps are compared against the database to find the best match.

Database Building and Annotation

Maps sufficient to represent a diversity of organisms, on the basis of which it will be possible to discriminate among various organisms, are generated. The greater the diversity in the organisms in the database, the more precise will be the ability to identify an unknown organism. Ideally, a database contains sequence maps of known organisms at the species and sub-species level for a sufficient variety of microorganisms so as to be useful in a medical or industrial context. However, the precise number of organisms that are mapped into any given database is determined at the convenience of the user based upon the desired use to which the database is to be put.

After sufficient number of microorganisms are mapped, a map similarity cluster is generated. First, trees of maps are generated. After the tree construction, various phenotypic and taxonomic data are overlaid, and regions of the maps that uniquely distinguish individual clades from the rest of the populations are identified. The goal is to find particular clades that correlate with phenotypes/taxonomies of interest, which will be driven in part through improvements to the clustering method.

Once the clusters and trees have been annotated, the annotation will be applied back down to the individual maps. Additionally, if needed, the database will be trimmed to include only key regions of discrimination, which may increase time performance.

Calling (Identifying) an Unknown

One embodiment of testing the unknowns involves comparing each of the raw single molecule maps from the unknown sample against each of the entries in the database, and then combining match probabilities across different molecules to create an overall match probability.

The discrimination among closely related organisms can be done by simply picking the most hits or the best match probability by comparing data obtained from the organism to data in the database. More precise comparisons can be done by having detailed annotations on each genome for what is a discriminating characteristic of that particular genome versus what is a common motif shared among several isolates of the same species. Thus, when match scores are aggregated, the level of categorization (rather than a single genome) will receive a probability. Therefore, extensive annotation of the genomes in terms of what is a defining characteristic and what is shared will be required.

In one embodiment of the method, entire genomes will be compared to all molecules. Because there will generally be much overlap of maps within a species, another embodiment can be used. In the second embodiment, several methods of extracting shared elements from the genome will be created to generate a reduced set of regions that can still serve as a reference point for the matching algorithms. The second embodiment will allow for streamlining the reference database to increase system performance.

Example 2

Using Multiple Enzymes for Microbial Identification

In one embodiment, the single molecule restriction maps from each of the enzymes will be compared against the database described in Example 1 independently, and a probable identification will be called from each enzyme independently. Then, the final match probabilities will be combined as independent experiments. This embodiment will provide some built-in redundancy and therefore accuracy for the process.

Introduction

In general, optical mapping can be used within a specific range of average fragment sizes, and for any given enzyme there is considerable variation in the average fragment size across different genomes. For these reasons, it typically will not be optimal to select a single enzyme for identification of clinically-relevant microbes. Instead, a small set of enzymes will be chosen to optimize the probability that for every organism of interest, there will be at least one enzyme in the database suitable for mapping.

Selection Criteria

A first step in the selection of enzymes was the identification of the bacteria of interest. These bacteria were classified into two groups: (a) the most common clinically interesting organisms and (b) other bacteria involved in human health. The chosen set of enzymes must have at least one enzyme that cuts each of the common clinically interesting bacteria within the range of average fragment sizes suitable for detailed comparisons of closely related genomes (about 6-13 kb). Additionally, for the remaining organisms, each fragment must be within the functional range for optical mapping (about 4-20 kb). These limits were determined through mathematical modeling, directed experiments, and experience with customer orders. Finally, enzymes that have already been used for Optical Mapping were selected.

Suggested Set

Based upon the above criteria, the preliminary set consisted of the enzymes BglII, NcoI, and XbaI, which have been used for optical mapping. There are 28 additional sets that cover the key organisms with known enzymes, so in the event that this set is not adequate, there alternatives will be utilized (data not shown).

Final Steps

Because the analysis in Experiment 2 is focused on the sequenced genomes, prior to full database production, this set of enzymes will be tested against other clinically important genomes, which will be part of the first phase of the proof of principle study.

Example 3

Identification of E. coli

A. In one embodiment of a microbial identification method, nucleic acids of between about 500 and about 1,000 isolates will be optically mapped. Then, unique motifs will be identified across genus, species, strains, substrains, and isolates. To identify a sample, single nucleic acid molecules of the sample will be aligned against the motifs, and p-values assigned for each motif match. The p-values will be combined to find likelihood of motifs. The most specific motif will give the identification.

Figure 2:
FIG. 2 is a diagram showing restriction maps of six isolates of E. coli clustered into three groups: O157 (that includes O157:H7 and 536), CFT (that includes CFT073 and 1381), and K12 (that includes K12 and 718).

B. The following embodiment illustrates a method of identifying E. coli down to an isolate level. Restriction maps of six E. coli isolates were obtained by digesting nucleic acids of these isolates with BamHI restriction enzyme. FIG. 1 shows restriction maps of these six E. coli isolates: 536, O157:H7 (complete genome), CFT073 (complete genome), 1381, K12 (complete genome), and 718. As shown in FIG. 2, the isolates clustered into three sub-groups (strains): O157 (that includes O157:H7 and 536), CFT (that includes CFT073 and 1381), and K12 (that includes K12 and 718).

Figure 3:
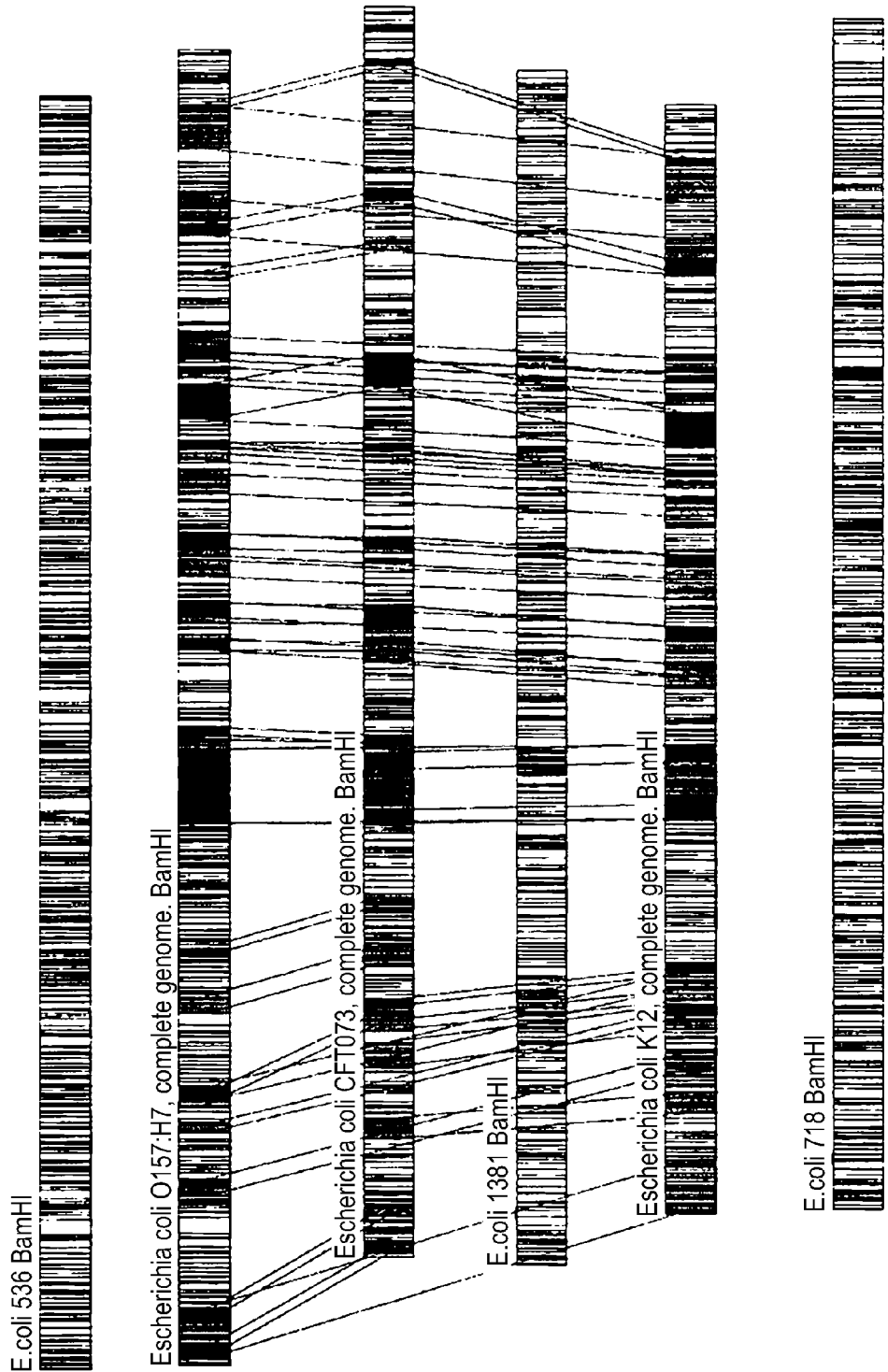
FIG. 3 is a diagram showing common motifs among restriction maps of six isolates of E. coli.
Figure 4:
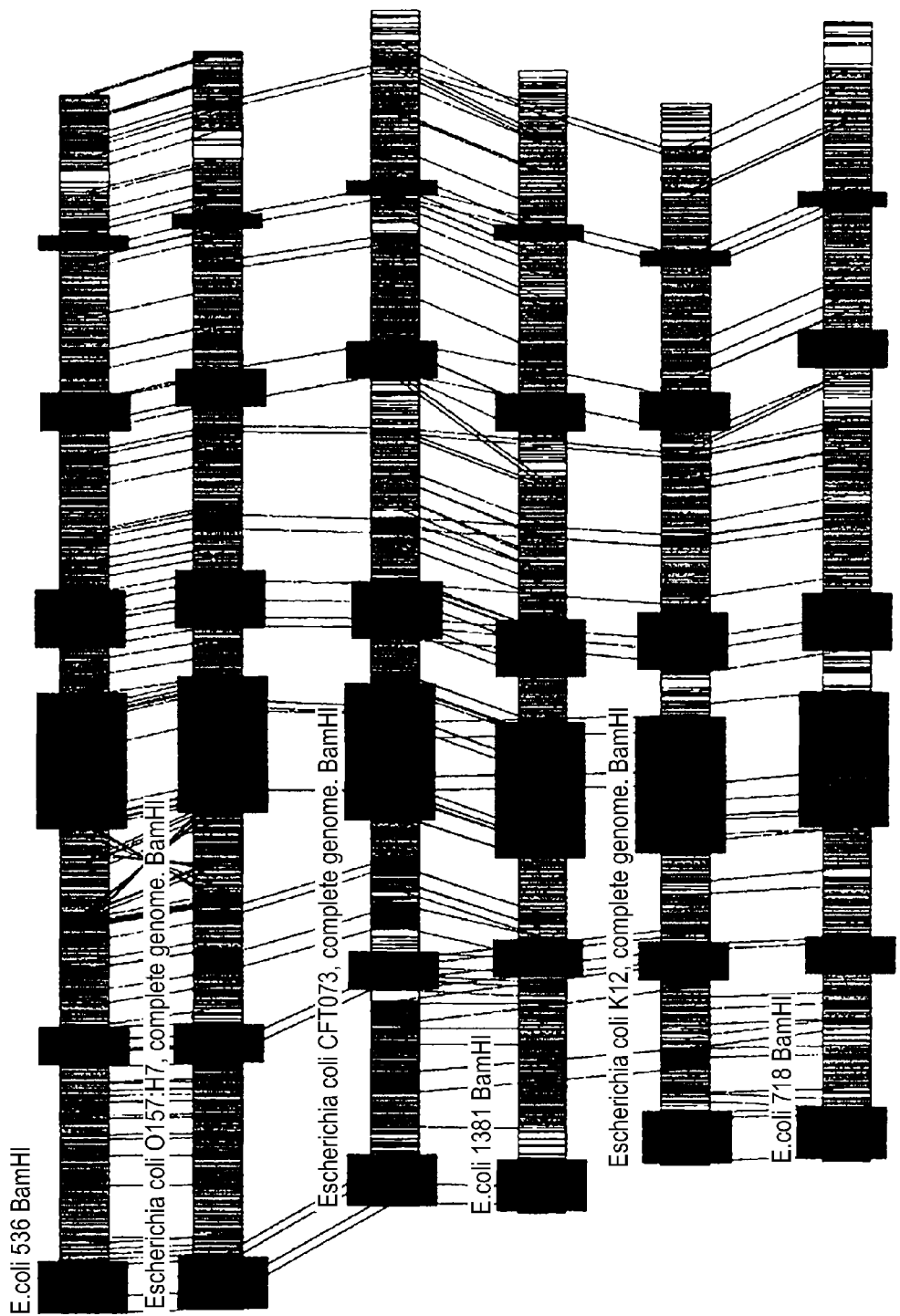
FIG. 4 is a diagram showing restriction maps of six isolates of E. coli, with the boxes indicating regions common to E. coli.
Figure 5:
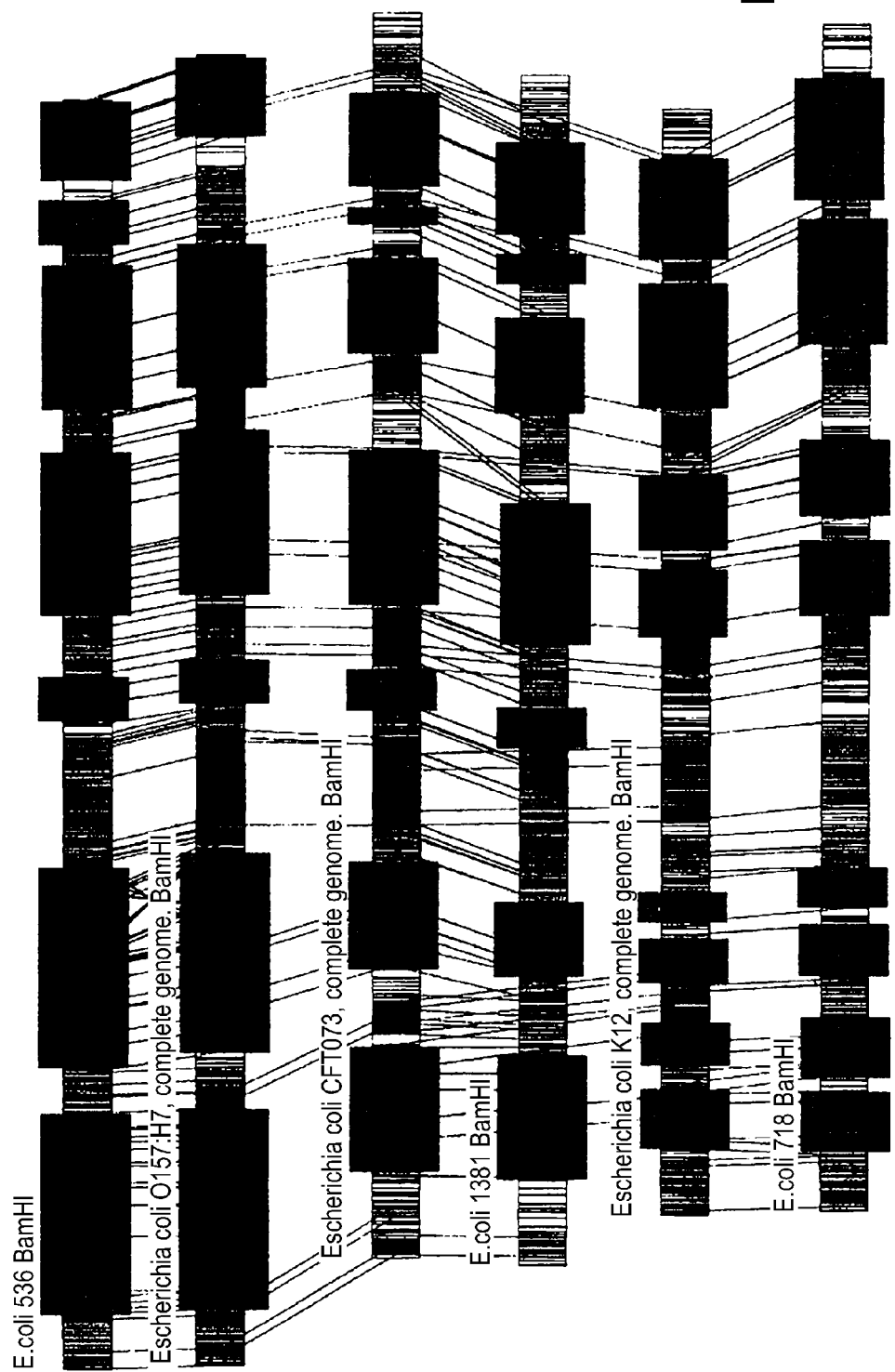
FIG. 5 is a diagram showing restriction maps of six isolates of E. coli, with the boxes indicating regions that are unique to a particular strain, namely O157, CFT, or K12.

These restriction maps provided multi-level information regarding relation of these six isolates, e.g., showed motifs that are common to all of the three sub-groups (see, FIG. 3) and regions specific to E. coli (see, boxed areas in FIG. 4). The maps were also able to show regions unique to each strain (see, boxed areas in FIG. 5) and regions specific to each isolate (see boxed regions in FIG. 6).

Figure 6:
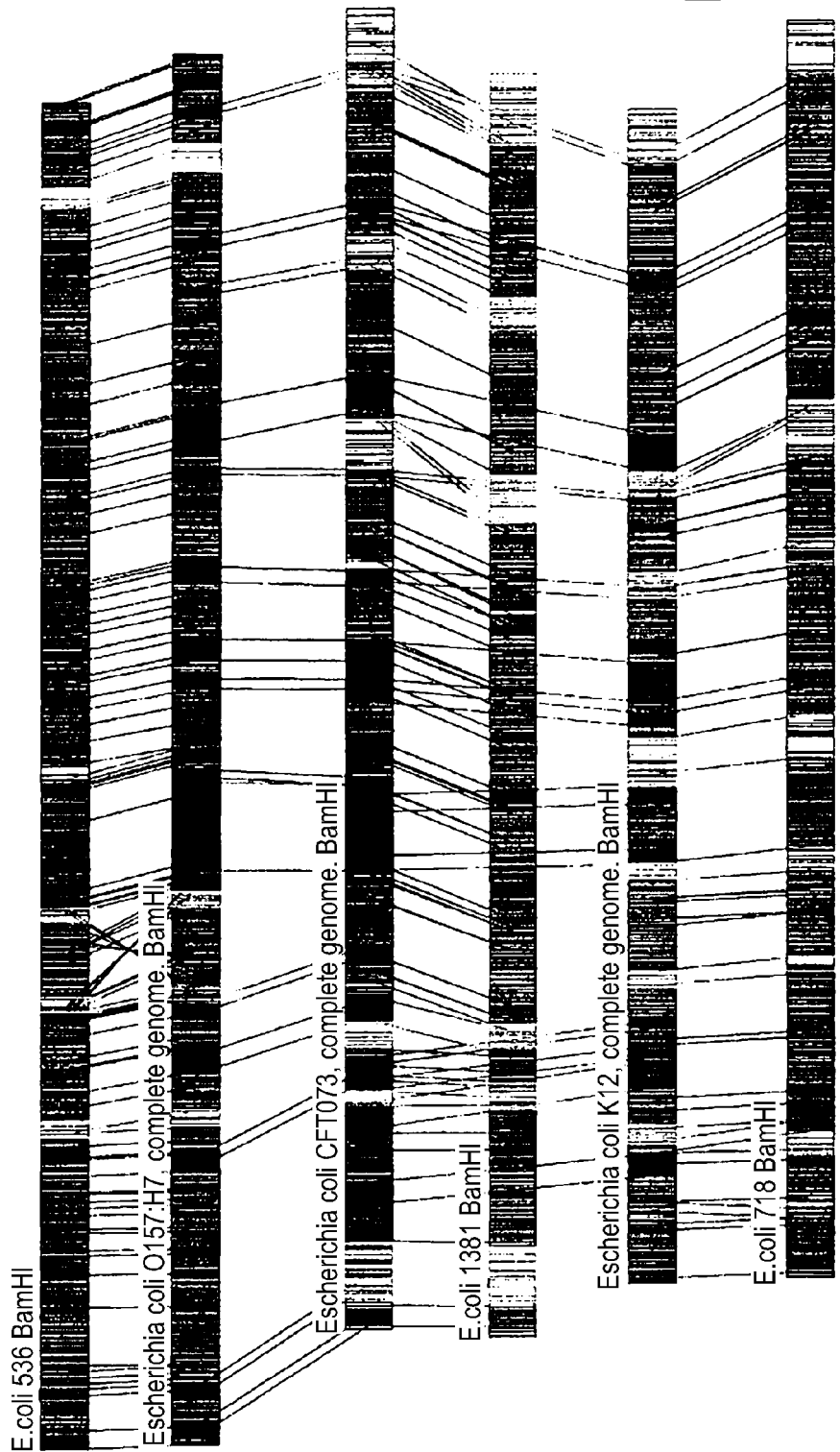
FIG. 6 is a diagram showing restriction maps of six isolates of E. coli, with the boxes indicating regions unique to each isolate.
Figure 7:
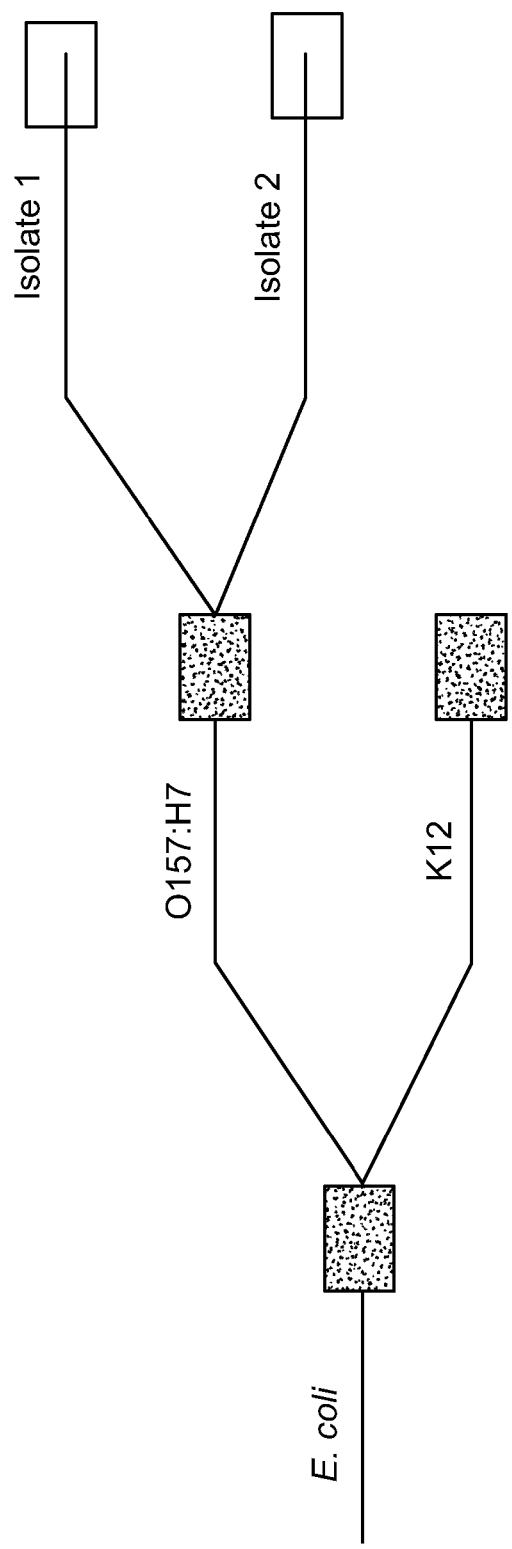
FIG. 7 is a tree diagram, showing possible levels of identifying E. coli.

This and similar information can be stored in a database and used to identify bacteria of interest. For example, a restriction map of an organism to be identified can be obtained by digesting the nucleic acid of the organism with BamHI. This restriction map can be compared with the maps in the database. If the map of the organism to be identified contains motifs specific to *E. coli*, to one of the sub-groups, to one of the strains, and/or to a specific isolate, the identity of the organism can be obtained by correlating the specific motifs. FIG. 6 shows a diagram to illustrate the possibilities of traversing variable lengths of a similarity tree.

Figure 8:
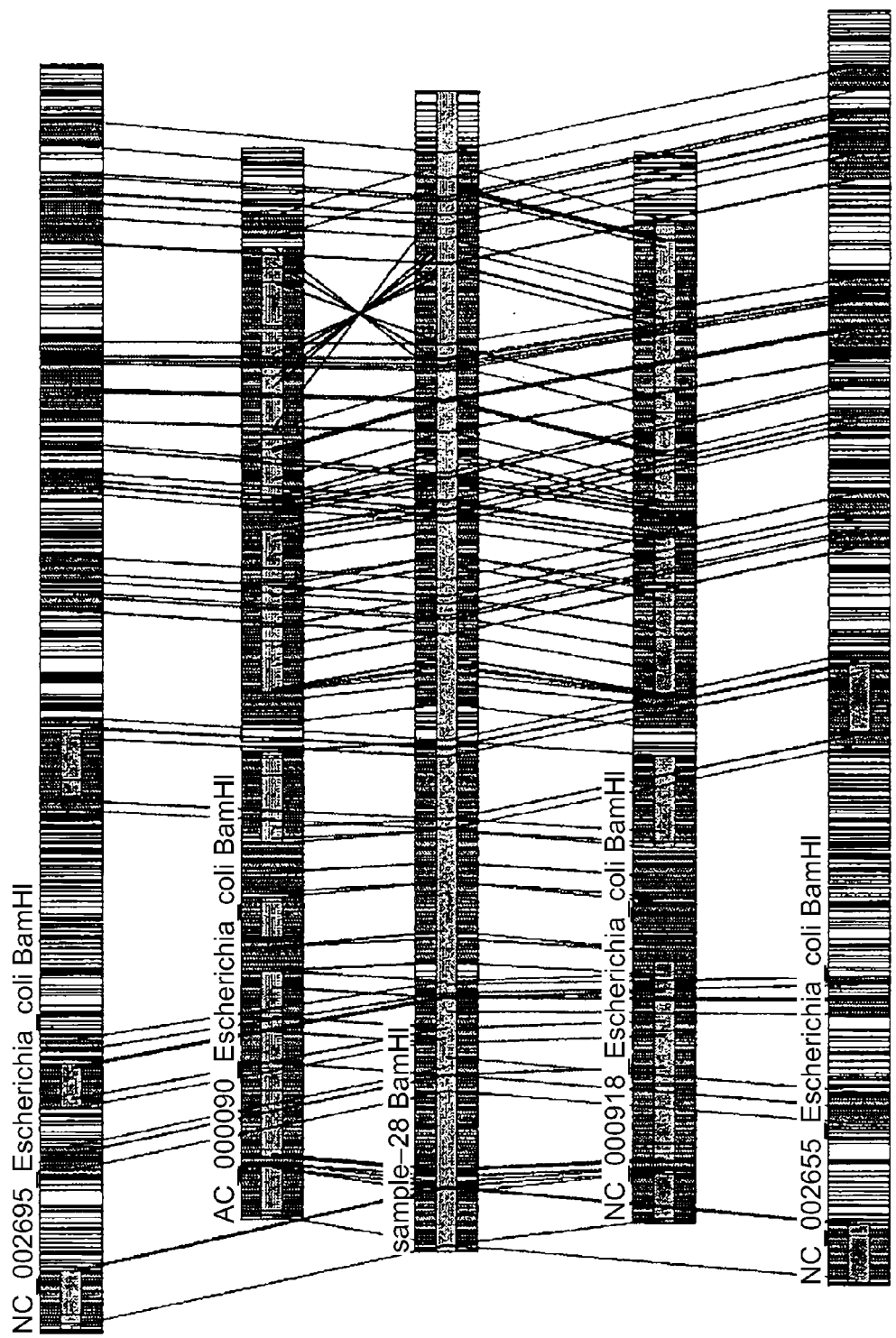
FIG. 8 is a diagram showing restriction maps of a sample (middle map) and related restriction maps from a database.

C. The following example illustrates identifying a sample as an *E. coli* bacterium. A sample (sample 28) was digested with BamHI and its restriction map obtained (see FIG. 8, middle restriction map). This sample was aligned against a database that contained various *E. coli* isolates. The sample was found to be similar to four *E. coli* isolates: NC 002695, AC 000091, NC 000913, and NC 002655. The sample was therefore identified as *E. coli* bacterium that is most closely related to the AC 000091 isolate.

Example 4

Optical Map Signature for Virulent *E. coli*

The 2011 German STEC outbreak has impacted a large number of people and caused greater than 20 deaths. The outbreak strain is extremely virulent inducing hemolytic-uremic syndrome (HUS) in greater than 25% of patients. In any outbreak it is important to have a way to rapidly differentiate an outbreak isolate from normal "background" strains in both patients and potential outbreak sources such as vegetables, meat, and dairy products. After an initial outbreak, if the strain is particularly virulent and becomes part of the (new) "background", patients infected with the virulent species will be tested for the virulent strain in order to proactively adjust management. For example, patients with severe *E coli* diarrhea will receive a reflex test for the O157:H7 strain. If positive, the patients will be moved to an ICU or other monitored facility and placed on HUS prevention protocols. Strain typing assays need to be performed rapidly to impact patient management. Immunoassays and molecular assays provide the most rapid result. However, the 2011 German STEC strain is known to share antigenic determinants (O104:H4) with other less pathogenic strains, so a molecular diagnostic is preferred.

Optical mapping technology was used in order to identify conserved genomic regions unique to the 2011 German *E. coli* outbreak strains. De novo optical mapping was used to identify genomic regions/islands that are conserved in all *E. coli* outbreak isolates and not present in other non-virulent *E coli* strains (i.e., an optical map signature that is indicative of a virulent strain of *E. coli*). Optical maps were prepared as described above and optical map comparisons were performed as described above. The conserved, outbreak-specific, genomic islands are located at the following four locations (see red elements in FIG. 9):

Region 1
Begin: 2,028,697 bp
End: 2,066,267 bp
Length 37,571 bp;
Region 2
Begin: 4,286,430 bp
End: 4,318,222 bp
Length: 31,793 bp;
Region 3
Begin: 4,890,135
End: 4,897,419 bp
Length: 7,285 bp; and
Region 4
Begin: 5,099,215 bp
End: 5,112,101 bp
Length: 12,887 bp.

All positions are relative to the origin of replication in the LB226692 optical map.

Figure 9:
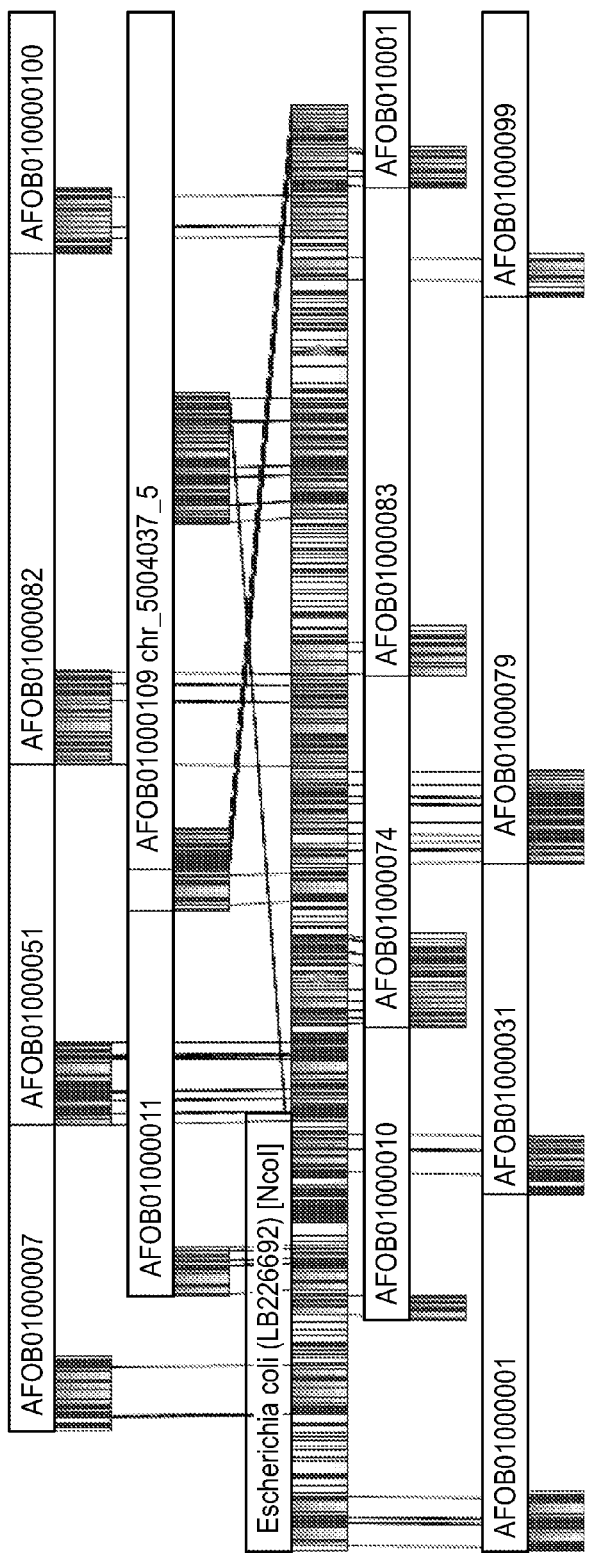
FIG. 9 is a set of optical maps showing conserved, outbreak-specific, genomic islands located at four locations in a reference optical map.
Figure 10:
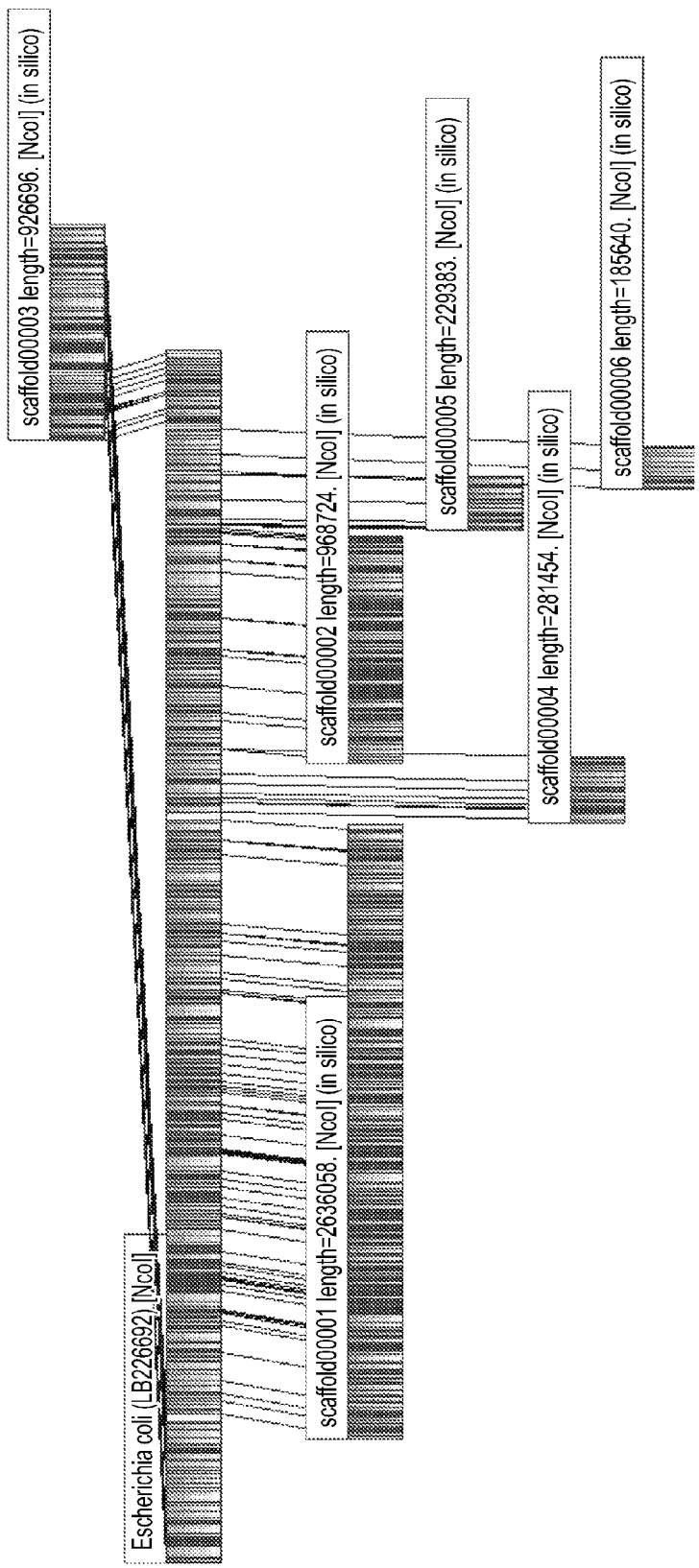
FIG. 10 is a is a set of optical maps showing conserved, outbreak-specific, genomic islands located at four locations in a reference optical map.

The sequences of the outbreak isolates were determined and the sequence contigs were aligned to a reference optical map (FIGS. 9-10). The sequences of the non-conserved regions that align to genomic island regions 1, 2, and 4 are set forth in SEQ ID NOs 1-3. This information is now useful for the development of molecular assays for the 2011 German STEC *E. coli* strain as well as any other *E. coli* strain using any one of a number of technologies including PCR, arrays, sequencing, or optical mapping.

The flanking sequence for genomic island 3 is known. This flanking sequence can be used by one with skill in the art to deduce the sequence of the $3^{rd}$ genomic island region.

The analysis performed herein was based upon the complete structure of the *E. coli* chromosome rather than on plasmids or other mobile elements. A such, the analysis herein is more likely to identify stable genetic regions.

What is claimed is:

1. A method of analyzing an unknown strain of an organism, the method comprising:
   obtaining a nucleic acid from an unknown strain of an organism;
   preparing an optical map from the nucleic acid;
   comparing the optical map of the unknown strain to at least one optical map of a known strain of the organism to identify conserved and non-conserved regions in the optical map of the unknown strain; and
   determining the sequence of the non-conserved regions of the unknown strain using primers that hybridize to conserved regions flanking said non-conserved regions.

2. The method according to claim 1, wherein the organism is *E. coli*.

3. The method according to claim 1, wherein the determining step comprises sequencing by synthesis.

4. The method according to claim 1, wherein the organism is obtained from at least one sample type selected from the group consisting of a food sample, an environmental sample, a mammalian tissue and a body fluid sample.

5. The method according to claim 4, wherein the environmental sample is selected from the group consisting of water, soil, sewage, and vegetable matter.

6. A method for analyzing an organism, the method comprising:
   obtaining a nucleic acid from an organism in a sample;
   preparing an optical map from the nucleic acid;
   comparing the optical map to at least one reference optical map to identify conserved and non-conserved regions in the optical map of the organism; and
   designing primers that flank the non-conserved regions of the organism, to thereby determine the sequence of the non-conserved regions of the organism.

7. The method according to claim 6, wherein the sequence of the non-conserved regions of the organism is determined using sequencing by synthesis.

8. The method according to claim 6, wherein the sample is selected from the group consisting of: a food sample, an environmental sample, a mammalian tissue and a body fluid sample.

9. The method according to claim 8, wherein the environmental sample is selected from the group consisting of water, soil, sewage, and vegetable matter.

\* \* \* \* \*